(12) United States Patent
Miyake et al.

(10) Patent No.: US 6,924,278 B2
(45) Date of Patent: Aug. 2, 2005

(54) AROYL-PIPERAZINE DERIVATIVES, THEIR PREPARATION AND THEIR USE AS TACHYKININ ANTAGONISTS

(75) Inventors: Hiroshi Miyake, Kyoto (JP); Kazuhiko Take, Osaka (JP); Shinji Shigenaga, Hyogo (JP); Hidenori Azami, Hyogo (JP); Hiroshi Sasaki, Hyogo (JP); Yoshiteru Eikyu, Nara (JP); Kazuo Nakai, Hyogo (JP); Junya Ishida, Hyogo (JP); Takashi Manabe, Hyogo (JP); Nobukiyo Konishi, Kyoto (JP); Tadashi Terasaka, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/720,021

(22) Filed: Nov. 24, 2003

(65) Prior Publication Data

US 2005/0027121 A1 Feb. 3, 2005

Related U.S. Application Data

(63) Continuation of application No. 09/446,145, filed as application No. PCT/JP98/02613 on Jun. 15, 1998, now abandoned.

(30) Foreign Application Priority Data

Jun. 17, 1997 (AU) ............................................. P07359

(51) Int. Cl.$^7$ ........................ A61K 31/33; A61K 31/54; A61K 31/495; C07D 417/00; C07D 413/00
(52) U.S. Cl. ................ 514/183; 514/227.8; 514/228.2; 514/235.8; 514/253; 544/60; 544/62; 544/121; 544/369
(58) Field of Search ........................... 514/227.8, 228.2, 514/235.8, 253; 544/60, 62, 121, 369

(56) References Cited

U.S. PATENT DOCUMENTS

| | | |
|---|---|---|
| 5,670,505 A | 9/1997 | Matsuo et al. |
| 5,883,098 A | 3/1999 | Matsuo et al. |
| 5,939,413 A | 8/1999 | Matsuo et al. |
| 6,087,357 A * | 7/2000 | Matsuo et al. ........... 514/227.8 |

FOREIGN PATENT DOCUMENTS

| | | | |
|---|---|---|---|
| EP | 655442 | * | 5/1995 |
| WO | 9630343 | | 10/1996 |
| WO | 9634864 | | 11/1996 |
| WO | 9637489 | | 11/1996 |
| WO | 9708166 | | 3/1997 |
| WO | 9722597 | | 6/1997 |

* cited by examiner

*Primary Examiner*—Richard L. Raymond
*Assistant Examiner*—Sudhaker B. Patel
(74) *Attorney, Agent, or Firm*—Oblon, Spivak, McClelland, Maier & Neustadt, P.C.

(57) ABSTRACT

This invention relates to piperazine derivatives of the formula:

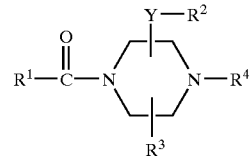

wherein each symbol is as defined in the description, and its pharmaceutically acceptable salt, to processes for preparation thereof, to pharmaceutical composition comprising the same, and to a use of the same for treating or preventing Tachykinin-mediated diseases in human being or animals.

7 Claims, No Drawings

AROYL-PIPERAZINE DERIVATIVES, THEIR PREPARATION AND THEIR USE AS TACHYKININ ANTAGONISTS

This application is a continuation of U.S. application Ser. No. 09/446,145 filed on Jan. 7, 2000, which is a 371 of PCT/JP98/02613, filed Jun. 15, 1998.

TECHNICAL FIELD

The present invention relates to new piperazine derivatives and a salt thereof.

More particularly, it relates to new piperazine derivatives and a salt thereof which have pharmacological activities such as Tachykinin antagonism, especially Substance P antagonism, Neurokinin A antagonism, Neurokinin B antagonism, and the like, to a process for preparation thereof, to a pharmaceutical composition comprising the same, and to a use of the same as a medicament.

Accordingly, one object of the present invention is to provide new and useful piperazine derivatives and a salt thereof which have pharmacological activities such as Tachykinin antagonism, especially Substance P antagonism, Neurokinin A antagonism, Neurokinin B antagonism, and the like.

Another object of the present invention is to provide a process for the preparation of said piperazine derivatives and a salt thereof.

A further object of the present invention is to provide a pharmaceutical composition comprising, as an active ingredient, said piperazine derivatives and a pharmaceutically acceptable salt thereof.

Still further object of the present invention is to provide a use of said piperazine derivatives or a pharmaceutically acceptable salt thereof as Tachykinin antagonist, especially Substance P antagonist, Neurokinin A antagonist or Neurokinin B antagonist, useful for treating or preventing Tachykinin-mediated diseases, for example, respiratory diseases such as asthma, bronchitis, rhinitis, cough, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g., migraine, headache, toothache, cancerous pain, back pain, etc.); and the like in human being or animals.

Some piperazine derivatives having pharmaceutical activities such as Tachykinin antagonism have been known as described in EP 0655442 A1 and WO 97/22597 A1.

DISCLOSURE OF INVENTION

The object compound of the present invention can be represented by the following general formula (I):

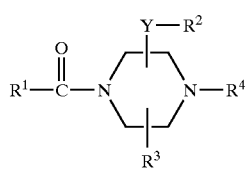

(I)

wherein
Y is bond or lower alkylene,
$R^1$ is aryl which may have substituent(s),
$R^2$ is aryl or indolyl, each of which may have substituent(s),
$R^3$ is hydrogen or lower alkyl,
$R^4$ is pyridyl(lower)alkylamino(lower)alkynyl;
  N-(lower alkyl)-N-[pyridyl(lower)alkyl]amino(lower)alkyl;
  hydroxy(lower)alkoxy(lower)alkyl;
  lower alkanoyl(lower)alkoxy(lower)alkyl;
  phenyl(lower)alkyl which has hydroxy(lower)alkyl or morpholinyl(lower)alkyl;
  ar(lower)alkoxycarbonyl:
  (2-pyridyl)(lower)alkyl which may have 1 to 3 substituent(s) selected from the group consisting of lower alkyl, lower alkoxy, lower alkoxycarbonyl, mono(or di or tri)halo(lower)alkyl and halogen;
  (3-pyridyl)propyl which may have lower alkoxy or amino;
  (3-pyridyl)butyl which may have lower alkoxy or amino;
  pyridyl(lower)alkenyl which may have lower alkoxy or amino;
  (2-pyridyl)(lower)alkynyl which may have 1 to 3 substituent(s) selected from the group consisting of lower alkyl, lower alkoxy, lower alkoxycarbonyl, mono (or di or tri)halo(lower)alkyl and halogen;
  (3-pyridyl)(lower)alkynyl which may have lower alkoxy or amino;
  pyridyl, thiazolyl, imidazolyl or pyrazolyl, each of which may have substituent(s);
  imidazolyl(lower)alkyl which may have 1 or 2 substituent(s) selected from the group consisting of lower alkyl, lower alkynyl, ar(lower)alkyl, pyridyl(lower)alkyl, mono(or di or tri)halo(lower)alkyl and halogen;
  pyrazolyl(lower)alkyl which may have hydroxy(lower)alkyl, carboxy(lower)alkyl, lower alkoxycarbonyl(lower)alkyl, morpholinyl(lower)alkyl or morpholinylcarbonyl(lower)alkyl;
  thiazolyl(lower)alkyl which may have lower alkyl;
  piperidyl(lower)alkyl which may have hydroxy(lower)alkyl or lower alkoxy;
  morpholinyl(lower)alkyl which has 1 or 2 substituent(s) selected from the group consisting of ethyl, hydroxy(lower)alkyl, halo(lower)alkyl and lower alkoxy(lower)alkyl;
  morpholinyl(lower)alkyl which has lower alkyl and lower alkoxy(lower)alkyl;
  (3,5-dimethylmorpholino)(lower)alkyl;
  morpholino(lower)alkenyl which may have lower alkyl or lower alkoxy(lower)alkyl;
  (2- or 3-morpholinyl)(lower)alkenyl which may have lower alkoxycarbonyl;
  pyrrolidinyl(lower)alkynyl which may have lower alkoxy(lower)alkyl;
  morpholinyl(lower)alkynyl which may have 1 or 2 substituent(s) selected from the group consisting of ethyl, propyl, isopropyl, isobutyl, spirocyclo(lower)alkyl, lower alkoxy(lower)alkyl, hydroxy(lower)alkyl, carboxy(lower)alkyl, di(lower alkyl)carbamoyl, lower alkoxycarbonyl and halo(lower)alkyl;

morpholinyl(lower)alkynyl which has methyl and lower alkoxy;

(dimethylmorpholino)(lower)alkynyl;

homomorpholinyl(lower)alkynyl which have halogen;

(morpholinylamino)propyl which may have lower alkanoyl;

thiomorpholinyl(lower)alkynyl which may have substituent(s);

homomorpholinylamino(lower)alkyl;

thiomorpholinylamino(lower)alkyl; or saturated heterocyclicimino(lower)alkyl, saturated heterocyclicaminocarbonyl(lower)alkyl or saturated heterocyclic(lower)alkoxy(lower)alkyl, each of which may have substituent(s), provided that when $R^4$ is 2-[N-methyl-N-(3-pyridylmethyl)amino]ethyl, 3-(3-pyridyl)propyl, 3-(3-pyridyl)-2-propynyl, 4-[(2-methoxymethyl)pyrrolidino]-2-butynyl, 4-thiomorpholino-2-butynyl, 3-(morphlinoamino)propyl, 4-morpholino-2-butenyl, 4-morpholino-2-butynyl, or 4-(3,3-dimethylmorpholino)-2-butynyl, then $R^1$ is not 3,5-bis(trifluoromethyl)phenyl.

It is to be noted that the object compound (I) may include one or more stereoisomers due to asymmetric carbon atom(s) and double bond, and all of such isomers and a mixture thereof are included within the scope of the present invention.

It is further to be noted that isomerization or rearrangement of the object compound (I) may occur due to the effect of the light, acid, base or the like, and the compound obtained as the result of said isomerization or rearrangement is also included within the scope of the present invention.

It is also to be noted that the solvating form of the compound (I) (e.g. hydrate, etc.) and any form of the crystal of the compound (I) are included within the scope of the present invention.

According to the present invention, the object compound (I) or a salt thereof can be prepared by processes which are illustrated in the following schemes.

Process 1

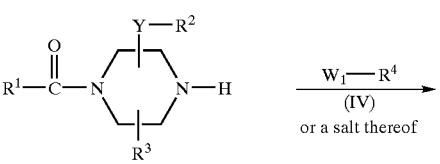

(II)
or its reactive derivative
at the imino group
or a salt thereof

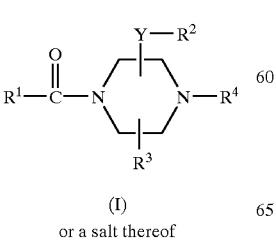

(I)
or a salt thereof

Process 2

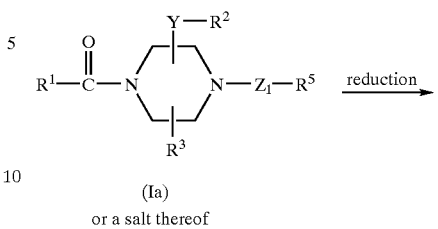

(Ia)
or a salt thereof

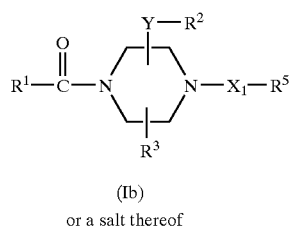

(Ib)
or a salt thereof

Process 3

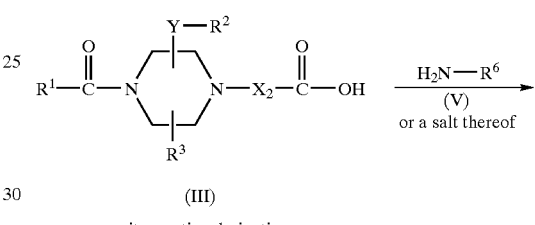

(III)
or its reactive derivative
at the carboxy group
or a salt thereof

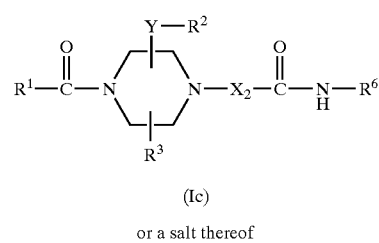

(Ic)
or a salt thereof

Process 4

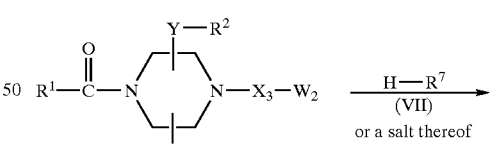

(VI)
or a salt thereof

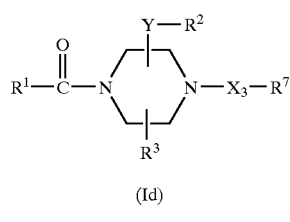

(Id)
or a salt thereof

-continued

Process 5

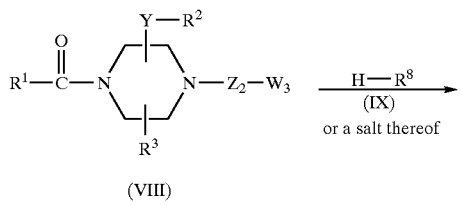

(VIII)

or a salt thereof

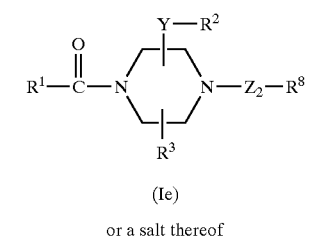

(Ie)

or a salt thereof

Process 6

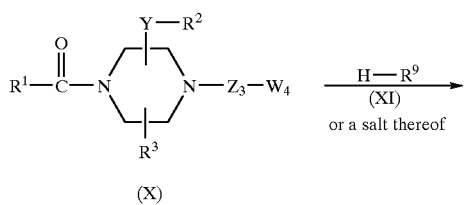

(X)

or a salt thereof

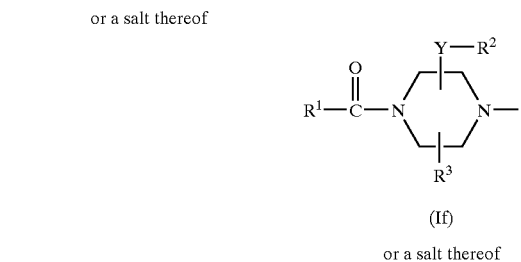

(If)

or a salt thereof wherein
Y, $R^1$, $R^2$, $R^3$ and $R^4$ are each as defined above,
$X_1$, $X_2$ and $X_3$ are each lower alkylene,
$Z_1$ and $Z_3$ are each lower alkynylene,
$Z_2$ is lower alkenylene,
$R^5$ is 2-pyridyl which may have 1 to 3 substituent(s) selected from the group consisting of lower alkyl, lower alkoxy, lower alkoxycarbonyl, mono(or di or tri)halo(lower)alkyl and halogen; or
3-pyridyl which may have lower alkoxy or amino,
$R^6$ is saturated heterocyclic which may have substituent(s),
$R^7$ is pyridyl(lower)alkylamino;
  N-(lower alkyl)-N-[pyridyl(lower)alkyl]amino;
  1-imidazolyl which may have 1 or 2 substituent(s) selected from the group consisting of lower alkyl, lower alkynyl, ar(lower)alkyl, pyridyl(lower)alkyl, mono(or di or tri)halo(lower)alkyl and halogen;
  1-pyrazolyl which may have hydroxy(lower)alkyl, carboxy(lower)alkyl, lower alkoxycarbonyl(lower)alkyl, morpholinyl(lower)alkyl or morpholinylcarbonyl(lower)alkyl;
  piperidino which may have hydroxy(lower)alkyl or lower alkoxy;
  morpholino which has 1 or 2 substituent(s) selected from the group consisting of ethyl, hydroxy(lower)alkyl, halo(lower)alkyl and lower alkoxy(lower)alkyl;

morpholino which has lower alkyl and lower alkoxy (lower)alkyl;
  3,5-dimethylmorpholino;
  morpholinylamino which may have lower alkanoyl;
  homomorpholinylamino; or
  thiomorpholinylamino,
$R^8$ is morpholino which may have lower alkyl or lower alkoxy(lower)alkyl,
$R^9$ is pyrrolidino which may have lower alkoxy(lower)alkyl;
  morpholino which may have 1 or 2 substituent(s) selected from the group consisting of ethyl, propyl, isopropyl, isobutyl, spirocyclo(lower)alkyl, lower alkoxy(lower)alkyl, hydroxy(lower)alkyl, carboxy(lower)alkyl, di(lower alkyl)carbamoyl, lower alkoxycarbonyl and halo(lower)alkyl;
  morpholino which has methyl and lower alkoxy;
  dimethylmorpholino; or homomorpholino which has halogen,
$W_1$, $W_2$, $W_3$ and $W_4$ are each a leaving group.

As to the starting compounds (II), (III), (IV), (V), (VI), (VII), (VIII), (IX) and (X), some of them are novel and can be prepared by the procedures described in the Preparations and Examples mentioned later or similar manners thereto.

Suitable salts of the starting and object compounds are conventional non-toxic and pharmaceutically acceptable salt and include an acid addition salt such as an organic acid salt (e.g. acetate, trifluoroacetate, fumarate, maleate, tartrate, methanesulfonate, benzenesulfonate, formate, toluenesulfonate, etc.), an inorganic acid salt (e.g. hydrochloride, hydrobromide, hydroiodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention intends to include within the scope thereof are explained in detail as follows.

The term "lower" is intended to mean 1 to 6, preferably 1 to 4, carbon atom(s), unless otherwise indicated.

Suitable "lower alkylene" may include straight or branched one having 1 to 6 carbon atom(s), such as methylene, ethylene, trimethylene, propylene, tetramethylene, methylmethylene, methyltrimethylene, hexamethylene, and the like, in which the preferred one is methylene, ethylene, trimethylene or methylmethylene.

Suitable "lower alkenylene" may include straight or branched one having 2 to 6 carbon atom(s) such as vinylene, propenylene, 1-(or 2-)butenylene, 1-(or 2- or 3-)pentenylene, 1-(or 2- or 3-)hexenylene, methylvinylene, ethylvinylene, 1-(or 2- or 3-)methylpropenylene, 1-(or 2- or 3-)ethylpropenylene, 1-(or 2- or 3- or 4-)methyl-1-(or 2-)butenylene, and the like.

Suitable "lower alkynylene" may include one having 2 to 6 carbon atoms, such as ethynylene, propynylene, butynylene, and the like, in which the preferred one is propynylene or butynylene.

Suitable "halogen" and "halogen" moiety in the terms "mono(or di or tri)halo(lower)alkyl", "mono(or di or tri)halo($C_1$–$C_4$)alkyl", etc. may include fluorine, chlorine, bromine and iodine.

Suitable "lower alkyl" and "lower alkyl" moiety in the terms "pyridyl(lower)alkylamino(lower)alkynyl", "N-

(lower alkyl)-N-[pyridyl(lower)alkyl]amino(lower)alkyl", etc. may include straight or branched one having 1 to 6 carbon atom(s), such as methyl, ethyl, propyl, isopropyl, butyl, isobutyl, pentyl, hexyl and the like, preferably one having 1 to 5 carbon atom(s).

Suitable "lower alkenyl" moiety in the terms "3-pyridyl(lower)alkenyl", "saturated heterocyclic(lower)alkenyl", etc. may include vinyl, 1-(or 2-)propenyl, 1-(or 2- or 3-)butenyl, 1-(or 2- or 3- or 4-)pentenyl, 1-(or 2- or 3- or 4- or 5-)hexenyl, methylvinyl, ethylvinyl, 1-(or 2- or 3-)methyl-1-(or 2-)propenyl, 1-(or 2- or 3-)ethyl-1-(or 2-)propenyl, 1-(or 2- or 3- or 4-)methyl-1-(or 2- or 3-)butenyl, and the like, in which more preferable example may be $C_2$–$C_4$ alkenyl.

Suitable "lower alkynyl" moiety in the terms "pyridyl(lower)alkylamino(lower)alkynyl", "(2-pyridyl)(lower)alkynyl", etc. may include ethynyl, 1-propynyl, propargyl, 1-methylpropargyl, 1-(or 2- or 3-)butynyl, 1-(or 3-)methyl-2-butynyl, 1-(or 3-)ethyl-2-butynyl, 1-(or 3-)propyl-2-butynyl, 1-(or 3-)isopropyl-2-butynyl, 1-(or 2- or 3- or 4-)pentynyl, 1-(or 2- or 3- or 4- or 5-)hexynyl and the like, in which more preferable example may be $C_2$–$C_5$ alkynyl.

Suitable "aryl" may include phenyl, naphthyl, and the like, in which the preferred one is $C_6$–$C_{10}$ aryl and the most preferred one is phenyl or naphthyl.

Suitable "lower alkanoyl" and "lower alkanoyl" moiety in the term "lower alkanoyl(lower)alkoxy(lower)alkyl" may include formyl, acetyl, propanoyl, butanoyl, 2-methylpropanoyl, pentanoyl, 2,2-dimethylpropanoyl, hexanoyl and the like.

Suitable "lower alkoxy" and "lower alkoxy" moiety in the terms "hydroxy(lower)alkoxy(lower)alkyl", "lower alkanoyl(lower)alkoxy(lower)alkyl", etc. may include methoxy, ethoxy, propoxy, isopropoxy, butoxy, isobutoxy, t-butoxy, pentyloxy, t-pentyloxy, hexyloxy and the like.

Suitable "saturated heterocyclic" and "saturated heterocyclic" moiety in the terms "saturated heterocyclicimino(lower)alkyl", "saturated heterocyclicaminocarbonyl(lower)alkyl", etc. may include saturated 3 to 8-membered (more preferably 5 to 7-membered) heteromonocyclic group containing 1 to 4 nitrogen atom(s), for example, pyrrolidinyl, imidazolidinyl, piperidyl, piperazinyl, hexamethyleneimino, etc.;

saturated 3 to 8-membered (more preferably 5 or 6-membered) heteromonocyclic group containing 1 or 2 oxygen atom(s) and 1 to 3 nitrogen atom(s), for example, morpholinyl, homomorpholinyl, sydnonyl, etc.;

saturated 3 to 8-membered (more preferably 5 or 6-membered) heteromonocyclic group containing 1 or 2 sulfur atom(s) and 1 to 3 nitrogen atom(s), for example, thiazolidinyl, thiomorpholinyl, etc.;

saturated heterobicyclic group of the formula:

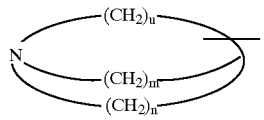

(wherein u, m and n are each integer of 1 to 6);

saturated heterobicyclic group of the formula:

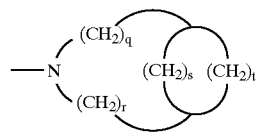

(wherein q, r, s and t are each integer of 1 to 6); and the like.

Suitable "substituent" in the terms "aryl which may have substituent(s)", "aryl or indolyl, each of which may have substituent(s)", "pyridyl, thiazolyl, imidazolyl or pyrazolyl, each of which may have substituent(s)" and "saturated heterocyclicimino(lower)alkyl, saturated heterocyclicaminocarbonyl(lower)alkyl or saturated heterocyclic(lower)alkoxy(lower)alkyl, each of which may have substituent(s)" may include lower alkyl (e.g., methyl, ethyl, propyl, isopropyl, butyl, isobutyl, tert-butyl, pentyl, neopentyl, tert-pentyl, hexyl, etc.), cyclo(lower)alkyl (e.g., cyclopropyl, cyclobutyl, cyclopentyl, cyclohexyl, etc.), lower alkylenedioxy (e.g., methylenedioxy, ethylenedioxy, propylenedioxy, etc.), lower alkoxy (e.g., methoxy, ethoxy, propoxy, isopropoxy, isobutoxy, tert-butoxy, pentyloxy, neopentyloxy, tert-pentyloxy, hexyloxy, etc.), lower alkoxy(lower)alkyl (e.g., methoxymethyl, ethoxymethyl, 1-methoxyethyl, 2-methoxyethyl, 1-ethoxyethyl, 2-ethoxyethyl, etc.), lower alkanoyl (e.g., formyl, acetyl, propionyl, butyryl, isobutyryl, etc.), lower alkoxycarbonyl (e.g., methoxycarbonyl, ethoxycarbonyl, propylcarbonyl, isopropylcarbonyl, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, etc.), mono(or di or tri)halo(lower)alkyl (e.g., fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.), halogen (e.g., chlorine, bromine, fluorine and iodine), carboxy, protected carboxy, hydroxy, protected hydroxy, aryl (e.g., phenyl, naphthyl, etc.), ar(lower)alkyl such as phenyl(lower)alkyl (e.g., benzyl, phenethyl, phenylpropyl, etc.), carboxy(lower)alkyl wherein lower alkyl moiety can be referred to the ones as exemplified above, protected carboxy(lower)alkyl wherein lower alkyl moiety can be referred to the ones as exemplified above, nitro, amino, protected amino, lower alkylamino (e.g. methylamino, ethylamino, isopropylamino, etc.), di(lower)alkylamino (e.g., dimethylamino, diethylamino, diisopropylamino, ethylmethylamino, isopropylmethylamino, ethylisopropylamino, etc.), hydroxy, hydroxy(lower)alkyl (e.g. hydroxymethyl, hydroxyethyl, etc.), protected hydroxy(lower)alkyl, acyl, cyano, oxo, mercapto, lower alkylthio (e.g., methylthio, ethylthio, propylthio, isopropylthio, butylthio, etc.), lower alkylsulfinyl (e.g., methylsulfinyl, ethylsulfinyl, propylsulfinyl, isopropylsulfinyl, butylsulfinyl, etc.), imino, morpholinyl (e.g., 2-morpholinyl, 3-morpholinyl, morpholino), bivalent group of the formula:

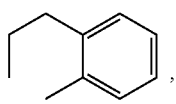

carboxy(lower)alkyl (e.g., carboxymethyl, carboxyethyl, carboxypropyl, etc.), lower alkoxycarbonyl (e.g., methoxycarbonyl, ethoxycarbonyl, propoxycarbonyl, isopropoxycarbonyl, isobutoxycarbonyl, tert-butoxycarbonyl, pentyloxycarbonyl, neopentyloxycarbonyl, tert-pentyloxycarbonyl, hexyloxycarbonyl, etc.), spirocyclo(lower)alkyl (e.g., spirocyclopropyl, spirocyclobutyl, spirocyclopentyl, etc.), ar(lower)alkoxycarbonyl(lower)alkyl (e.g., benzyloxycarbonylmethyl, benzyloxycarbonylethyl, benzyloxycarbonylpropyl, etc.), pyridyl(lower)alkyl (e.g., pyridylmethyl, pyridylethyl, etc.), carbamoyl, lower alkylcarbamoyl (e.g. methylcarbamoyl, ethylcarbamoyl, etc.), di(lower alkyl)carbamoyl (e.g. dimethylcarbamoyl, diethylcarbamoyl, etc.), and the like.

Suitable "leaving group" may include lower alkoxy (e.g. methoxy, ethoxy, propoxy, isopropoxy, butoxy, isobutoxy, t-butoxy, pentoxy, etc.), aryloxy (e.g. phenoxy, naphthoxy, etc.), an acid residue or the like.

Suitable "acid residue" may be halogen (e.g. chlorine, bromine, iodine, etc.), sulfonyloxy (e.g. methanesulfonyloxy, phenylsulfonyloxy, mesitylenesulfonyloxy, toluenesulfonyloxy, etc.) or the like.

Preferred embodiments of the object compound (I) are as follows:

Y is lower alkylene (more preferably $C_1$–$C_4$ alkylene, most preferably methylene);

$R^1$ is aryl (more preferably $C_6$–$C_{10}$ aryl, most preferably phenyl) which may have 1 to 3 (more preferably 1 or 2, most preferably 2) substituent(s) [more preferably substituent selected from the group consisting of mono(or di or tri)halo(lower)alkyl (more preferably trihalo(lower)alkyl, most preferably trifluoromethyl), halogen (more preferably chlorine), lower alkylamino (more preferably $C_1$–$C_4$ alkylamino, most preferably methylamino), di(lower)alkylamino (more preferably di($C_1$–$C_4$)alkylamino, most preferably dimethylamino) and nitro];

$R^2$ is aryl (more preferably $C_6$–$C_{10}$ aryl, most preferably phenyl or naphthyl) or indolyl, each of which may have 1 to 3 (more preferably 1 or 2) substituent(s) [more preferably substituent selected from the group consisting of lower alkyl (more preferably $C_1$–$C_4$ alkyl, most preferably methyl), mono(or di or tri)halo(lower)alkyl (more preferably mono(or di or tri)halo($C_1$–$C_4$)alkyl, most preferably trifluoromethyl), lower alkylenedioxy (more preferably $C_1$–$C_4$ alkylenedioxy, most preferably methylenedioxy or ethylenedioxy), hydroxy, hydroxy(lower)alkyl (more preferably hydroxy($C_1$–$C_4$)alkyl, most preferably hydroxymethyl), lower alkoxy (more preferably $C_1$–$C_4$ alkoxy, most preferably methoxy), lower alkylamino (more preferably $C_1$–$C_4$ alkylamino, most preferably methylamino) and di(lower)alkylamino (more preferably di($C_1$–$C_4$)alkylamino, most preferably dimethylamino)];

$R^3$ is hydrogen; and $R^4$ is pyridyl(lower)alkylamino(lower)alkynyl (more preferably pyridyl($C_1$–$C_4$)alkylamino($C_2$–$C_4$)alkynyl, most preferably 4-[(3-pyridylmethyl)amino]-2-butynyl);

N-(lower alkyl)-N-[pyridyl(lower)alkyl]amino(lower)alkyl [more preferably N-($C_1$–$C_4$ alkyl)-N-[pyridyl($C_1$–$C_4$)alkyl]amino($C_1$–$C_4$)alkyl, most preferably 2-[N-methyl-N-(3-pyridylmethyl)amino]ethyl];

hydroxy(lower)alkoxy(lower)alkyl (more preferably hydroxy($C_1$–$C_4$)alkoxy($C_1$–$C_4$)alkyl, most preferably (hydroxyethoxy)ethyl);

lower alkanoyl(lower)alkoxy(lower)alkyl (more preferably $C_1$–$C_4$ alkanoyl($C_1$–$C_4$)alkoxy($C_1$–$C_4$)alkyl, most preferably formylmethoxyethyl);

phenyl(lower)alkyl (more preferably phenyl($C_1$–$C_4$) alkyl, most preferably benzyl) which has hydroxy(lower)alkyl (more preferably hydorxy($C_1$–$C_4$)alkyl, most preferably hydroxymethyl) or morpholinyl(lower)alkyl (more preferably morpholinyl($C_1$–$C_4$) alkyl, most preferably morpholinomethyl) [more preferably α-(hydroxymethyl)benzyl or α-(morpholinomethyl)benzyl];

ar(lower)alkoxycarbonyl (more preferably ($C_6$–$C_{10}$ aryl) ($C_1$–$C_4$)alkoxycarbonyl, most preferably phenylmethoxycarbonyl);

(2-pyridyl)(lower)alkyl (more preferably (2-pyridyl) ($C_1$–$C_4$)alkyl, more preferably (2-pyridyl)propyl or (2-pyridyl)butyl) which may have 1 to 3 (more preferably 1 or 2) substituent(s) selected from the group consisting of lower alkyl (more preferably $C_1$–$C_4$ alkyl, most preferably methyl), lower alkoxy (more preferably $C_1$–$C_4$ alkoxy, most preferably methoxy), lower alkoxycarbonyl (more preferably $C_1$–$C_4$ alkoxycarbonyl, most preferably methoxycarbonyl), mono(or di or tri)halo(lower)alkyl (more preferably trihalo($C_1$–$C_4$)alkyl, most preferably trifluoromethyl) and halogen (more preferably fluorine));

(3-pyridyl)propyl (more preferably 3-(3-pyridyl)propyl) which may have lower alkoxy (more preferably $C_1$–$C_4$ alkoxy, most preferably methoxy);

(3-pyridyl)butyl (more preferably 4-(3-pyridyl)butyl);

pyridyl(lower)alkenyl (more preferably pyridyl($C_2$–$C_4$) alkenyl, most preferably 3-(3-pyridyl)-2-propenyl);

(2-pyridyl)(lower)alkynyl (more preferably (2-pyridyl) ($C_2$–$C_4$)alkynyl, most preferably 3-(2-pyridyl)-2-propynyl or 4-(2-pyridyl)-3-butynyl) which may have 1 to 3 (more preferably 1 or 2) substituent(s) selected from the group consisting of lower alkyl (more preferably $C_1$–$C_4$ alkyl, most preferably methyl), lower alkoxy (more preferably $C_1$–$C_4$ alkoxy, most preferably methoxy), lower alkoxycarbonyl (more preferably $C_1$–$C_4$ alkoxycarbonyl, most preferably methoxycarbonyl), mono (or di or tri)halo(lower)alkyl (more preferably trihalo($C_1$–$C_4$)alkyl, most preferably trifluoromethyl) and halogen (more preferably fluorine);

(3-pyridyl)(lower)alkynyl (more preferably (3-pyridyl) ($C_2$–$C_4$)alkynyl, most preferably 3-(3-pyridyl)-2-propynyl or 4-(3-pyridyl)-3-butynyl) which may have lower alkoxy (more preferably $C_1$–$C_4$ alkoxy, most preferably methoxy) or amino;

pyridyl, thiazolyl, imidazolyl or pyrazolyl, each of which may have 1 to 3 (more preferably 1 or 2) substituent(s) [more preferably substituent selected from the group consisting of lower alkyl (more preferably $C_1$–$C_4$ alkyl, most preferably methyl or isopropyl), ar(lower)alkyl (more preferably phenyl($C_1$–$C_4$)alkyl, most preferably benzyl) and pyridyl(lower)alkyl (more preferably pyridyl($C_1$–$C_4$)alkyl, most preferably pyridylmethyl)];

imidazolyl(lower)alkyl (more preferably imidazolyl ($C_1$–$C_4$)alkyl, most preferably 3-(1H-imidazol-4-yl) propyl) which may have 1 or 2 substituent(s) selected from the group consisting of lower alkyl (more preferably $C_1$–$C_4$ alkyl, most preferably methyl or isopropyl), lower alkynyl (more preferably $C_2$–$C_5$ alkynyl, most preferably propargyl), ar(lower)alkyl (more preferably phenyl($C_1$–$C_4$)alkyl, most preferably benzyl), pyridyl(lower)alkyl (more preferably pyridyl ($C_1$–$C_4$)alkyl most preferably pyridylmethyl), mono(or di or tri)halo(lower)alkyl (more preferably trihalo ($C_1$–$C_4$)alkyl, most preferably trifluoromethyl) and halogen (more preferably fluorine);

pyrazolyl(lower)alkyl (more preferably pyrazolyl($C_1$–$C_4$) alkyl, most preferably (1H-pyrazol-4-yl)methyl or 3-(1H-pyrazol-1-yl)propyl) which may have hydroxy (lower)alkyl (more preferably hydroxy($C_1$–$C_4$)alkyl, most preferably 2-hydroxyethyl), carboxy(lower)alkyl (more preferably carboxy($C_1$–$C_4$)alkyl, most preferably carboxymethyl), lower alkoxycarbonyl(lower) alkyl (more preferably $C_1$–$C_4$ alkoxycarbonyl($C_1$–$C_4$) alkyl, most preferably tert-butoxycarbonylmethyl), morpholinyl(lower)alkyl (more preferably morpholinyl ($C_1$–$C_4$)alkyl, most preferably 2-morpholinoethyl) or morpholinylcarbonyl(lower)alkyl (more preferably morpholinylcarbonyl($C_1$–$C_4$)alkyl, most preferably morpholinocarbonylmethyl);

thiazolyl(lower)alkyl (more preferably thiazoly($C_1$–$C_4$) alkyl, most preferably 4-thiazolymethyl) which may have lower alkyl (more preferably $C_1$–$C_4$ alkyl, most preferably methyl);

piperidyl(lower)alkyl (more preferably piperidyl($C_1$–$C_4$) alkyl, most preferably piperidylethyl) which may have hydroxy(lower)alkyl (more preferably hydroxy($C_1$–$C_4$) alkyl, most preferably hydroxymethyl) or lower alkoxy (more preferably $C_1$–$C_4$ alkoxy, most preferably ethoxy);

morpholinyl(lower)alkyl (more preferably morpholinyl ($C_1$–$C_4$)alkyl, most preferably morpholinylethyl or morpholinylpropyl) which has 1 or 2 substituent(s) selected from the group consisting of ethyl, hydroxy (lower)alkyl (more preferably hydroxy($C_1$–$C_4$)alkyl, most preferably hydroxymethyl), halo(lower)alkyl (more preferably halo($C_1$–$C_4$)alkyl, most preferably fluoromethyl) and lower alkoxy(lower)alkyl (more preferably $C_1$–$C_4$ alkoxy($C_1$–$C_4$)alkyl, most preferably methoxymethyl);

morpholinyl(lower)alkyl (more preferably morpholinyl ($C_1$–$C_4$)alkyl, most preferably morpholinoethyl or morpholinopropyl) which has lower alkyl (more preferably $C_1$–$C_4$ alkyl, most preferably methyl) and lower alkoxy(lower)alkyl (more preferably $C_1$–$C_4$ alkoxy ($C_1$–$C_4$)alkyl, most preferably methoxymethyl);

(3,5-dimethylmorpholino)(lower)alkyl (more preferably (3,5-dimethylmorpholino)($C_1$–$C_4$)alkyl, most preferably (3,5-dimethylmorpholino)ethyl);

morpholino(lower)alkenyl (more preferably morpholino ($C_2$–$C_4$)alkenyl, most preferably 4-morpholino-2-butenyl) which may have lower alkyl (more preferably $C_1$–$C_4$ alkyl, most preferably isopropyl) or lower alkoxy(lower)alkyl (more preferably $C_1$–$C_4$ alkoxy ($C_1$–$C_4$)alkyl, most preferably methoxymethyl);

(2- or 3-morpholinyl)(lower)alkenyl (more preferably (2- or 3-morpholinyl)($C_2$–$C_4$)alkenyl, most preferably 3-(2- or 3-morpholinyl)-2-propenyl) which may have lower alkoxycarbonyl (more preferably $C_1$–$C_4$ alkoxycarbonyl, most preferably tert-butoxycarbonyl);

pyrrolidinyl(lower)alkynyl (more preferably pyrrolidinyl ($C_2$–$C_4$)alkynyl, most preferably 4-pyrrolidino-2-butynyl) which may have lower alkoxy(lower)alkyl (more preferably $C_1$–$C_4$ alkoxy($C_1$–$C_4$)alkyl, most preferably methoxymethyl);

morpholinyl(lower)alkynyl (more preferably morpholinyl ($C_2$–$C_4$)alkynyl, most preferably 4-morpholino-2-butynyl or 3-(3-morpholinyl)-2-propynyl) which may have 1 or 2 substituent(s) selected from the group consisting of ethyl, propyl, isopropyl, isobutyl, spirocyclo(lower)alkyl (more preferably spirocyclo ($C_3$–$C_6$)alkyl, most preferably spirocyclopropyl), lower alkoxy(lower)alkyl (more preferably $C_1$–$C_4$ alkoxy($C_1$–$C_4$)alkyl, most preferably methoxymethyl or ethoxymethyl), hydroxy(lower)alkyl (more preferably hydroxy($C_1$–$C_4$)alkyl, most preferably hydroxymethyl), carboxy(lower)alkyl (more preferably carboxy($C_1$–$C_4$)alkyl, most preferably carboxymethyl), di(lower)alkylcarbamoyl (more preferably di($C_1$–$C_4$) alkylcarbamoyl, most preferably dimethylcarbamoyl), lower alkoxycarbonyl (more preferably $C_1$–$C_4$ alkoxycarbonyl, most preferably ethoxycarbonyl) and halo(lower)alkyl (more preferably halo($C_1$–$C_4$)alkyl, most preferably fluoromethyl);

morpholinyl(lower)alkynyl (more preferably morpholinyl ($C_2$–$C_4$)alkynyl, most preferably 4-morpholino-2-butynyl) which has methyl and lower alkoxy(lower) alkyl (more preferably $C_1$–$C_4$ alkoxy($C_1$–$C_4$)alkyl, most preferably methoxymethyl);

(dimethylmorpholino)(lower)alkynyl (more preferably (dimethylmorpholino)($C_2$–$C_4$)alkynyl, most preferably 4-(3,3-dimethylmorpholino)-2-butynyl, 4-(2,6-dimethylmorpholino)-2-butynyl or 4-(3,5-dimethylmorpholino)-2-butynyl);

homomorpholinyl(lower)alkynyl (more preferably homomorpholinyl($C_2$–$C_4$)alkynyl, most preferably 4-homomorpholino-2-butynyl) which may have halogen (more preferably fluorine);

morpholinylaminopropyl (more preferably 3-(morpholinoamino)propyl) which may have lower alkanoyl (more preferably $C_1$–$C_4$ alkanoyl, most preferably formyl);

thiomorpholinyl(lower)alkynyl (more preferably thiomorpholinyl($C_2$–$C_4$)alkynyl, most preferably 4-thiomorpholino-2-butynyl);

homomorpholinylamino(lower)alkyl (more preferably homomorpholinylamino($C_1$–$C_4$)alkyl, more preferably homomorpholinoaminopropyl);

thiomorpholinylamino(lower)alkyl (more preferably thiomorpholinylamino($C_1$–$C_4$)alkyl, more preferably thiomorpholinoaminopropyl); or saturated heterocyclicimino(lower)alkyl (more preferably saturated heterocyclicimino($C_1$–$C_4$)alkyl, most preferably saturated heterocycliciminoethyl), saturated heterocyclicaminocarbonyl(lower)alkyl (more preferably saturated heterocyclicaminocarbonyl($C_1$–$C_4$) alkyl, most preferably saturated heterocyclicaminocarbonylmethyl) or saturated heterocyclic(lower) alkoxy(lower)alkyl (more preferably saturated heterocyclic($C_1$–$C_4$)alkoxy($C_1$–$C_4$)alkyl, most preferably saturated heterocyclicethoxyethyl) [wherein "saturated heterocyclic" moiety is saturated 3 to 8-membered (more preferably 5 to 7-membered) heteromonocyclic group containing 1 to 4 (more preferably 1 or 2) nitrogen atom(s) (more preferably pyrrolidinyl, piperidyl or piperazinyl);

saturated 3 to 8-membered (more preferably 5 to 7-membered) heteromonocyclic group containing 1 or 2 (more preferably 1) oxygen atom(s) and 1 to 3 (more preferably 1) nitrogen atom(s) (more preferably morpholinyl or homomorpholinyl);

saturated 3 to 8-membered (mote preferably 5 or 6-membered) heteromonocyclic group containing 1 or 2 (more preferably 1) sulfur atom(s) and 1 to 3 (more preferably 1) nitrogen atom(s) (more preferably thiomorpholinyl);
or saturated heterocyclic group of the formula:

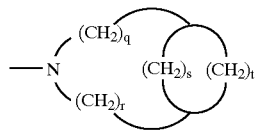

(wherein q, r, s and t are each as defined above)
(more preferably 3-azabicyclo[3.2.2]non-3-yl)], each of which may have 1 to 3 (more preferably 1 or 2) suitable substituent(s) [more preferably substituent selected from the group consisting of cyclo(lower)alkyl (more preferably cyclohexyl), lower alkanoyl (more preferably $C_1-C_4$ alkanoyl, most preferably formyl), lower alkyl (more preferably $C_1-C_4$ alkyl, most preferably methyl, ethyl, isopropyl or isobutyl), mono(or di or tri)halo(lower)alkyl (more preferably monohalo($C_1-C_4$)alkyl or trihalo($C_1-C_4$)alkyl, most preferably fluoromethyl or trifluoromethyl), lower alkoxy (more preferably $C_1-C_4$ alkoxy, most preferably methoxy), lower alkoxy(lower)alkyl (more preferably $C_1-C_4$ alkoxy($C_1-C_4$)alkyl, most preferably methoxymethyl), halogen (more preferably chlorine or fluorine), aryl (more preferably phenyl), cyano, oxo, bivalent group of the formula:

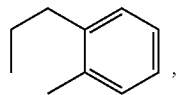

carboxy(lower)alkyl (more preferably carboxy($C_1-C_4$) alkyl, most preferably carboxypropyl), lower alkoxycarbonyl (more preferably $C_1-C_4$ alkoxycarbonyl, most preferably tert-butoxycarbonyl), spirocyclo (lower)alkyl (more preferably spirocyclo($C_1-C_4$)alkyl, most preferably spirocyclopropyl), ar(lower) alkoxycarbonyl(lower)alkyl (more preferably benzyloxycarbonyl($C_1-C_4$)alkyl, most preferably benzyloxycarbonylpropyl), hydroxy(lower)alkyl (more preferably hydroxy($C_1-C_4$)alkyl, most preferably hydroxymethyl), carbamoyl, lower alkylcarbamoyl (more preferably $C_1-C_4$ alkylcarbamoyl, most preferably methylcarbamoyl) and di(lower alkyl)carbamoyl (more preferably di($C_1-C_4$ alkyl)carbamoyl, most preferably dimethylcarbamoyl)].

More preferred embodiments of the object compound (I) are as follows:
Y is lower alkylene (more preferably $C_1-C_4$ alkylene, most preferably methylene);
$R^1$ is phenyl which may have 1 or 2 substituent(s) selected from the group consisting of mono(or di or tri)halo(lower) alkyl, halogen (more preferably chlorine), lower alkylamino, di(lower)alkylamino and nitro [more preferably bis(trihalo(lower)alkyl)phenyl or dichlorophenyl, most preferably bis(trifluoromethyl)phenyl];
$R^2$ is phenyl which may have 1 or 2 substituent(s) selected from the group consisting of lower alkyl, mono(or di or tri)halo(lower)alkyl, lower alkylenedioxy, hydroxy, hydroxy(lower)alkyl, lower alkoxy, lower alkylamino and di(lower)alkylamino [more preferably di(lower alkyl) phenyl or [trihalo(lower)alkyl]phenyl, most preferably dimethylphenyl or (trifluoromethyl)phenyl], naphthyl or indolyl;

$R^3$ is hydrogen; and
$R^4$ is pyridyl(lower)alkylamino(lower)alkynyl (more preferably pyridyl($C_1-C_4$)alkylamino($C_2-C_4$)alkynyl, most preferably 4-[(3-pyridylmethyl)amino]-2-butynyl) or (2-pyridyl)(lower)alkyl (more preferably (2-pyridyl) ($C_1-C_4$)alkyl, more preferably (2-pyridyl)propyl or (2-pyridyl)butyl, most preferably 3-(2-pyridyl)propyl.

Another more preferred embodiments of the object compound (I) are as follows:
Y is lower alkylene,
$R^1$ is $C_6-C_{10}$ aryl which may have 1 or 2 mono(or di or tri)halo(lower)alkyl;
$R^2$ is $C_6-C_{10}$ aryl or indolyl, each of which may have 1 to 3 substituent(s) selected from the group consisting of lower alkyl, mono(or- di or tri)halo(lower)alkyl, lower alkylenedioxy, hydroxy, hydroxy(lower)alkyl, lower alkoxy, lower alkylamino and di(lower)alkylamino,
$R^3$ is hydrogen, and
$R^4$ is pyridyl(lower)alkylamino(lower)alkynyl;
(2-pyridyl)propyl which may have 1 to 3 substituent(s) selected from the group consisting of lower alkyl, lower alkoxy, mono(or di or tri)halo(lower)alkyl and halogen;
pyridyl, thiazolyl, imidazolyl or pyrazolyl, each of which may have 1 or 2 substituent(s) selected from the group consisting of lower alkyl, ar(lower)alkyl and pyridyl (lower)alkyl;
imidazolyl(lower)alkyl which has 1 or 2 substituent(s) selected from the group consisting of lower alkynyl, ar(lower)alkyl, pyridyl(lower)alkyl, mono(or di or tri)halo(lower)alkyl and halogen;
(2-methyl-1H-imidazol-4-yl)(lower)alkyl which has 1 or 2 substituent(s) selected from the group consisting of isopropyl, lower alkynyl, ar(lower)alkyl, pyridyl (lower)alkyl, mono(or di or tri)halo(lower)alkyl and halogen;
(5-methyl-1H-imidazol-4-yl)(lower)alkyl which has 1 or 2 substituent(s) selected from the group consisting of isopropyl, lower alkynyl, ar(lower)alkyl, pyridyl (lower)alkyl, mono(or di or tri)halo(lower)alkyl and halogen;
piperidyl(lower)alkyl which may have hydroxy(lower) alkyl or lower alkoxy;
morpholinyl(lower)alkyl which has 1 or 2 substituent(s) selected from the group consisting of ethyl, hydroxy (lower)alkyl, halo(lower)alkyl and lower alkoxy (lower)alkyl;
morpholinyl(lower)alkyl which has lower alkyl and lower alkoxy(lower)alkyl;
(3,5-dimethylmorpholino)(lower)alkyl;
morpholino(lower)alkenyl which may have lower alkyl or lower alkoxy(lower)alkyl;
(2- or 3-morpholinyl)(lower)alkenyl which may have lower alkoxycarbonyl;
pyrrolidinyl(lower)alkynyl which may have lower alkoxy (lower)alkyl;
morpholinyl(lower)alkynyl which may have 1 or 2 substituent(s) selected from the group consisting of ethyl, propyl, isopropyl, isobutyl, spirocyclo(lower) alkyl, lower alkoxy(lower)alkyl, hydroxy(lower)alkyl, carboxy(lower)alkyl, di(lower alkyl)carbamoyl, lower alkoxycarbonyl and halo(lower)alkyl;
morpholinyl(lower)alkynyl which has methyl and lower alkoxy(lower)alkyl;

(dimethylmorpholino)(lower)alkynyl; or homomorpholinyl(lower)alkynyl which may have halogen.

The Processes 1 to 6 for preparing the object compound (I) of the present invention are explained in detail in the following.

Process 1

The object compound (I) or a salt thereof can be prepared by reacting the compound (II) or its reactive derivative at the imino group or a salt thereof with the compound (IV) or a salt thereof.

Suitable reactive derivative at the imino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsilyl)acetamide, bis(trimethylsilyl)urea or the like; a derivative formed by reaction of the compound (II) with phosphorus trichloride or phosgene and the like.

The reaction is usually carried out in a conventional solvent such as water, alcohol [e.g. methanol, ethanol, etc.], acetone, dioxene, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

The reaction may also be carried out in the presence of an inorganic or organic base such as alkali metal carbonate, alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to heating.

Process 2

The object compound (Ib) or a salt thereof can be prepared by subjecting the compound (Ia) or a salt thereof to a reduction reaction.

The reaction can be carried out in the manner disclosed in Example 3 mentioned later or similar manners thereto.

Process 3

The object compound (Ic) or a salt thereof can be prepared by reacting the compound (III) or its reactive derivative at the carboxy group or a salt thereof with the compound (V) or its reactive derivative at the amino group or a salt thereof.

Suitable reactive derivative at the carboxy group of the compound (III) may include an acid halide, an acid anhydride, an activated amide, an activated ester, and the like. The suitable example of the reactive derivative may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, lower alkanesulfonic acid [e.g. methanesulfonic acid, ethanesulfonic acid, etc.], sulfurous acid, thiosulfuric acid, sulfuric acid, aliphatic carboxylic acid [e.g. acetic acid, propionic acid, butyric acid, isobutyric acid, pivalic acid, valeric acid, isovaleric acid, 2-ethylbutyric acid, trichloroacetic acid, etc.] or aromatic-carboxylic acid [e.g. benzoic acid, etc.]; a symmetrical and anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (III) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

In this reaction, when the compound (III) is used in a free acid form or a salt thereof, the reaction is preferably carried out in the presence of a conventional condensing agent such as N,N'-dichlorohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thienyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)-isoxazolium hydroxide intramolecular salt; 1-(p-chlorobenzenesulfonyloxy)-6-chloro-1H-benzotriazole; 2-chloro-1-methylpyridinium iodide; 1-(3-dimethylaminopropyl)-3-ethylcarbodiimide hydrochloride; so-called vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as alkali metal carbonate, alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 4

The object compound (Id) or a salt thereof can be prepared by reacting the compound (VI) or a salt thereof with the compound (VII) or a salt thereof.

The reaction can be carried out in the manner disclosed in Example 30 mentioned later or similar manners thereto.

Process 5

The object compound (Ie) or a salt thereof can be prepared by reacting the compound (VIII) or a salt thereof with the compound (IX) or a salt thereof.

The reaction can be carried out in the manner disclosed in Example 35 mentioned later or similar manners thereto.

Process 6

The object compound (If) or a salt thereof can be prepared by reacting the compound (X) or a salt thereof with the compound (XI) or a salt thereof.

The reaction can be carried out in the manner disclosed in Example 8 mentioned later or similar manners thereto.

The object compound (I) and a pharmaceutically acceptable salt thereof have pharmacological activities such as Tachykinin antagonism, especially Substance P antagonism, Neurokinin A antagonism or Neurokinin B antagonism, and therefore are useful for treating or preventing Tachykinin-mediated diseases, particularly Substance P-mediated diseases, for example, respiratory diseases such as asthma, bronchitis (e.g. chronic bronchitis, acute bronchitis and diffuse panbronchiolitis, etc.), rhinitis, couph, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g. migraine, headache, cluster headache, toothache, cancerous pain, back pain, neuralgia, etc.); and the like.

Further, it is expected that the object compound (I) and a pharmaceutically acceptable salt thereof of the present invention are useful for treating or preventing ophthalmic diseases such as glaucoma, uveitis, and the like; gastrointestinal diseases such as ulcer, ulcerative colitis, irritable bowel syndrome, food allergy, and the like; inflammatory diseases such as nephritis, and the like; circulatory diseases such as hypertension, angina pectoris, cardiac failure, thrombosis, Raynaud's disease, and the like; epilepsy; spastic paralysis; pollakiuria; cystitis; bladder detrusor hyperreflexia; urinary incontinence; Parkinson diseases; dementia; AIDS related dementia; Alzheimer's diseases; Down's syndrome; Huntington's chorea; carcinoid syndrome; disorders related to immune enhancement or suppression; disorders caused by *Helicobacter pylori* or another spiral urease-positive gram-negative bacterium; sunburn; angiogenesis or diseases caused by angiogenesis; and the like.

It is furthermore expected that the object compound (I) and a pharmaceutically acceptable salt thereof of the present invention are useful for treating or preventing chronic obstructive pulmonary diseases, particularly chronic pulmonary emphysema; iritis; proliferative vitreoretinopathy; psoriasis; inflammatory intestinal diseases, particularly Crohn's diseases; hepatitis; superficial pain on congelation, burn, herpes zoster or diabetic neuropathy; tenalgia attended to hyperlipidemia; postoperative neuroma, particularly of mastectomy; vulvar vestibulitis; hemodialysis-associated itching; lichen planus; laryngopharyngitis; bronchiectasis; coniosis; whooping cough; pulmonary tuberculosis; cystic fibrosis; emesis (e.g. nausea, retching, vomiting, acute emesis, delayed emesis, anticipatory emesis, post operative nausea and vomiting (PONV), acute and/or delayed emesis induced by drugs such as cancer chemotherapeutic agents, etc.); mental diseases, particularly anxiety, depression, dysthymic disorders and schizophrenia; demyelinating diseases such as multiple sclerosis and amyotrophic lateral sclerosis; attenuation of morphine withdrawal; oedema, such as oedema caused by thermal injury; small cell carcinomas, particularly small cell lung cancer (SCLC); hypersensitivity disorders such as poison ivy; fibrosing and collagen diseases such as scleroderma and eosinophilic fascioliasis; reflex sympathetic dystrophy such as shoulder/hand syndrome; addiction disorders such as alcoholism; stress related somatic disorders; rheumatic diseases such as fibrositis; and the like.

Furthermore, the object compound (I) and a pharmaceutically acceptable salt thereof of the present invention are Central Nervous System (CNS) penetrant.

For therapeutic purpose, the compound (I) and a pharmaceutically acceptable salt thereof of the present invention can be used in a form of pharmaceutical preparation containing one of said compound, as an active ingredient, in admixture with a pharmaceutically acceptable carrier such as an organic or inorganic solid or liquid excipient suitable for oral, parenteral, external including topical, enternal, intravenous, intramuscular, inhalant, nasal, intraarticular, intraspinal, transtracheal or transocular administration. The pharmaceutical preparations may be solid, semi-solid or solutions such as capsules, tablets, pellets, dragees, powders, granules, suppositories, ointments, creams, lotions, inhalants, injections, cataplasms; gels, tapes, eye drops, solution, syrups, aerosols, suspension, emulsion, or the like. If desired, there may be included in these preparations, auxiliary substances, stabilizing agents, wetting or emulsifying agents, buffers and other commonly used additives.

While the dosage of the compound (I) will vary depending upon the age and condition of a patient, an average single dose of about 0.1 mg, 1 mg, 10 mg, 50 mg, 100 mg, 250 mg, 500 mg and 1000 mg of the compound (I) may be effective for treating Tachykinin-mediated diseases such as asthma and the like. In general, amounts between 0.1 mg/body and about 1,000 mg/body may be administered per day.

In order to show the utility of the object compound (I) and a pharmaceutically acceptable salt thereof, the pharmacological test data of some representative compounds of the present invention is shown in the following.

A. Evaluation of $NK_1$ Antagonist Transport Efficiency to the Cental Nervous System using a h-$NK_1$ Receptor Binding Assay

[I] Test Method (1) Administration of Test Compound and Extraction of the Compound from Brain Male SD rats were given an i.v. injection of a solution containing a test compound (1 mg/kg). 5 Min later the animals were anesthetized by ether, bled and perfused through the aorta ascendens with 20 ml of saline. The brain was rapidly removed, weighed and homogenized in 4 vol. ice-cold distilled water by using Polytoron (KINEMATICA). To extract the test compound, 500 µl of the homogenate, 100 µl of methanol, 500 µl of 0.1 N NaOH and 4 ml of ethyl acetate were mixed by shaking for 10 min at room temperature. The organic phase (2.5 ml) was recovered by centrifugation at 3,000 rpm for 10 min, dried and dissolved in dimethyl sulfoxide.

(2) h-$NK_1$ Receptor Binding Assay (a) Crude CHO Cell Membrane Preparation

CHO cells permanently expressing h-$NK_1$ receptors were harvested and homogenized with a Dounce homogenizer at 4° C. in a buffer (0.25 M sucrose, 25 mM Tris-HCl (pH 7.4), 10 mM $MgCl_2$, 1 mM EDTA, 5 µg/ml p-APMSF). The homogenate was centrifuged (500×g, 10 min), and the pellet was resuspended in the same buffer, homogenized, and centrifuged. The two supernatants were combined and centrifuged (100,000×g, 1 hour). The crude cell membranes thus isolated were resuspended in a buffer (25 mM Tris-HCl (pH 7.4), 10 mM $MgCl_2$, 1 mM. EDTA, 5 µg/ml p-APMSF) and stored at −80° C. until use.

(b) $^{125}$I-BH-Substance P Binding to the Prepared Membrane

Cell membranes (6 µg/ml) were incubated with $^{125}$I-BH-Substance P (0.1 nM) with or without the extracted compounds in 0.25 ml of a medium (50 mM Tris-HCl (pH 7.4), 5 mM $MnCl_2$, 20 µg/ml chymostatin, 40 µg/ml bacitracin, 4 µg/ml leupeptin, 5 µg/ml p-APMSF, 200 µg/ml BSA) at 22° C. for 90 min. At the end of the incubation period, the contents were quickly filtered through a Blue Mat 11740 filter (pretreated with 0.1% polyethylenimine for 3 hours prior to use) by using SKATRON Cell Harvester. The filter was then washed with a washing buffer (50 mM Tris-HCl (pH 7.4), 5 mM $MnCl_2$). The radioactivity was counted by using an auto gamma counter (Packard RIASTAR 5420A). All data presented are specific binding defined as that displaceable by 3 µM unlabeled Substance P.

[II] Test Result

All of the following Test Compounds showed more than 80% inhibition rate of $^{125}$I-BH-Substance P binding to h-$NK_1$ receptors at the dose of 1 mg/kg.

Test Compounds: The object compounds of the Examples 1-(1), 5-(2), 6-(1), 15, 16-(2), 17, 18, 22, 29, 30, 38, 40, 45, 56-(2), 68, 70-(1), 70-(2), 71-(1), 71-(3), 71-(5), 71-(6), 73-(2), 73-(3), 76-(1), 76-(3), 77, 78-(3), 78-(4), 79-(1), 79-(2), 80-(1), 80-(2), 80-(3), 80-(4), 80-(6), 80-(7), 81-(1), 81-(2), 81-(3), 81-(4), 81-(5), 81-(7), 81-(10), 82, 83-(2), 84, 85-(3), 89-(1), 89-(2), 90-(2), 90-(3), 90-(4), 90-(5) and 90-(6)

B. Emesis in the Ferret

[I] Test Method

Individually housed adult male ferrets (Marshall Farms, 1.4 to 2.2 kg) were given an i.v. injection of a solution contatining a test compound. 30 Min later the emetic responses (retching and vomiting) were induced by administration of intra-gastric copper sulfate (40 mg/kg/ml) and observed for the next 30 min. The timing and number of retches and vomits observed were recorded for each animal. An individual animal was tested with at least 10 days between experiments.

[II] Test Result

All of the following Test Compounds showed 100% inhibition rate of emesis in the ferret at the dose of 1.0 mg/kg.

Test compounds: The object compounds of the Examples 4-(2), 26, 29, 40 and 41 (to be continued on the next page)

The following Preparations and Examples are given for the purpose of illustrating this invention.

Preparation 1

A mixture of 3-bromopyridine (6.25 ml), propargyl alcohol (4.9 ml), bis(triphenylphosphine)palladium(II) chloride (0.45 g) and copper iodide (125 mg) in triethylamine (100 ml) was stirred under reflux for 1.5 hours. After being cooled at room temperature, the reaction mixture was filtered and the insoluble material on the filter was washed with ethyl acetate (about 200 ml). The filtrate and the washing were combined and evaporated under reduced pressure. The resulting residue was purified by column chromatography on silica gel using a mixed solvent of hexane and ethyl acetate as eluent. The fractions containing the objective compound were collected and evaporated under reduced pressure to give 3-(3-pyridyl)-2-propyn-1-ol (7.9 g) as brownish crystals.

IR (Nujol): 3160, 1480, 1460, 1400 $cm^{-1}$ NMR ($CDCl_3$, δ): 3.87 (1H, t, J=5.9 Hz), 4.51 (2H, d, J=5.9 Hz), 7.24–7.30 (1H, m), 7.73 (1H, dd, J=1.9 and 7.4 Hz), 8.52 (1H, d, J=5.1 Hz), 8.78 (1H, d, J=1.9 Hz) MASS: 134 $(M+H)^+$ Preparation 2

The following compounds were obtained according to a similar manner to that of Preparation 1.

(1) 4-(3-Pyridyl)-3-butyn-1-ol

NMR ($CDCl_3$, δ): 2.61 (1H, s), 2.71 (2H, t, J=6.3 Hz), 3.85 (2H, t, J=6.3 Hz), 7.19–7.25 (1H, m), 7.70 (1H, dd, J=2.0, 8.0 Hz), 8.48 (1H, dd, J=1.4, 5.0 Hz), 8.63 (1H, d, J=1.4 Hz) MASS: 279, 148 $(M+H)^+$ (2) 3-(6-Methoxypyridin-3-yl)-2-propyn-1-ol IR (Nujol): 3300, 1610, 1560, 1490, 1460, 1370, 1350, 1310, 1300 $cm^{-1}$ NMR ($CDCl_3$, δ): 3.94 (3H, s), 4.52 (2H, s), 6.70 (1H, d, J=0.7, 8.6 Hz), 7.60 (1H, dd, J=2.2, 8.6 Hz), 8.30 (1H, d, J=2.2 Hz) MASS: 164 $(M+H)^+$, 134

(3) 3-(4-Methoxypyridin-3-yl)-2-propyn-1-ol

IR (KBr): 3172, 2854, 1585, 1498 $cm^{-1}$ NMR ($CDCl_3$, δ): 3.90 (3H, s), 4.33 (2H, d, J=4.0 Hz), 5.38 (1H, t, J=4.0 Hz), 7.12 (1H, d, J=5.8 Hz), 8.24 (2H, br s) MASS: 164 $(M+H)^+$, 134

(4) 3-[6-(tert-Butoxycarbonylamino)pyridin-3-yl]-2-propyn-1-ol

IR (Nujol): 3500, 3210, 1725, 1625, 1600, 1580, 1430, 1380 $cm^{-1}$ NMR ($CDCl_3$, δ): 1.54 (9H, s), 4.99 (2H, s), 7.70 (1H, dd, J=2.2, 8.7 Hz), 7.97 (1H, d, J=8.7 Hz), 8.40 (1H, d, J=2.2 Hz), 8.51 (1H, br s) MASS: 217 $(M+H)^+$, 175

Preparation 3

Thionyl chloride (11.9 g) was added dropwise to a solution of 3-(3-pyridyl)-2-propyn-1-ol (13.3 g) in dichloromethane (266 ml) at room temperature. After completion of the addition, the mixture was stirred for 2 hours at room temperature. The resulting precipitates were collected by filtration and washed with diethyl ether to give 1-chloro-3-(3-pyridyl)-2-propyne hydrochloride (14.5 g) as brownish crystals.

Preparation 4

The following compounds were obtained according to a similar manner to that of Preparation 3.

(1) 1-Chloro-3-(6-methoxypyridin-3-yl)-2-propyne hydrochloride (2) 1-Chloro-3-(4-methoxypyridin-3-yl)-2-propyne hydrochloride Preparation 5

Isobutyl chloroformate (4.4 ml) was added dropwise to a suspension of (E)-3-(3-pyridyl)acrylic acid (5.0 g) and N-methylmorpholine (4.05 ml) in 1,2-dimethoxyethane (50 ml) under −18° C. After being stirred at the same temperature for 0.5 hour, a solution of sodium borohydride (1.86 g) in water (10 ml) was added to the mixture all at once. The resulting mixture was poured into water and extracted with ethyl acetate. The extract was washed with brine and dried over magnesium sulfate, and evaporated under reduced pressure. The residue was purified by column chromatography on silica gel using a mixed solvent of hexane and ethyl acetate as eluent. The fractions containing the objective compound were collected and evaporated under reduced pressure to give (E)-3-(3-pyridyl)-2-propen-1-ol (1.0 g) as an oil.

NMR ($CDCl_3$, δ): 4.40 (2H, d, J=4.0 Hz), 6.52 (1H, dt, J=4.0, 16.1 Hz, trans), 6.65 (1H, d, J=16.1 Hz, trans), 7.45 (1H, dd, J=5.6, 8.0 Hz), 7.89 (1H, d, J=8.0 Hz), 8.44 (1H, d, J=5.6 Hz), 8.58 (1H, s) MASS: 136 $(M+H)^+$ Preparation 6

Methane sulfonyl chloride (0.22 ml) was added to a mixture of (E)-3-(3-pyridyl)-2-propen-1-ol (0.36 g) and triethylamine (0.74 ml) in dichloromethane (5 ml) under −10° C. After being stirred at the same temperature for 0.5 hour, the reaction mixture was washed with saturated sodium bicarbonate, dried over magnesium sulfate and evaporated under reduced pressure to give (E)-3-(3-pyridyl)-2-propen-1-yl methanesulfonate.

The crude mesylate was used at next step without further purification.

Preparation 7

4-(3-Pyridyl)-3-butyn-1-yl methanesulfonate was obtained according to a similar manner to that of Preparation 6.

Preparation 8

The solution of 3-(3-pyridyl)-2-propyl-1-ol (300 mg) in methanol was hydrogenated using Lindlar catalyst for 4 hours at atmospheric pressure. After removal of catalyst by filtration, the filtrate was concentrated under reduced pressure. The residue was purified by column chromatography on silica gel using ethyl acetate as eluent. The fractions containing the objective compound were collected and evaporated under reduced pressure to give (Z)-3-(3-pyridyl)-2-propen-1-ol (50 mg) as an oil.

IR (Nujol): 3600–2700, 1590, 1575, 1480 cm$^{-1}$ NMR (CDCl$_3$, δ): 4.42 (2H, dd, J=1.6, 6.4 Hz), 6.04 (1H, dd, J=6.4, 12.0 Hz, cis), 6.52 (1H, d, J=12.0 Hz, cis), 7.25–7.31 (1H, m), 7.55 (1H, d, J=8.0 Hz), 8.30–8.70 (2H, br s) MASS: 136 (M+H)$^+$ Preparation 9

A mixture of 4-formyl-1-methylimidazole (3.0 g) and triethylphosphonoacetate (6.3 g) in N,N-dimethylformamide (30 ml) was stirred under ice-cooling. After several minutes, sodium hydride (1.63 g, 60% in mineral oil) was added to the mixture, which was stirred for 30 minutes at the same temperature. The resulting mixture was poured into ice-water, neutralized with aqueous ammonium acetate solution and extracted with ethyl acetate. The organic layer was washed with brine, dried over magnesium sulfate and concentrated under reduced pressure to give ethyl (E)-3-(1-methyl-1H-imidazol-4-yl)acrylate (4.63 g).

IR (Nujol): 2900, 1700, 1625 cm$^{-1}$ NMR (CDCl$_3$, δ): 1.31 (3H, t, J=7.1 Hz), 3.70 (3H, s), 4.23 (2H, q, J=7.1 Hz), 6.53 (1H, d, J=15.6 Hz), 7.07 (1H, s), 7.45 (1H, s), 7.54 (1H, d, J=15.6 Hz) MASS: 181 (M+H)$^+$ Preparation 10

A solution of ethyl (E)-3-(1-methyl-1H-imidazol-4-yl) acrylate (2.5 g) in tetrahydrofuran (100 ml) was hydrogenated over 10% palladium activated carbon (0.2 g) at room temperature under 2 atmospheric pressure. After removal of catalyst by filtration through Celite pad, the filtrate was concentrated under reduced pressure to give ethyl 3-(1-methyl-1H-imidazol-4-yl)propionate (2.63 g).

IR (Neat): 2900, 1720 cm$^{-1}$ NMR (CDCl$_3$, δ): 1.24 (3H, t, J=7.1 Hz), 2.62 (2H, t, J=7.4 Hz), 2.89 (2H, t, J=7.4 Hz), 3.62 (3H, s), 4.16 (2H, q, J=7.1 Hz), 6.64 (1H, s), 7.33 (1H, s) MASS: 183 (M+H)$^+$ Preparation 11

To an ice-cooled solution of ethyl 3-(1-methyl-1H-imidazol-4-yl)propionate (2.63 g) in tetrahydrofuran (26 ml) was added lithium aluminum hydride (0.55 g) by small-portions under nitrogen atmosphere. After the mixture was stirred for 0.5 hour, water and 15% aqueous sodium hydroxide solution were added successively to the mixture. The resulting precipitates were filtrated off through Celite pad and the filtrate was extracted with ethyl acetate. The organic layer was washed with water and brine successively, dried over magnesium sulfate and concentrated under reduced pressure. The resulting residue was purified by column chromatography on silica gel using dichloromethane-methanol (100:1) as eluent to give 3-(1-methyl-1H-imidazol-4-yl)-1-propanol (940 mg).

IR (Neat): 3250, 2900 cm$^{-1}$ NMR (CDCl$_3$, δ): 1.86 (2H, m), 2.69 (2H, t, J=6.7 Hz), 3.63 (3H, s), 3.73 (2H, t, J=6.0 Hz), 6.62 (1H, s), 7.34 (1H, s) MASS: 141 (M+H)$^+$ Preparation 12

To a solution of oxalyl chloride (0.361 ml) in dichloromethane (10 ml) cooled below −65° C. with a dry ice-acetone bath, a solution of dimethyl sulfoxide (0.381 ml) in dichloromethane (1 ml) was added with efficient stirring over 10 minutes. After 20 minutes below −65° C., a solution of 3-(1-methyl-1H-imidazol-4-yl)-1-propanol in dichloromethane (2 ml) was added to the mixture over 10 minutes below −65° C. and the mixture was stirred at the same temperature for 20 minutes and then at −45° C.~−40° C. for 30 minutes. After addition of triethylamine (1.0 ml) dropwise to the mixture over 1 minute followed by stirring for 30 minutes, the reaction mixture was concentrated in vacuo. The resulting residue was purified by column chromatography on silica gel using dichloromethane-methanol (20:1) as eluent to give 3-(1-methyl-1H-imidazol-4-yl)propanol (103 mg).

IR (Neat): 1715 cm$^{-1}$ NMR (CDCl$_3$, δ): 2.85 (4H, m), 3.63 (3H, s), 6.63 (1H, s), 7.34 (1H, s), 9.83 (1H, s) MASS: 139 (M+H)$^+$ Preparation 13

The following compound was obtained according to a similar manner to that of Preparation 12.

4-Formyl-1-(triphenylmethyl)pyrazole

NMR (DMSO-d$_6$, δ): 7.05–7.10 (6H, m), 7.36–7.41 (9H, m), 8.15 (2H, s), 9.81 (1H, s)

Preparation 14

To a solution of (3R)-4-benzyl-3-(hydroxymethyl)-morpholine (13.67 g) in methanol (140 ml) and water (10 ml) was added ammonium formate (10.4 g) and palladium on activated carbon (50%, 1.4 g). The resulting mixture was stirred at 60° C. for 3 hours. After removal of insoluble material by filtration, the filtrate was concentrated under reduced pressure to give crude amine (16.43 g). To a solution of the obtained amine in tetrahydrofuran (160 ml) were added triethylamine (32.2 ml) and di-tert-butyl dicarbonate (50.4 g) at 0° C. After stirring at room temperature for 12 hours, the mixture was quenched with water and extracted with ethyl acetate three times. The organic layer was washed with brine, dried over magnesium sulfate, and evaporated under reduced pressure to give crude oil which was purified by column chromatography on a silica gel using a mixture of ethyl acetate and hexane (6:4) as eluent to give (3R)-4-(tert-butoxycarbonyl)-3-(hydroxymethyl) morpholine (8.64 g) as a colorless solid.

NMR (CDCl$_3$, δ): 1.47 (9H, s), 3.16–3.24 (1H, m), 3.40–3.61 (2H, m), 3.71–4.00 (6H, m)

Preparation 15

The following compound was obtained according to a similar manner to that of Preparation 14.

(2R,2S)-4-(tert-Butoxycarbonyl)-2-(hydroxymethyl) morpholine

IR (Neat): 1695 cm$^{-1}$ NMR (CDCl$_3$, δ): 1.47 (9H, m), 2.03 (1H, t, J=6.7 Hz), 2.70–3.00 (2H, m), 3.45–3.74 (4H, m), 3.84–3.95 (3H, m)

Preparation 16

The following compounds were obtained according to a similar manner to that of Preparation 12.

(1) (3S)-4-(tert-Butoxycarbonyl)-3-formylmorpholine

IR (KBr): 1734, 1695 cm$^{-1}$ NMR (CDCl$_3$, δ): 1.47 (9H, s), 3.00–3.30 (1H, m), 3.48 (1H, dt, J=2.8, 11.7 Hz), 3.67 (1H, dt, J=4.2, 12.1 Hz), 3.60–3.90 (2H, m), 4.25–4.50 (2H, m), 9.66 (1H, s)

(2) (2R,2S)-4-(tert-Butoxycarbonyl)-2-formylmorpholine

IR (Neat): 1737, 1681 cm$^{-1}$ NMR (CDCl$_3$, δ): 1.47 (9H, m), 2.80–5.00 (7H, m), 9.65 (1H, m)

Preparation 17

The following compounds were obtained according to a similar manner to that of Preparation 9.

(1) Ethyl (2E)-3-[(3R)-4-(tert-butoxycarbonyl)morpholin-3-yl]acrylate

IR (Neat): 2978, 1716, 1697 cm$^{-1}$ NMR (CDCl$_3$, δ): 1.26 (3H, t, J=7.4 Hz), 1.46 (9H, s), 3.16 (1H, dt, J=3.7, 13.2 Hz), 3.49 (1H, dt, J=2.9, 11.9 Hz), 3.69 (1H, dd, J=3.6, 11.7 Hz), 3.80–3.99 (3H, m), 4.21 (2H, q, J=7.1 Hz), 4.50–4.60 (1H, m), 5.93 (1H, dd, J=1.8, 15.9 Hz), 6.99 (1H, dd, J=5.3, 15.9 Hz)

(2) Ethyl (2E)-3-[(2R,2S)-(4-tert-butoxycarbonyl)morpholin-2-yl]acrylate

IR (Neat): 1737, 1681 cm$^{-1}$ NMR (CDCl$_3$, δ): 1.27 (3H, t, J=3.3 Hz), 1.47 (9H, s), 2.30–3.10 (3H, m), 3.57 (1H, dt, J=2.7, 11.3 Hz), 3.80–4.20 (3H, m), 4.21 (2H, q, J=7.1 Hz), 6.12 (1H, dd, J=1.7, 15.8 Hz), 6.83 (1H, dd, J=4.2, 15.8 Hz)

Preparation 18

To a solution of ethyl (2E)-3-[(3R)-4-(tert-butoxycarbonyl)morpholin-3-yl]acrylate (1.0 g) in toluene (10 ml) was added diisobutylaluminum hydride (1.02 M in toluene, 7.6 ml) at −78° C.~−40° C. After stirring for 2 hours at 0° C., the mixture was quenched with methanol (1.2 ml), and stirred for 1 hour at room temperature. After the resulting precipitate was filtered off, the filtrate was evaporated and purified by column chromatography on a silica gel using a mixture of ethyl acetate and hexane (3:7~4:6) as eluent to give (3R)-4-(tert-butoxycarbonyl)-3-[(E)-3-hydroxy-1-propenyl]morpholine (0.71 g) as a colorless oil.

IR (Neat): 1691 cm$^{-1}$ NMR (CDCl$_3$, δ): 1.47 (9H, s), 3.17 (1H, dt, J=3.7, 12.2 Hz), 3.48 (1H, dt, J=2.7, 11.3 Hz), 3.65 (1H, dd, J=3.4, 11.6 Hz), 3.70–3.91 (3H, m), 4.17–4.19 (2H, m), 4.40–4.50 (1H, m), 5.82–5.93 (2H, m)

Preparation 19

The following compound was obtained according to a similar manner to that of Preparation 18.

(2R,2S)-4-(tert-Butoxycarbonyl)-2-[(E)-3-hydroxy-1-propenyl]morpholine

NMR (CDCl$_3$, δ): 1.47 (9H, s), 2.62–3.00 (2H, m), 3.56 (1H, dt, J=2.7, 11.4 Hz), 3.81–3.94 (4H, m), 4.18 (2H, d, J=5.0 Hz), 5.64–6.04 (2H, m)

Preparation 20

The following compounds were obtained according to a similar manner to that of Preparation 6.

(1) (3R)-4-(tert-Butoxycarbonyl)-3-[(E)-3-methanesulfonyloxy-1-propenyl]morpholine NMR (CDCl$_3$, δ): 1.47 (9H, s), 3.02 (3H, s), 3.10–3.25 (1H, m), 3.48 (1H, dt, J=2.8, 11.5 Hz), 3.63–3.93 (4H, m), 4.45–4.55 (1H, m), 4.74 (2H, d, J=6.2 Hz), 5.75–5.86 (1H, m), 6.05 (1H, dd, J=5.5, 15.6 Hz)

(2) (2R,2S)-4-(tert-Butoxycarbonyl)-2-[(E)-3-methanesulfonyloxy-1-propenyl]morpholine NMR (CDCl$_3$, δ): 1.47 (9H, m), 2.60–2.72 (1H, m), 2.89–3.02 (1H, m), 3.02 (3H, s), 3.55 (1H, dt, J=2.7, 11.4 Hz), 3.82–4.00 (4H, m), 4.73 (2H, d, J=5.1 Hz), 5.79–6.01 (2H, m)

Preparation 21

To a mixture of 1-amino-1-cyclopropanemethanol hydrochloride (1.1 g), benzaldehyde (945 mg) and triethylamine (1.24 ml) in 1,2-dichloroethane (10 ml), sodium triacetoxyborohydride (5.66 g) was added with ice-cooling over 5 minutes. After being stirred at room temperature for 13 hours, the mixture was poured into aqueous sodium bicarbonate solution and stirred for several hours. The organic layer was separated, dried over magnesium sulfate and evaporated under reduced pressure to give 1-(N-benzylamino)-1-cyclopropanemethanol (641 mg).

IR (Nujol): 3300–2700 cm$^{-1}$ NMR (CDCl$_3$, δ): 0.50–0.77 (4H, m), 3.51 (2H, s), 3.84 (2H, s), 7.19–7.36 (5H, s) MASS: 178 (M+H)$^+$ Preparation 22

The following compound was obtained according to a similar manner to that of Preparation 19.

(2S)-2-(N-Benzylamino)-4-methyl-1-pentanol

NMR (CDCl$_3$, δ): 0.84–0.94 (6H, m), 1.17–1.70 (3H, m), 2.72–2.81 (1H, m), 3.28 (1H, dd, J=6.0, 10.6 Hz), 3.66 (1H, dd, J=3.9, 10.6 Hz), 3.78 (2H, s), 7.20–7.38 (5H, m) MASS: 208 (M+H)$^+$

Preparation 23

Chloroacetyl chloride (421 mg) was added dropwise to a mixture of 1-(N-benzylamino)-1-cyclopropanemethanol (600 mg) and powdered potassium carbonate (702 mg) in dichloromethane (6 ml) with ice-cooling and then the mixture was stirred at room temperature for 2 hours. The resulting mixture was washed with diluted hydrochloric acid and brine successively, and concentrated under reduced pressure. A mixture of the oil obtained by the above procedure and potassium tert-butoxide (380 mg) in tert-butanol (6 ml) was stirred for 2 hours under reflux. After being cooled to room temperature, the mixture was diluted with ethyl acetate (10 ml). The resulting mixture was filtered and the filtrate was concentrated under reduced pressure. The residue was dissolved with ethyl acetate and the ethyl acetate solution was washed with diluted hydrochloric acid and brine successively, dried over magnesium sulfate and concentrated under reduced pressure to give a solid of 4-benzyl-5-oxo-7-oxa-4-azaspiro[2.5]octane (695.3 mg).

IR (KBr): 3100–2800, 1643 cm$^{-1}$ NMR (DMSO-d$_6$, δ): 0.64–1.02 (4H, m), 3.69 (2H, s), 4.43 (2H, s), 4.45 (2H, s), 7.17–7.37 (2H, m) MASS: 218 (M+H)$^+$

Preparation 24

The following compound was obtained according to a similar manner to that of Preparation 21.

(5S)-4-Benzyl-5-(2-methylpropyl)-3-morpholinone

IR (Neat): 1655 cm$^{-1}$ NMR (CDCl$_3$, δ): 0.83 (3H, d, J=6.3 Hz), 0.95 (3H, d, J=6.4 Hz), 1.33–1.60 (2H, m), 1.79–1.92 (1H, m), 3.08–3.17 (1H, m), 3.56–3.79 (1H, m), 3.82 (2H, d, J=15.0 Hz), 4.23 and 4.27 (2H, ABq, J=16.7 Hz), 5.47 (1H, d, J=14.9 Hz), 7.24–7.39 (5H, m) MASS: 248 (M+H)$^+$ Preparation 25

A solution of 4-benzyl-5-oxo-7-oxa-4-azaspiro[2.5]octane (695.3 mg) in tetrahydrofuran (8 ml) was added dropwise to an ice-cooled suspension of lithium aluminum hydride (112 mg) in tetrahydrofuran (5 ml) over 20 minutes and then the mixture was stirred at 50° C. for 2 hours under nitrogen atmosphere. After being cooled to room temperature, sodium fluoride (495 mg) was added to the mixture. The mixture was stirred vigorously and cooled with ice-bath. Water (0.16 ml) was added thereto and the mixture was filtered. The filtrate was concentrated under reduced pressure to give an oil. The oil was purified by column chromatography on silica gel using a mixture of hexane and ethyl acetate as eluent to give 4-benzyl-7-oxa-4-azaspiro[2.5]octane (334.8 mg). 4-Benzyl-7-oxa-4-azaspiro[2.5]octane in ethanol (8 ml) was hydrogenated over palladium hydroxide on carbon for 2 hours at atmospheric pressure. After removal of the catalyst by filtration, the filtrate was treated with 4N hydrogen chloride in ethyl acetate (2 ml) and concentrated under reduced pressure to give 7-oxa-4-azaspiro[2.5]octane hydrochloride (81 mg).

IR (KBr): 3350, 3000–2400 cm$^{-1}$ NMR (CDCl$_3$, δ): 0.84–1.10 (4H, m), 3.75 (2H, s), 3.90–4.10 (4H, m), 10.11 (1H, br s) MASS: 114 (M+H)$^+$ (free)

Preparation 26

The following compound was obtained according to a similar manner to that of Preparation 23.

(3S)-4-Benzyl-3-(2-methylpropyl)morpholine

NMR (CDCl$_3$, δ): 0.89 (3H, d, J=6.2 Hz), 0.93 (3H, d, J=6.3 Hz), 1.20–1.40 (1H, m), 1.46–1.61 (2H, m), 2.17–2.27 (1H, m), 2.40–2.50 (1H, m), 2.59–2.68 (1H, m), 3.16 (1H, d, J=13.3 Hz), 3.40 (1H, dd, J=11.2, 7.8 Hz), 3.59–3.83 (3H, m), 4.04 (1H, d, J=13.3 Hz), 7.21–7.36 (5H, m) MASS: 234 (M+H)$^+$

Preparation 27

The following compound was obtained according to a similar manner to that of Preparation 23.

(3S)-3-(2-Methylpropyl)morpholine hydrochloride

NMR (DMSO-d$_6$, δ): 0.87 (3H, s), 0.90 (3H, s), 1.26–1.52 (2H, m), 1.65–1.78 (1H, m), 3.12–3.48 (4H, m), 3.69 (1H, dt, J=3.4, 12.3 Hz), 3.87–3.95 (2H, m) MASS: 144 (M+H)$^+$ (free)

Preparation 28

A solution of 2-amino-5-bromopyridine (5.0 g) and di-tert-butyl dicarbonate (6.39 g) in tert-butanol (100 ml) was stirred at room temperature for 15 hours. The resulting suspension was concentrated under reduced pressure and the residue was chromatographed on a silica gel using dichloromethane eluent. The fractions containing the objective compound were collected and concentrated under reduced pressure to give 2-(tert-butoxycarbonylamino)-5-bromopyridine (3.25 g)

IR (Nujol): 3210, 1720, 1580, 1525, 1460, 1370 cm$^{-1}$ NMR (CDCl$_3$, δ): 1.56 (9H, s), 7.76 (1H, dd, J=2.5, 8.9 Hz), 7.95 (1H, d, J=8.9 Hz), 8.38 (1H, d, J=2.5 Hz), 8.93 (1H, br s)

Preparation 29

To a solution of (2R)-4-benzyl-1-(3,5-dichlorobenzoyl)-2-(3,4-dimethylbenzyl)piperazine (5.03 g) in dichloromethane (50 ml) was added 1-chloroethyl chloroformate (1.51 ml) slowly at 0° C., and then the mixture was heated at reflux under stirring. After 5.5 hours, the solvent was removed in vacuo and then the resulting residue was dissolved in methanol (20 ml) and refluxed for 0.5 hour. After removal of the solvent, the resulting residue was triturated with isopropyl ether to afford (2R)-1(3,5-dichlorobenzoyl)-2-(3,4-dimethylbenzyl)piperazine hydrochloride (4.84 g).

IR (Nujol): 3350, 1625 cm$^{-1}$ NMR (DMSO-d$_6$, δ): 2.10–4.60 (15H, m), 6.50–9.70 (6H, m) MASS: 377 (M+H)$^+$ (free)

Preparation 30

The following compounds were obtained according to a similar manner to that of Preparation 29.

(1) (2R)-1-(3,5-Dichlorobenzoyl)-2-[(1H-indol-3-yl)methyl]piperazine hydrochloride IR (KBr): 1637 cm$^{-1}$ NMR (DMSO-d$_6$, δ): 2.80–4.80 (9H, m), 6.80–10.20 (8H, m) MASS: 388 (M+H)$^+$ (free)

(2) (2R)-1-(3,5-Dichlorobenzoyl)-2-(2-naphthylmethyl)piperazine hydrochloride

NMR (DMSO-d$_6$, δ): 2.80–4.70 (9H, m), 6.50–8.00 (10H, m) MASS: 399 (M+H)$^+$ (free)

(3) (2R)-1-(3,5-Dichlorobenzoyl)-2-[4-(trifluoromethyl)benzyl]piperazine dihydrochloride IR (KBr): 3430, 2930, 2790, 1648, 1164 cm$^{-1}$ NMR (DMSO-d$_6$, δ): 2.70–5.30 (9H, m), 6.50–7.90 (7H, m), 9.62 (1H, bbr s) MASS: 417 (M+H)$^+$ (free)

(4) (2R)-1-[3,5-Bis(trifluoromethyl)benzoyl]-2-(2-naphthylmethyl)piperazine hydrochloride IR (KBr): 3700–3200, 1639, 1281, 1136 cm$^{-1}$ NMR (DMSO-d$_6$, δ): 2.90–3.80 (7H, m), 4.40–5.30 (2H, m), 6.90–8.30 (10H, m) MASS: 317 (M+H)$^+$ (free)

Preparation 31

(2R)-1-[3,5-Bis(trifluoromethyl)benzoyl]-2-(2-naphthylmethyl)piperazine fumarate (2 g) was treated with 10% aqueous sodium hydroxide solution (14 ml) and dichloromethane (14 ml). The organic layer was separated, washed with brine, dried over magnesium sulfate and evaporated under reduced pressure. A mixture of free piperazine derivative obtained by the above procedure, potassium carbonate (0.76 g) and 1,4-dichloro-2-butyne (0.43 ml) in N,N-dimethylformamide (15 ml) was stirred for 4.5 hours at room temperature. The reaction mixture was poured into water (75 ml) and extracted with ethyl acetate. The extract was washed with brine, dried over magnesium sulfate and evaporated under reduced pressure. The residue was purified by column chromatography on silica gel using a mixed-solvent of toluene and ethyl acetate (10:1) as eluent to give (2R)-1-[3,5-bis(trifluoromethyl)benzoyl]-4-(4-chloro-2-butynyl)-2-(2-naphthylmethyl)piperazine (1.18 g).

IR (Neat): 3600–3100, 1638, 1275, 1127, 900 cm$^{-1}$ NMR (CDCl$_3$, δ): 2.31–5.30 (13H, m), 6.90–7.95 (10H, m) MASS: 553 (M+H)$^+$

EXAMPLE 1

(1) A mixture of (2R)-1-[3,5-bis(trifluoromethyl)benzoyl]-2-[(1H-indol-3-yl)methyl]piperazine (0.67 g), 1-chloro-3-(3-pyridyl)-2-propyne hydrochloride (0.3 g) and potassium carbonate (0.52 g) in N,N-dimethylformamide (5 ml) was stirred for 5 hours at 50° C. The mixture was poured into water and extracted with ethyl acetate. The extract was washed with brine, dried over magnesium sulfate and evaporated under reduced pressure. The residue was purified by column chromatography on silica gel using ethyl acetate as eluent to give (2R)-1-[3,5-bis(trifluoromethyl)benzoyl]-2-[(1H-indol-3-yl)methyl]-4-[3-(3-pyridyl)-2-propynyl]piperazine (0.25 g) as a syrup.

(2) The following compound was prepared by treatment of (2R)-1-[3,5-bis(trifluoromethyl)benzoyl]-2-[(1H-indol-3-yl)methyl]-4-[3-(3-pyridyl)-2-propynyl]piperazine with 4N hydrochloric acid in ethyl acetate.

(2R)-1-[3,5-Bis(trifluoromethyl)benzoyl]-2-[(1H-indol-3-yl)methyl]-4-[3-(3-pyridyl)-2-propynyl]piperazine dihydrochloride mp: 180–190° C. [α]$_D^{24.6}$: −10.50° (C=0.1, MeOH) IR (Nujol): 3600–3200, 2700–2500, 1643, 1530, 1428, 1361, 1280 cm$^{-1}$ NMR (DMSO-d$_6$, δ): 3.20–5.20 (11H, m), 6.40–8.30 (10H, m), 8.74–8.80 (1H, m), 8.85–8.90 (2H, m), 10.90–11.10 (1H, m) MASS: 571 (M+H)$^+$ (free) Elemental Analysis Calcd. for C$_{30}$H$_{24}$F$_6$N$_4$O.2HCl.1.8H$_2$O: C, 53.31; H, 4.41; N, 8.29. Found: C, 53.28; H, 4.53; N, 7.87.

EXAMPLE 2

The following compounds were obtained according to a similar manner to that of Example 1.

(1) (2R)-1-[3,5-Bis(trifluoromethyl)benzoyl]-2-(3,4-dimethylbenzyl)-4-[3-(6-methoxypyridin-3-yl)-2-propynyl]piperazine dihydrochloride mp: 160–170° C. [α]$_D^{24.2}$: −14.72° (C=0.55, MeOH) IR (KBr): 3600–3300, 2700–2500, 1648, 1617, 1494, 1430, 1280 cm$^{-1}$ NMR (DMSO-d$_6$, δ): 2.05–2.20 (6H, m), 2.80–5.20 (11H, m), 3.90 (3H, s), 6.50–8.40 (9H, m) MASS: 590 (M+H)$^+$ (free) Elemental Analysis Calcd. for C$_{31}$H$_{29}$F$_6$N$_3$O$_2$.2HCl.0.5H$_2$O: C, 55.45; H, 4.80; N, 6.26. Found: C 55.28, H, 4.86; N, 6.12.

(2) (2R)-1-[3,5-Bis(trifluoromethyl)benzoyl]-2-[(1H-indol-3-yl)methyl]-4-[3-(6-methoxypyridin-3-yl)-2-propynyl]piperazine dihydrochloride mp: 183–189° C. [α]$_D^{23.9}$:

−21.0° (C=0.55, MeOH) IR (KBr): 3600–3300, 2700–2500, 1644, 1602, 1494, 1428, 1280 cm$^{-1}$ NMR (DMSO-d$_6$, δ): 3.20–5.20 (11H, m), 3.90 (3H, s), 6.60–8.40 (11H, m), 10.95 (1H, br s), 12.00–12.40 (2H, m) MASS: 600 (M+H)$^+$ (free) Elemental Analysis Calcd. for C$_{31}$H$_{26}$F$_6$N$_4$O$_2$.2HCl.H$_2$O: C, 53.85; H, 4.37; N, 8.10. Found: C, 53.90; H, 4.36; N, 8.02.

(3) (2R)-1-[3,5-Bis(trifluoromethyl)benzoyl]-2-[(1H-indol-3-yl)methyl]-4-[3-(2-pyridyl)-2-propynyl]piperazine

EXAMPLE 3

(2R)-1-[3,5-Bis(trifluoromethyl)benzoyl]-2-(3,4-dimethylbenzyl)-4-[3-(2-pyridyl)-2-propynyl]piperazine dihydrochloride (0.2 g) was made free with saturated aqueous sodium bicarbonate solution and extracted with ethyl acetate. The extract was dried over magnesium sulfate and evaporated under reduced pressure. The resulting residue dissolved in methanol (10 ml) and the solution was hydrogenated over 10% palladium on activated carbon (50 mg) at room temperature under 2–3 atoms. After removal of catalyst by filtration, the filtrate was concentrated under reduced pressure. The residue was treated with 4N hydrogen chloride in ethyl acetate solution to give (2R)-1-[3,5-bis(trifluoromethyl)benzoyl]-2-(3,4-dimethylbenzyl)-4-[3-(2-pyridyl)propyl]piperazine dihydrochloride.

mp: 120–130° C. [α]$_D^{24.5}$: −12.81° (C=0.32, MeOH) IR (Nujol): 3600–3300, 2700–2500, 1635, 1450, 1380, 1280 cm$^{-1}$ NMR (DMSO-d$_6$, δ): 2.00–5.20 (21H, m), 6.60–7.80 (5H, m), 7.80 (1H, d, J=8.0 Hz), 7.88 (1H, t, J=7.0 Hz), 8.18 (1H, s), 8.49 (1H, t, J=7.1 Hz), 8.81 (1H, d, J=5.2 Hz), 11.20–12.20 (2H, m) MASS: 564 (M+H)$^+$ (free)

Elemental Analysis Calcd. for C$_{30}$H$_{31}$F$_6$N$_3$O.2HCl.2.7H$_2$O: C, 52.59; H, 5.65; N, 6.13. Found: C, 52.66; H, 5.78; N 5.77.

EXAMPLE 4

(1) (2R)-1-[3,5-Bis(trifluoromethyl)benzoyl]-2-[(1H-indol-3-yl)methyl]-4-[3-(3-pyridyl)propyl]piperazine dihydrochloride mp: 150–160° C. [α]$_D^{22.9}$: −2.86° (C=0.42, MeOH) IR (KBr): 3600–3000, 2700–2010, 1641, 1554, 1461, 1428, 1280 cm$^{-1}$ NMR (DMSO-d$_6$, δ): 2.10–5.20 (15H, m), 6.60–8.30 (9H, m), 8.45–8.55 (1H, m), 8.80–9.00 (2H, m), 10.95–11.05 (1H, m), 11.90–12.00 (2H, br s) MASS: 575 (M+H)$^+$ (free) Elemental Analysis Calcd. for C$_{30}$H$_{28}$F$_6$N$_4$O.2HCl.1.2H$_2$O: C, 50.71; H, 5.25; N, 7.89. Found: C, 50.65; H, 5.35; N 7.20.

(2) (2R)-1-[3,5-Bis(trifluoromethyl)benzoyl]-2-[(1H-indol-3-yl)methyl]-4-[3-(2-pyridyl)propyl]piperazine dihydrochloride mp: 80–100° C. [α]$_D^{23.1}$: −5.29° (C=0.86, MeOH) IR (KBr): 3600–3300, 2700–2500, 1637, 1617, 1460, 1282 cm$^{-1}$ NMR (DMSO-d$_6$, δ): 2.20–2.40 (2H, m), 3.10–5.20 (13H, m), 6.60–8.30 (10H, m), 8.49 (1H, d, J=7.8 Hz), 8.80 (1H, d, J=5.0 Hz), 10.90–11.05 (1H, br s) MASS: 575 (M+H)$^+$ (free) Elemental Analysis Calcd. for C$_{30}$H$_{28}$F$_6$N$_4$O.2HCl.1.2H$_2$O: C, 53.85; H, 4.88; N, 8.37. Found: C, 53.92; H, 5.30; N 7.66.

(3) (2R)-1-[3,5-Bis(trifluoromethyl)benzoyl]-2-[(1H-indol-3-yl)methyl]-4-[4-(3-pyridyl)butyl]piperazine dihydrochloride mp: 140–145° C. [α]$_D^{22.3}$: −8.33° (C=0.30, MeOH) IR (Nujol): 3600–3000, 2700–2300, 1641, 1465, 1430, 1280 cm$^{-1}$ NMR (DMSO-d$_6$, δ): 1.60–5.20 (17H, m), 6.60–9.00 (12H, m), 11.00 (1H, br s), 11.59 (1H, br s) MASS: 589 (M+H)$^+$ (free) Elemental Analysis Calcd. for C$_{31}$H$_{30}$F$_6$N$_4$O.2HCl.2H$_2$O: C, 53.38; H, 5.20; N, 8.03. Found: C, 53.47; H, 5.28; N, 7.51.

EXAMPLE 5

(1) Methanesulfonyl chloride (0.094 ml) was added to a mixture of (Z)-3-(3-pyridyl)-2-propen-1-ol (0.15 g) and triethylamine (0.2 ml) in dichloromethane (2 ml) under −10° C. After being stirred at the same temperature for 0.5 hour, the reaction mixture was washed with saturated sodium bicarbonate, dried over magnesium sulfate and evaporated under reduced pressure. The obtained mesylate was added to a mixture of (2R)-1-[3,5-bis(trifluoromethyl)benzoyl]-2-[(1H-indol-3-yl)methyl]piperazine (0.5 g), powdered potassium carbonate (0.61 g) and catalytic amount of potassium iodide in a mixed solvent of acetonitrile (10 ml) and N,N-dimethylformamide (2 ml). The resulting mixture was stirred at 50° C. for 1.5 hours and then filtered. The filtrate was evaporated under reduced pressure and the resulting residue was purified by column chromatography on silica gel using a mixed solvent of dichloromethane and methanol as eluent. The fractions containing the objective compound were collected and evaporated under reduced pressure to give (2R)-1-[3,5-bis(trifluoromethyl)benzoyl]-2-[(1H-indol-3-yl)methyl]-4-[(Z)-3-(3-pyridyl)-2-propenyl]piperazine (0.49 g) as a syrup.

NMR (CDCl$_3$, δ): 1.80–5.20 (11H, m), 5.97 (1H, dt, J=6.6, 11.7 Hz, cis), 6.60 (1H, d, J=11.7 Hz, cis), 6.80–8.00 (10H, m), 8.23 (1H, s), 8.45–8.60 (2H, m) MASS: 562 (M+H)$^+$ (2) The following compound was prepared by treatment of (2R)-1-[3,5-bis(trifluoromethyl)benzoyl]-2-[(1H-indol-3-yl)methyl]-4-[(Z)-3-(3-pyridyl)-3-propenyl]piperazine with 4N hydrogen chloride in ethyl acetate.

(2R)-1-[3,5-Bis(trifluoromethyl)benzoyl]-2-[(1H-indol-3-yl)methyl]-4-[(Z)-3-(3-pyridyl)-2-propenyl]piperazine dihydrochloride mp: 165–177° C. [α]$_D^{22.9}$: +14.9° (C=0.50, MeOH) IR (KBr): 3600–3300, 2700–2500, 1641, 1457, 1427, 1359, 1280, 1184 cm$^{-1}$ NMR (DMSO-d$_6$, δ): 3.00–5.20 (11H, m), 6.40–8.40 (12H, m), 8.70–8.85 (2H, m), 11.05 (1H, br s), 12.00 (2H, m) MASS: 573 (M+H)$^+$ (free)

Elemental Analysis Calcd. for C$_{30}$H$_{26}$F$_6$N$_4$O.2HCl.2.5H$_2$O: C, 52.18; H, 4.82; N, 8.11. Found: C, 52.34; H, 4.73; N, 8.01.

EXAMPLE 6

The following compounds were obtained according to a similar manner to that of Example 5.

(1) (2R)-1-[3,5-Bis(trifluoromethyl)benzoyl]-2-(3,4-dimethylbenzyl)-4-[(E)-3-(3-pyridyl)-2-propenyl]piperazine dihydrochloride mp: 170–174° C. [α]$_D^{24.1}$: −8.50° (C=0.20, MeOH) IR (KBr): 3600–3300, 2700–2500, 1643, 1554, 1432, 1367, 1280 cm$^{-1}$ NMR (DMSO-d$_6$, δ): 2.00–2.30 (6H, m), 2.80–5.20 (6H, m), 6.60–9.05 (12H, m) MASS: 562 (M+H)$^+$ (free) Elemental Analysis Calcd. for C$_{30}$H$_{29}$F$_6$N$_3$O.2HCl.2.0H$_2$O: C, 53.74; H, 5.26; N, 6.27. Found: C, 53.71; H, 5.33; N, 5.83.

(2) (2R)-1-[3,5-Bis(trifluoromethyl)benzoyl]-2-[(1H-indol-3-yl)methyl]-4-[4-(3-pyridyl)-3-butynyl]piperazine NMR (CDCl$_3$, δ): 2.20–5.20 (13H, m), 6.80–8.00 (10H, m), 8.15 (1H, s), 8.49 (1H, d, J=3.8 Hz), 8.64 (1H, br s) MASS: 585 (M+H)$^+$ (3) (2R)-1-[3,5-Bis(trifluoromethyl)benzoyl]-2-(3,4-dimethylbenzyl)-4-[3-(1H-pyrazol-1-yl)propyl]piperazine hydrochloride mp: 73–75° C. [α]$_D^{24.7}$: −17.30° (C=0.50, MeOH) IR (KBr): 1640 cm$^{-1}$ NMR (DMSO-d$_6$, δ): 1.85–5.20 (21H, m), 6.20–8.30 (9H, m) MASS: 553 (M+H)$^+$ (free) Elemental Analysis Calcd. for $C_{28}H_{31}ClF_6N_4O.2H_2O$: C, 53.80; H, 5.64; N, 8.96. Found: C, 53.67; H, 5.56; N, 7.83.

EXAMPLE 7

The following compounds were obtained according to a similar manner to that of Example 5-(2).

(1) (2R)-1-[3,5-Bis(trifluoromethyl)benzoyl]-2-[(1H-indol-3-yl)methyl]-4-[3-(2-pyridyl)-2-propynyl]piperazine dihydrochloride mp: 160–166° C. $[\alpha]_D^{24.7}$: −16.80° (C=0.50, MeOH) IR (KBr): 3600–3200, 2700–2500, 1643, 1540, 1380, 1280 cm$^{-1}$ NMR (DMSO-d$_6$, δ): 3.20–5.20 (11H, m), 6.60–8.30 (11H, m), 8.65 (1H, d, J=2.7 Hz), 10.90–11.05 (1H, m) MASS: 571 (M+H)$^+$ (free), 607 Elemental Analysis Calcd. for $C_{30}H_{24}F_6N_4O.2HCl.1.5H_2O$: C, 53.74; H, 4.36; N, 8.36. Found: C, 53.73; H, 4.66; N, 7.71.

(2) (2R)-1-[3,5-Bis(trifluoromethyl)benzoyl]-2-[(1H-indol-3-yl)methyl]-4-[4-(3-pyridyl)-3-butynyl]piperazine dihydrochloride mp: 175–185° C. $[\alpha]_D^{21.7}$: −10.30° (C=0.50, MeOH) IR (KBr): 3600–3300, 2700–2500, 1641, 1459, 1428, 1368, 1282 cm$^{-1}$ NMR (DMSO-d$_6$, δ): 3.20–5.20 (13H, m), 6.60–8.30 (9H, m), 8.65–8.85 (2H, m), 10.99 (1H, s), 11.90–12.10 (2H, m) MASS: 585 (M+H)$^+$ (free) Elemental Analysis Calcd. for $C_{31}H_{26}F_6N_4O.2HCl.1.2H_2O$: C, 54.83; H, 4.51; N, 8.25. Found: C, 54.79; H, 4.87; N, 7.67.

EXAMPLE 8

A mixture of (2R)-1-[3,5-bis(trifluoromethyl)benzoyl]-2-[(1H-indol-3-yl)methyl]-4-(4-chloro-2-butynyl)piperazine (0.25 g), (R)-2-(methoxymethyl)pyrrolidine (0.10 g), potassium carbonate (0.25 g) and potassium iodide (10 mg) in dry N,N-dimethylformamide (5 ml) was stirred for 5 hours at room temperature. The mixture was poured into water and extracted with ethyl acetate. The extract was washed with brine, dried over magnesium sulfate and evaporated under reduced pressure. The residue was purified by column chromatography on silica gel using ethyl acetate as eluent and treated with 4N hydrogen chloride in ethyl acetate solution to give (2R)-1-[3,5-bis(trifluoromethyl)benzoyl]-2-[(1H-indol-3-yl)methyl]-4-[4-[(2R)-2-(methoxymethyl)pyrrolidino]-2-butynyl]piperazine dihydrochloride (0.19 g).

mp: 190–195° C. $[\alpha]_D^{24.8}$: +9.3° (C=0.50, MeOH) IR (Nujol): 3600–3200, 2700–2500, 1641, 1552, 1428, 1280 cm$^{-1}$ NMR (DMSO-d$_6$, δ): 1.6–2.40 (4H, m), 3.10–5.20 (18H, m), 6.60–8.30 (8H, m), 11.50–11.70 (3H, m) MASS: 621 (M+H)$^+$ (free) Elemental Analysis Calcd. for $C_{32}H_{34}F_6N_4O_2.2HCl.1.5H_2O$: C, 53.34; H, 5.46; N, 7.78. Found: C, 53.35; H, 5.54; N, 7.60.

EXAMPLE 9

To a mixture of 3,5-dichlorobenzoic acid (2.6 g), (3R)-1-benzyl-3-(3,4-dimethylbenzyl)piperazine dihydrochloride (5.0 g) and triethylamine (8.54 ml) in dichloromethane (80 ml) was added 2-chloro-1-methylpyridinium iodide (3.83 g) under ice-cooling, and then the mixture was stirred at room temperature for 1 hour. The mixture was evaporated under reduced pressure, and the resulting residue was dissolved into ethyl acetate. The ethyl acetate solution was filtrated and evaporated under reduced pressure. The resulting residue was purified by column chromatography on silica gel using hexane-ethyl acetate (10:1) as eluent to give (2R)-4-benzyl-1-(3,5-dichlorobenzoyl)-2-(3,4-dimethylbenzyl)piperazine (5.58 g).

IR (Nujol): 2500, 1635 cm$^{-1}$ NMR (DMSO-d$_6$, δ): 1.90–2.30 (8H, m), 2.55–4.80 (9H, m), 6.50–7.15 (5H, m), 7.20–7.40 (5H, m), 7.59 (1H, br) MASS: 467 (M+H)$^+$

EXAMPLE 10

The following compound was obtained according to a similar manner to that of Example 9.

(2R)-4-Benzyl-1-(3,5-dichlorobenzoyl)-2-[4-(trifluoromethyl)benzyl]piperazine

IR (Neat): 2942, 2809, 1641, 1070 cm$^{-1}$ NMR (DMSO-d$_6$, δ): 2.00–4.90 (11H, m), 6.59 (1H, s), 7.10–7.70 (11H, m) MASS: 507 (M+H)$^+$

EXAMPLE 11

To a solution of (3R)-1-benzyl-3-(2-naphthylmethyl)piperazine (3.23 g) and triethylamine (4.3 ml) in dichloromethane (60 ml) was added a solution of 3,5-dichlorobenzoyl chloride (6.0 g) in dichloromethane (10 ml) at 0° C. After stirring at room temperature for 3 hours, the mixture was quenched with water and extracted three times with ethyl acetate. The combined extracts were dried over magnesium sulfate, and evaporated under reduced pressure. The obtained residue was triturated with a mixture of dichloromethane and hexane to give (2R)-4-benzyl-1-(3,5-dichlorobenzoyl)-2-(2-naphthylmethyl)piperazine.

NMR (DMSO-d$_6$, δ): 3.00–4.70 (9H, m), 6.66–7.86 (17H, m) MASS: 689 (M+H)$^+$ (free)

EXAMPLE 12

The following compound was obtained according to a similar manner to that of Example 11.

(2R)-4-Benzyl-1-(3,5-dichlorobenzoyl)-2-[(1H-indol-3-yl)methyl]piperazine

NMR (DMSO-d$_6$, δ): 2.10–4.60 (9H, m), 5.76 (2H, s), 6.70–7.68 (13H, m) MASS: 388 (M+H)$^+$ (free)

EXAMPLE 13

The following compound was obtained according to a similar manner to that of Example 1-(1).

(2R)-1-[3,5-Bis(trifluoromethyl)benzoyl]-2-(2-naphthylmethyl)-4-[3-(3-pyridyl)-2-propynyl]piperazine dihydrochloride mp: 140–150° C. $[\alpha]_D^{25.9}$: −9.2°(C=0.50, MeOH)

IR (KBr): 3700–3200, 3000–2300, 1644, 1550, 1428, 1367, 1280 cm$^{-1}$ NMR (DMSO-d$_6$, δ): 2.20–5.20 (11H, m), 7.00–8.65 (14H, m) MASS: 582 (M+H)$^+$ (free) Elemental Analysis Calcd. for $C_{31}H_{25}F_6N_4O.2HCl.2.57H_2O$: C, 54.85; H, 4.62; N, 6.00. Found: C, 54.85; H, 4.56; N, 5.86.

EXAMPLE 14

(1) Lindlar catalyst (Pd—CaCO$_3$—PbO) (86 mg) was added to a solution of (2R)-1-[3,5-bis(trifluoromethyl)benzoyl]-2-(2-naphthylmethyl)-4-[3-(3-pyridyl)-2-propynyl]piperazine in methanol (20 ml). The mixture was stirred for 2 hours under hydrogen at 25° C. and filtered. The filtrate was concentrated under reduced pressure and the resulting residue was chromatographed on silica gel using a mixed eluent of hexane and ethyl acetate. The faster eluting fractions were collected, concentrated under reduced pressure and treated with 4N hydrogen chloride in ethyl acetate to give (2R)-1-[3,5-bis(trifluoromethyl)benzoyl]-2-(2-naphthylmethyl)-4-[(2Z)-3-(3-pyridyl)-2-propenyl]piperazine dihydrochloride.

mp: 130–150° C. $[\alpha]_D^{27.5}$: −25.20° (C=0.25, MeOH) IR (KBr): 3700–2200, 1646, 1280 cm$^{-1}$ NMR (DMSO-d$_6$, δ): 2.00–5.20 (11H, m), 6.30–8.90 (16H, m) MASS: 584 (M+H)$^+$ (free) Elemental Analysis Calcd. for $C_{32}H_{27}F_6N_3O\cdot 2HCl\cdot 3.7H_2O$: C, 53.19; H, 5.07; N, 5.82. Found: C, 53.19; H, 5.21; N, 5.61.

(2) The slower eluting fractions were collected, concentrated under reduced pressure and treated with 4N hydrogen chloride in ethyl acetate to give (2R)-1-[3,5-bis(trifluoromethyl)benzoyl]-2-(2-naphthylmethyl)-4-[3-(3-pyridyl)propyl]piperazine dihydrochloride.

mp: 138–148° C. $[\alpha]_D^{26.4}$: −28.60° (C=0.25, MeOH) IR (KBr): 3700–2200, 1646, 1280, 1135 cm$^{-1}$ NMR (DMSO-d$_6$, δ): 2.00–5.20 (15H, m), 6.30–8.90 (14H, m) MASS: 586 (M+H)$^+$ (free) Elemental Analysis Calcd. for $C_{32}H_{29}F_6N_3O\cdot 2HCl\cdot 2.9H_2O$: C, 54.10; H, 5.22; N, 5.92. Found: C, 54.11; H, 5.37; N, 5.70.

EXAMPLE 15

A mixture of (2R)-1-(3,5-dichlorobenzoyl)-2-(3,4-dimethylbenzyl)piperazine hydrochloride (400 mg) and 4-(4-chloro-2-butynyl)morpholine hydrochloride (223 mg) in dried acetonitrile (4.0 ml) was stirred at 50° C. in the presence of is powdered potassium carbonate (534 mg) and potassium iodide (32 mg). After 3 hours, the reaction mixture was filtered and the insoluble material on the filter was washed with acetonitrile. The filtrate and the washing were combined and then concentrated in vacuo. The resulting residue was purified by column chromatography on silica gel using a mixture of ethyl acetate and methanol (1.0:1) as eluent. The product obtained was dissolved in ethyl acetate and treated with 4N hydrogen chloride in ethyl acetate to give (2R)-1-(3,5-dichlorobenzoyl)-2-(3,4-dimethylbenzyl)-4-(4-morpholino-2-butynyl)piperazine dihydrochloride (221 mg).

mp: 175° C. (dec.) $[\alpha]_D^{27.9}$: +6.80° (C=0.50, MeOH) IR (Nujol): 2400, 1640, 1120 cm$^{-1}$ NMR (DMSO-d$_6$, δ): 2.10–4.40 (21H, m), 6.69 (3H, br), 7.06 (2H, br), 7.61 (1H, br) MASS: 514 (M+H)$^+$ (free) Elemental Analysis Calcd. for $C_{28}H_{33}Cl_2N_3O_2\cdot 2HCl\cdot 2H_2O$: C, 53.94; H, 6.30; N, 6.74. Found: C, 53.86; H, 6.15; N, 6.41.

EXAMPLE 16

The following compounds were obtained according to a similar manner to that of Example 15.

(1) (2R)-1-(3,5-Dichlorobenzoyl)-2-(3,4-dimethylbenzyl)-4-(4-thiomorpholino-2-butynyl)piperazine dihydrochloride mp: 128° C. (dec.) $[\alpha]_D^{28.0}$: +6.40° (C=0.50, MeOH) IR (Nujol): 2400, 1635 cm$^{-1}$ NMR (DMSO-d$_6$, δ): 2.05–4.70 (21H, m), 6.71 (3H, br), 7.04 (2H, br), 7.61 (1H, br) MASS: 530 (M+H)$^+$ (free) Elemental Analysis Calcd. for $C_{28}H_{33}Cl_2N_3OS\cdot 2HCl\cdot 2H_2O$: C, 52.59; H, 6.15; N, 6.57. Found: C, 52.72; H, 6.19; N, 6.35.

(2) (2R)-1-(3,5-Dichlorobenzoyl)-2-(3,4-dimethylbenzyl)-4-[(E)-4-morpholino-2-butenyl]piperazine dihydrochloride mp: >230° C. $[\alpha]_D^{25.3}$: +5.80° (C=0.50, MeOH) IR (KBr): 3426, 2927, 1120, 970 cm$^{-1}$ NMR (DMSO-d$_6$, δ): 2.10–4.70 (23H, m), 6.17 (2H, br), 6.69 (3H, br), 7.07 (2H, br), 7.63 (1H, br) MASS: 516 (M+H)$^+$ (free) Elemental Analysis Calcd. for $C_{28}H_{37}Cl_4N_3O_2\cdot 0.5H_2O$: C, 56.20; H, 6.40; N, 7.02. Found: C, 56.20; H, 6.29; N, 6.89.

(3) (2R)-1-(3,5-Dichlorobenzoyl)-2-[(1H-indol-3-yl)methyl]-4-(4-thiomorpholino-2-butynyl)piperazine dihydrochloride mp: 175° C. (dec.) $[\alpha]_D^{26.0}$: +26.0° (C=0.50, MeOH) IR (KBr): 3407, 2543, 1639 cm$^{-1}$ NMR (DMSO-d$_6$, δ): 2.60–5.10 (21H, m), 6.70–7.80 (8H, m), 11.02 (1H, br s) MASS: 541 (M+H)$^+$ (free) Elemental Analysis Calcd. for $C_{28}H_{32}Cl_4N_4OS\cdot 1.5H_2O$: C, 52.43; H, 5.50; N, 8.73. Found: C, 52.34; H, 5.60; N, 8.42.

(4) (2R)-1-(3,5-Dichlorobenzoyl)-2-[(1H-indol-3-yl)methyl]-4-(4-morpholino-2-butynyl)piperazine dihydrochloride mp: 165° C. (dec.) $[\alpha]_D^{26.0}$: +27.50° (C=0.50, MeOH) IR (KBr): 3407, 1639, 1126 cm$^{-1}$ NMR (DMSO-d$_6$, δ): 2.80–5.20 (21H, m), 6.70–7.85 (8H, m), 11.00 (1H, br s) MASS: 525 (M+H)$^+$ (free) Elemental Analysis Calcd. for $C_{28}H_{32}Cl_4N_4O_2\cdot 3H_2O$: C, 51.55; H, 5.87; N, 8.59 Found: C, 51.59; H, 5.52; N, 8.33.

(5) (2R)-1-(3,5-Dichlorobenzoyl)-2-(2-naphthylmethyl)-4-(4-thiomorpholino-2-butynyl)piperazine dihydrochloride mp: 154° C. (dec.) $[\alpha]_D^{23.8}$: −14.10° (C=0.50, MeOH) IR (KBr): 3417, 2933, 2537, 1641 cm$^{-1}$ NMR (DMSO-d$_6$, δ): 2.70–5.20 (21H, m), 6.56 (1H, br), 7.08 (1H, br), 7.53 (4H, br), 7.89 (4H, br) MASS: 552 (M+H)$^+$ (free) Elemental Analysis Calcd. for $C_{30}H_{33}Cl_4N_3OS\cdot 1.5H_2O$: C, 55.22; H, 5.56; N, 6.44. Found: C, 55.09; H, 5.64; N, 6.31.

(6) (2R)-1-(3,5-Dichlorobenzoyl)-2-(2-naphthylmethyl)-4-(4-morpholino-2-butynyl)piperazine dihydrochloride mp: 171° C. (dec.) $[\alpha]_D^{23.3}$: −15.10° (C=0.50, MeOH) IR (KBr): 3407, 2931, 2561, 1641, 971 cm$^{-1}$ NMR (DMSO-d$_6$, δ): 3.00–5.20 (21H, m), 6.56 (1H, br), 7.08 (1H, br), 7.53 (4H, br), 7.89 (4H, br) MASS: 536 (M+H)$^+$ (free) Elemental Analysis Calcd. for $C_{30}H_{33}Cl_4N_3O_2\cdot H_2O$: C, 57.43; H, 5.62; N, 6.70. Found: C, 57.67; H, 5.68; N, 6.31.

(7) (2R)-1-(3,5-Dichlorobenzoyl)-2-[4-(trifluoromethyl)benzyl]-4-(4-thiomorpholino-2-butynyl)piperazine dihydrochloride mp: 172° C. (dec.) $[\alpha]_D^{25.4}$: +15.80° (C=0.50, MeOH) IR (KBr): 3430, 2917, 2524, 1641, 1068 cm$^{-1}$ NMR (DMSO-d$_6$, δ): 2.70–5.20 (21H, m), 6.69 (1H, s), 7.10–7.30 (2H, m), 7.63 (4H, br) MASS: 570 (M+H)$^+$ (free) Elemental Analysis Calcd. for $C_{27}H_{30}Cl_4F_3N_3OS\cdot 0.5H_2O$: C, 49.71; H, 4.79; N, 6.44. Found: C, 49.37; H, 5.09; N, 6.30.

(8) (2R)-1-(3,5-Dichlorobenzoyl)-2-[4-(trifluoromethyl)benzyl]-4-(4-morpholino-2-butynyl)piperazine dihydrochloride mp: 186° C. (dec.) $[\alpha]_D^{25.4}$: +17.50° (C=0.50, MeOH) IR (KBr): 3421, 2935, 2553, 1644, 1068 cm$^{-1}$ NMR (DMSO-d$_6$, δ): 2.80–5.20 (21H, m), 6.72 (1H, s), 7.10–7.40 (2H, m), 7.64 (4H, br) MASS: 554 (M+H)$^+$ (free) Elemental Analysis Calcd. for $C_{27}H_{30}Cl_4F_3N_3O_2\cdot 0.5H_2O$: C, 50.96; H, 4.91; N, 6.60. Found: C, 50.57; H, 5.05; N, 6.52.

EXAMPLE 17

A mixture of (2R)-1-(3,5-dichlorobenzoyl)-2-(3,4-dimethylbenzyl)piperazine hydrochloride (300 mg), 3-bromo-1-propanol (121 mg), potassium carbonate (251 mg) and potassium iodide (24 mg) in dried acetonitrile (3 ml) was stirred at 50° C. for 10 hours. After being cooled to room temperature, the reaction mixture was filtered and the filtrate was concentrated under reduced pressure. The residue was purified by column chromatography on silica gel using ethyl acetate as eluent to give (2R)-1-(3,5-dichlorobenzoyl)-2-(3,4-dimethylbenzyl)-4-(3-hydroxypropyl)piperazine as a syrup. Methanesulfonyl chloride (58 mg) was added to an ice-cooled solution of the alcohol obtained at above procedure (210 mg) and triethylamine (97.6 mg) in dichloromethane (4 ml) over 1.5 hours. After being stirred for 1 hour, the reaction mixture was washed with saturated sodium bicarbonate solution, dried over magnesium sulfate and evaporated under reduced pressure to give the corresponding mesylate. A mixture of the mesylate obtained by the above procedure, 4-aminomorpholine (59.1 mg) and triethylamine (73.2 mg) in methanol (4 ml) was stirred under reflux for 4 hours. The reaction mixture was concentrated under reduced pressure and the residue was purified by column chromatography on silica gel using ethyl acetate as eluent and treated with 4N hydrogen chloride in ethyl acetate solution to give (2R)-1-(3,5-dichlorobenzoyl)-2-(3,4-dimethylbenzyl)-4-(N-morpholino-3-aminopropyl)piperazine dihydrochloride.

mp: 71° C. (dec.) $[\alpha]_D^{22.5}$: +1.00° (C=0.50, MeOH) IR (Nujol): 3400; 2950, 1640, 1100 cm$^{-1}$ NMR (DMSO-d$_6$, δ): 2.10–4.70 (23H, m), 6.68 (3H, br), 7.06 (2H, br), 7.63 (1H, br) MASS: 519 (M+H)$^+$ (free) Elemental Analysis Calcd. for C$_{27}$H$_{38}$Cl$_4$N$_4$O$_2$.2.5H$_2$O: C, 50.87; H, 6.80; N, 8.79. Found: C, 51.03; H, 7.15; N, 8.84.

EXAMPLE 18

Under nitrogen atmosphere, to a mixture of (2R)-1-[3,5-bis(trifluoromethyl)benzoyl]-2-(3,4-dimethylbenzyl) piperazine (315 mg) and 3-(1-methyl-1H-imidazol-4-yl) propanal (98 mg) in dichloromethane (6 ml) was added sodium triacetoxyborohydride (225 mg) and'stirred at room temperature. After 4 hours, aqueous sodium bicarbonate solution was added to the mixture and the mixture was stirred for several minutes. The organic layer was separated, dried over sodium sulfate and evaporated under reduced pressure. The resulting residue was purified by column chromatography on silica gel using dichloromethanemethanol (10:1) as eluent and treated with 4N hydrogen chloride in ethyl acetate solution to give (2R)-1-[3,5-bis (trifluoromethyl)benzoyl]-2-(3,4-dimethylbenzyl)-4-[3-(1-methyl-1H-imidazol-4-yl)propyl]piperazine dihydrochloride (187.1 mg).

mp: 91° C. (dec.) $[\alpha]_D^{24.2}$: −11.20° (C=0.50, MeQH) IR (Nujol): 1640 cm$^{-1}$ NMR (DMSO-d$_6$, δ): 2.00–5.20 (21H, m), 6.67 (1H, br s), 6.90–7.20 (2H, m), 7.44 (1H, br s), 7.56 (1H, br s), 7.67 (1H, br s), 8.18 (1H, br s), 9.03 (1H, br s) MASS: 567 (M+H)$^+$ (free) Elemental Analysis Calcd. for C$_{29}$H$_{34}$Cl$_2$F$_6$N$_4$O.3.5H$_2$O: C, 49.58; H, 5.88; N, 7.97. Found: C, 49.71; H, 5.90; N, 7.79.

EXAMPLE 19

A mixture of (2R)-1-[3,5-bis(trifluoromethyl)benzoyl]-2-(3,4-dimethylbenzyl)piperazine (500 mg), 2-(2-chloroethoxy)ethanol (168 mg), potassium carbonate (233 mg) and potassium iodide (56 mg) in N,N-dimethylformamide (2 ml) was heated with stirring at 50° C. for 17 hours, 60° C. for 13 hours and 70° C. for 1 hour. The reaction mixture was partitioned between ethyl acetate and water. The organic layer was washed with brine and dried over magnesium sulfate. After evaporation of the solvent, the resulting residue was purified by column chromatography on silica gel using dichloromethane-methanol (10:1) as eluent to give (2R)-1-[3,5-bis(trifluoromethyl)benzoyl]-2-(3,4-dimethylbenzyl)-4-[2-(2-hydroxyethoxy)ethyl] piperazine (359 mg).

IR (Neat): 3450, 1640, 1440, 1280, 1.130 cm$^{-1}$ NMR (DMSO-d$_6$, δ): 2.03–4.93 (23H, m), 6.60–8.20 (6H, m) MASS: 533 (M+H)$^+$

EXAMPLE 20

To a stirred solution of oxalyl chloride (151 mg) in dichloromethane (3 ml) was added dropwise a solution of dimethylsulfoxide (123 mg) in dichloromethane (0.25 ml) at −78° C. under nitrogen atmosphere. After 15 minutes, (2R)-1-[3,5-bis(trifluoromethyl)benzoyl]-2-(3,4-dimethylbenzyl)-4-[2-(2-hydroxyethoxy)ethyl]piperazine (317 mg) was added at the same temperature. After 15 minutes, the resulting mixture was stirred at −45° C. for 1 hour. Triethylamine (446 mg) was added at −45° C., and the whole was stirred at 0° C. for 20 minutes and then treated with aqueous solution of ammonium chloride (2 ml). The organic layer was separated and dried over magnesium sulfate. After evaporation of the solvent, the resulting residue was purified by column chromatography on silica gel using ethyl acetate as eluent to afford (2R)-1-[3,5-bis (trifluoromethyl)benzoyl]-2-(3,4-dimethylbenzyl)-4-[2-(formylmethoxy)ethyl]piperazine (171 mg).

IR (Neat): 3450, 1740, 1640, 1440, 1280, 1130 cm$^{-1}$ NMR (DMSO-d$_6$, δ): 1.91–4.91 (22H, m), 6.53–8.20 (6H, m) MASS: 351 (M+H)$^+$

EXAMPLE 21

To a stirred mixture of 3,3-dimethylmorpholine hydrochloride (63 mg) and triethylamine (42 mg) in dichloromethane (5 ml) were added (2R)-1-[3,5-bis (trifluoromethyl)benzoyl]-2-(3,4-dimethylbenzyl)-4-[2-(formylmethoxy)ethyl]piperazine (200 mg) and sodium triacetoxyborohydride (120 mg) at room temperature. The resulting mixture was stirred for 1 hour and then treated with aqueous sodium bicarbonate solution. The organic layer was separated and dried over magnesium sulfate. After evaporation of the solvent, the residue was purified by column chromatography on silica gel using dichloromethanemethanol (10:1) as eluent and treated with 4N hydrogen chloride in ethyl acetate to give (2R)-1-[3,5-bis(trifluoromethyl) benzoyl]-2-(3,4-dimethylbenzyl)-4-[2-[2-(3,3-dimethylmorpholino)ethoxy]ethyl]piperazine dihydrochloride (193 mg) as a powder.

$[\alpha]_D^{23}$: −18.20° (C=0.50, MeOH) IR (Neat): 3450, 2600, 1640, 1430, 1280, 1140 cm$^{-1}$ NMR (DMSO-d$_6$, δ): 1.33 (6H, s), 2.04–5.23 (29H, m), 6.60–8.26 (6H, m) MASS: 630 (M+H)$^+$ (free) Elemental Analysis Calcd. for C$_{32}$H$_{41}$F$_6$N$_3$O$_3$.2HCl.3.32H$_2$O: C, 50.41; H, 6.56; N, 5.51. Found: C, 50.41; H, 6.29; N, 5.31.

EXAMPLE 22

The following compound was obtained according to a similar manner to that of Example 21.

(2R)-1-[3,5-Bis(trifluoromethyl)benzoyl]-2-(3,4-dimethylbenzyl)-4-[2-(2-morpholinoethoxy)ethyl] piperazine dihydrochloride $[\alpha]_D^{23}$: −21.4° (C=0.50, MeOH) IR (Neat): 3450, 2600, 1640, 1430, 1280, 1180, 1135 cm$^{-1}$ NMR (DMSO-d$_6$, δ): 2.08–5.20 (31H, m), 6.60–8.24 (6H, m) MASS: 602 (M+H)$^+$ (free) Elemental Analysis Calcd. for C$_{30}$H$_{37}$F$_6$N$_3$O$_3$.2HCl.2.66H$_2$O: C, 49.87; H, 6.18; N, 5.82. Found: C, 49.87; H, 6.25; N, 5.65.

EXAMPLE 23

A mixture of (2R)-1-[3,5-bis(trifluoromethyl)benzoyl]-2-[(1H-indol-3-yl)methyl]-4-(3-methylsulfonyloxypropyl) piperazine (250 mg), 4-aminothiomorpholine (90 mg) and sodium carbonate (180 mg) in methanol (5 ml) was stirred at reflux temperature for 3 hours. The reaction mixture was filtered and the filtrate was evaporated under reduced pressure. The residue was purified by column chromatography on silica gel using ethyl acetate-methanol (10:1) as eluent and treated with 4N hydrogen chloride in ethyl acetate (3 ml) to give (2R)-1-[3,5-bis(trifluoromethyl)benzoyl]-2-[(1H-indol-3-yl)methyl]-4-[3-(thiomorpholinoamino)propyl] piperazine dihydrochloride (62 mg) as a powder.

$[\alpha]_D^{27}$: −5.80° (C=0.50, MeOH) IR (Neat): 3300, 2500, 1630, 1420, 1275, 1130 cm$^{-1}$ NMR (DMSO-d$_6$, δ): 2.03–5.20 (23H, m), 6.60–8.24 (8H, m), 10.95 (1H, s)

MASS: 614 (M+H)+ (free) Elemental Analysis Calcd. for $C_{29}H_{35}Cl_2F_6N_5OS.3H_2O$: C, 47.10; H, 5.37; N, 8.88. Found: C, 47.03; H, 5.58; N, 9.46.

EXAMPLE 24

A mixture of (2R)-1-[3,5-bis(trifluoromethyl)benzoyl]-2-(3,4-dimethylbenzyl)-4-(2-methylsulfonyloxyethyl) piperazine (200 mg), 3-hydroxymethylpiperidine (44 mg) and triethylamine (73 mg) in methanol (5 ml) was stirred at reflux temperature for 2.5 hours. The reaction mixture was evaporated under reduced pressure and the residue was partitioned between ethyl acetate (30 ml) and water (10 ml). The organic layer was dried over magnesium sulfate and then evaporated under reduced pressure. The obtained residue was purified by column chromatography on silica gel using dichloromethanemethanol (10:1) as eluent and treated with 4N hydrogen chloride in ethyl acetate (0.2 ml) to give (2R)-1-[3,5-bis(trifluoromethyl)benzoyl]-2-(3,4-dimethylbenzyl)-4-[2-(3-hydroxymethylpiperidino)ethyl] piperazine dihydrochloride (85 mg).

$[\alpha]_D^{25}$: −5.30° (C=0.50, MeOH) IR (Neat) 3350, 2500, 1640, 1420, 1280, 1180, 1130 cm$^{-1}$ NMR (DMSO-d$_6$, δ): 1.0–5.20 (30H, m), 6.66–8.31 (6H, m) MASS: 586 (M+H)+ (free) Elemental Analysis Calcd. for $C_{30}H_{39}C_2F_6N_3O_2.3H_2O$: C, 50.58; H, 6.36; N, 5.90. Found: C, 50.58; H, 6.24; N, 5.87.

EXAMPLE 25

A mixture of (2R)-1-[3,5-bis(trifluoromethyl)benzoyl]-4-(4-chloro-2-butynyl)-2-(2-naphthylmethyl)piperazine (600 mg), 3,3-dimethylmorpholine hydrochloride (197 mg) and potassium carbonate (420 mg) in N,N-dimethylformamide (10 ml) was stirred at room temperature in the presence of potassium iodide (10 mg) for 2 days. The reaction mixture was partitioned between ethyl acetate (50 ml) and water (100 ml) and the organic layer was separated, washed with brine and dried over magnesium sulfate. After evaporation of the solvent, the residue was purified by column chromatography on silica gel using a mixture of ethyl acetate-hexane (10:1). The obtained product was dissolved in ethyl acetate and treated with 4N hydrogen chloride in ethyl acetate to give (2R)-1-[3,5-bis(trifluoromethyl)benzoyl]-4-[4-(3,3-dimethylmorpholino)-2-butynyl]-2-(2-naphthylmethyl)piperazine dihydrochloride (360 mg).

IR (KBr): 3401, 2929, 2578, 2512, 1644, 1284, 1135 cm$^{-1}$ NMR (DMSO-d$_6$, δ): 1.32 (3H, s), 1.39 (3H, s), 3.0–5.4 (19H, m), 7.0–8.2 (10H, m) MASS: 632 (M+H)+ (free) Elemental Analysis Calcd. for $C_{34}H_{37}Cl_2F_6N_3O_2.2.5H_2O$: C, 54.48; H, 5.65; N, 5.61. Found: C, 54.25; H, 5.53; N, 5.39.

EXAMPLE 26

Acetic anhydride (209 mg) was added to formic acid (94 mg). The resulting mixture was allowed to warm at 50° C. for 30 minutes and then added to (2R)-1-[3,5-bis(trifluoromethyl)benzoyl]-2-(3,4-dimethylbenzyl)-4-[3-(morpholinoamino)propyl]piperazine (200 mg) at room temperature. The whole was stirred overnight and then evaporated under reduced pressure. The obtained residue was dissolved in ethyl acetate and treated with 4N hydrogen chloride in ethyl acetate (0.2 ml) to give (2R)-1-[3,5-bis(trifluoromethyl)benzoyl]-2-(3,4-dimethylbenzyl)-4-[(3-(N-formylmorpholinoamino)propyl]piperazine hydrochloride (112 mg).

$[\alpha]_D^{23}$: −16.3° (C=0.50, MeOH) IR (Neat) 3450, 2800, 2620, 1660, 1430, 1280, 1185, 1140 cm$^{-1}$ NMR (DMSO-d$_6$, δ): 1.94–5.16 (29H, m), 6.62–8.35 (7H, m) MASS: 615 (M+H)+ (free) Elemental Analysis Calcd. for $C_{30}H_{37}ClF_6N_4O_3.1.36H_2O$: C, 53.34; H, 5.93; N, 8.29. Found: C, 53.33; H, 5.79; N, 8.06.

EXAMPLE 27

To a mixture of (2R)-1-[3,5-bis(trifluoromethyl)benzoyl]-2-(3,4-dimethylbenzyl)piperazine (3.71 g) and 4-formyl-1-(triphenylmethyl)pyrazole (3.66 g) in 1,2-dichloroethane (80 ml) was added sodium triacetoxyborohydride (2.86 g). After stirring at room temperature for 3 hours, aqueous sodium bicarbonate solution was added to the mixture and the mixture was extracted with ethyl acetate. The extract was washed with brine, dried over magnesium sulfate and evaporated under reduced pressure. The resulting residue was dissolved in dichloromethane (40 ml) and added to a mixture of trifluoroacetic acid (30 ml) and anisole (15 ml). After stirring for 7.5 hours at room temperature, the mixture was quenched with 10% sodium hydroxide (150 ml) and aqueous sodium bicarbonate and extracted with dichloromethane. The extract was washed with aqueous sodium bicarbonate solution and brine successively, dried over magnesium sulfate, and evaporated under reduced pressure. The residue was purified by column chromatography on silica gel using a mixture of ethyl acetate and hexane (3:7) to give (2R)-1-[3,5-bis(trifluoromethyl)benzoyl]-2-(3,4-dimethylbenzyl)-4-(4-pyrazolylmethyl)piperazine (2.84 g).

NMR (DMSO-d$_6$, δ): 2.04–2.14 (6H, m), 2.60–4.76 (11H, m), 6.49–6.54 (1H, m), 6.86–6.96 (2H, m), 7.45 (2H, br s), 7.64–7.68 (2H, m), 8.14 (1H, m) MASS: 525 (M+H)+

EXAMPLE 28

Potassium carbonate (158 mg) and 2-bromoethanol (0.045 ml) were added to a solution of (2R)-1-[3,5-bis(trifluoromethyl)benzoyl]-2-(3,4-dimethylbenzyl)-4-(4-pyrazolylmethyl)piperazine (300 mg) in N,N-dimethylformamide (3 ml) at room temperature with stirring. After stirring at 100° C. for 5 hours, the reaction mixture was poured into water and extracted with ethyl acetate. The organic layer was washed with brine, dried over magnesium sulfate, and evaporated under reduced pressure. The obtained residue was purified by column chromatography (30 ml) on silica gel using a mixture of ethyl acetate and hexane (3:7) to give (2R)-1-[3,5-bis(trifluoromethyl) benzoyl]-2-(3,4-dimethylbenzyl)-4-[[1-(2-hydroxyethyl)-1H-pyrazol-4-yl]methyl]piperazine (255.2 mg).

IR (KBr): 1640 cm$^{-1}$ NMR (DMSO-d$_6$, δ): 2.04–2.15 (6H, m), 2.60–4.80 (11H, m), 3.67–3.75 (2H, m), 4.10 (2H, t, J=5.7 Hz), 4.86 (1H, t, J=5.3 Hz), 6.50–6.56 (1H, m), 6.90–6.98 (2H, m), 7.36 (1H, br s), 7.43 (1H, br s), 7.61 (1H, br s), 7.67 (1H, br s), 8.13 (1H, br s) MASS: 569 (M+H)+

EXAMPLE 29

To a solution of (2R)-1-[3,5-bis(trifluoromethyl) benzoyl]-2-(3,4-dimethylbenzyl)-4-[[1-(2-hydroxyethyl)-1H-pyrazol-4-yl]methyl]piperazine (152 mg) in ethyl acetate (2 ml) was added triethylamine (0.048 ml) and methanesulfonyl chloride (0.027 ml) at room temperature. After stirring for 10 minutes, the mixture was quenched with water and extracted with ethyl acetate. The combined extracts were washed with water and brine successively, dried over magnesium sulfate, and evaporated under reduced pressure. The obtained residue was dissolved in N,N-dimethylformamide (2 ml) and added morpholine (0.028 ml), potassium carbonate (74 mg) and potassium iodide (13 mg). After stirring at 70° C. for 6 hours, the mixture was quenched with water and extracted with ethyl acetate. The combined extracts were washed with water and brine successively, dried over magnesium sulfate, and evaporated under reduced pressure. The obtained residue was dissolved in ethyl acetate and treated with 4N hydrogen chloride in ethyl acetate (0.2 ml) at room temperature. The mixture was added hexane, filtered, and dried over reduced pressure to give (2R)-1-[3,5-bis(trifluoromethyl)benzoyl]-2-(3,4-dimethylbenzyl)-4-[[1-(2-morpholinoethyl)-1H-pyrazol-4-yl]methyl]piperazine dihydrochloride (188.7 mg) as a solid.

mp: 115–116° C. $[\alpha]_D^{25}$: −9.70° (C=0.50, MeOH) IR (KBr): 1640 cm$^{-1}$ NMR (DMSO-d$_6$, δ): 2.06–2.16 (6H, m), 2.85–5.00 (23H, m), 6.60–6.64 (1H, m), 6.91–7.08 (2H, m), 7.57 (1H, s), 7.74 (1H, br s), 7.78 (1H, br s), 8.10 (1H, br s), 8.18 (1H, br s) MASS: 638 (M+H)$^+$ (free)

EXAMPLE 30

A solution of (2R)-1-[3,5-bis(trifluoromethyl)benzoyl]-4-(4-chloro-2-butynyl)-2-(2-naphthylmethyl)piperazine (200 mg), 3-(aminomethyl)pyridine (47 mg), and triethylamine (0.08 ml) in acetonitrile (2 ml) was stirred under reflux for 3 hours and evaporated under reduced pressure. The obtained residue was purified by column chromatography on silica gel (10 ml) using dichloromethane-methanol (30:1) as eluent. The obtained oil was dissolved in ethyl acetate and treated with a solution of,4N hydrogen chloride in ethyl acetate. The mixture was evaporated under reduced pressure to give (2R)-1-[3,5-bis(trifluoromethyl)benzoyl]-4-[4-(3-pyridylmethylamino)-2-butynyl]-2-(2-naphthylmethyl)piperazine trihydrochloride (60 mg) as a powder.

$[\alpha]_D^{29}$: −20.80° (C=0.25, MeOH) IR (Neat): 3650–3100, 2750–1950, 1630, 1273, 1122 cm$^{-1}$ NMR (DMSO-d$_6$, δ): 2.60–5.30 (16H, m), 7.00–9.10 (14H, m) MASS: 625 (M+H)$^+$ (free) Elemental Analysis Calcd. for C$_{34}$H$_{33}$Cl$_3$F$_6$N$_4$O.3.3H$_2$O: C, 51.43; H, 5.03; N, 7.06. Found: C, 51.42; H, 4.91; N, 6.78.

EXAMPLE 31

A mixture of (2R)-1-[3,5-bis(trifluoromethyl)benzoyl]-4-(4-chloro-2-butynyl)-2-(2-naphthylmethyl)piperazine (300 mg), cis-2,6-dimethylmorpholine (94 mg) and powdered potassium carbonate (210 mg) in dry N,N-dimethylformamide (5 ml) was stirred at room temperature overnight. The reaction mixture was poured into water (50 ml) and extracted with ethyl acetate. The extract was washed with brine and dried over magnesium sulfate. After evaporation of the solvent, the obtained residue was purified by column chromatography on silica gel using a mixture of ethyl acetate and hexane (4:1) as eluent. The obtained product was dissolved in ethyl acetate and treated with 4N hydrogen chloride in ethyl acetate to give (2R)-1-[3,5-bis(trifluoromethyl)benzoyl]-4-[4-(cis-2,6-dimethylmorpholino)-2-butynyl]-2-(2-naphthylmethyl)piperazine dihydrochloride (170 mg).

IR (KBr): 3428, 2931, 2559, 1644, 1432, 1282, 1184 cm$^{-1}$ NMR (DMSO-d$_6$, δ): 1.13 (3H, s), 1.16 (3H, s), 2.60–5.40 (21H, m), 7.00–8.15 (10H, m) MASS: 632 (M+H)$^+$ (free) Elemental Analysis Calcd. for C$_{34}$H$_{37}$Cl$_2$F$_6$N$_3$O$_2$.2H$_2$O: C, 55.14; H, 5.58; N, 5.67. Found: C, 54.89; H, 5.59; N, 5.31.

EXAMPLE 32

The following compound was obtained according to a similar manner to that of Example 31.

1,3-[Bis(trifluoromethyl)benzoyl]-4-[4-(2-methylthiazol-4-yl)methyl]-2-[(1H-indol-3-yl)methyl]piperazine hydrochloride NMR (DMSO-d$_6$, δ): 2.65 (3H, s), 3.00–5.20 (11H, m), 6.80–8.24 (9H, m), 10.93 (1H, br d) MASS: 567 (M+H)$^+$ (free)

EXAMPLE 33

To a stirred mixture of (2R)-[3,5-bis(trifluoromethyl)benzoyl]-2-(3,4-dimethylbenzyl)piperazine (943 mg) and potassium carbonate (880 mg) in dimethylformamide (10 ml) was added propargyl bromide (0.2 ml) at room temperature. After 1 hour, the reaction mixture was poured into water (100 ml) and extracted with ethyl acetate. The extract was washed with brine and concentrated under reduced pressure. The obtained residue was purified by column chromatography on silica gel using a mixture of hexane and ethyl acetate (5:1) as eluent to give (2R)-1-[3,5-bis(trifluoromethyl)benzoyl]-2-(3,4-dimethylbenzyl)-4-propargylpiperazine (1.09 g) as an oil.

NMR (DMSO-d$_6$, δ): 2.00–2.20 (6H, m), 2.20–5.00 (12H, m), 6.60–8.20 (6H, m) MASS: 483 (M+H)$^+$

EXAMPLE 34

A mixture of (2R)-[3,5-bis(trifluoromethyl)benzoyl]-2-(3,4-dimethylbenzyl)-4-propargylpiperazine (286 mg), (3S)-3-isopropylmorpholine hydrochloride (118 mg) and N,N-diisopropylamine (92 mg) in dioxane (3 ml) was stirred at room temperature. Paraformaldehyde (22 mg) and copper(I) chloride (10 mg) were added and the whole was stirred for 30 minutes and then heated at 80° C. for 4 hours. The reaction mixture was filtered and the filtrate was concentrated under reduced pressure. The obtained residue was purified by column chromatography on silica gel using a mixture of hexane and ethyl acetate (1:1) as eluent. The obtained product was dissolved in ethyl acetate and treated with 4N hydrogen chloride in ethyl acetate to give (2R)-1-[3,5-bis(trifluoromethyl)benzoyl]-4-[4-((3S)-3-isopropylmorpholino)-2-butynyl]-2-(3,4-dimethylbenzyl)piperazine dihydrochloride (190 mg).

IR (KBr): 3438, 2971, 2551, 1644, 1438, 1282, 1216, 1135 cm$^{-1}$ NMR (DMSO-d$_6$, δ): 1.01 (6H, d, J=6.8 Hz), 2.09–2.17 (6H, m), 2.36 (1H, m), 2.60–5.30 (22H, m), 6.60–8.30 (6H, m) MASS: 624 (M+H)$^+$ (free)

EXAMPLE 35

A mixture of (2R)-1-[3,5-bis(trifluoromethyl)benzoyl]-4-(4-chloro-2-butenyl)-2-(3,4-dimethylbenzyl)piperazine (150 mg), (3S)-3-isopropylmorpholine hydrochloride (47 mg) and powdered potassium carbonate (117 mg) in dry N,N-dimethylformamide (1 ml) was stirred at 50° C. for 1.5 hours. The reaction mixture was poured into water (10 ml) and extracted with ethyl acetate. The extract was washed with brine and dried over magnesium sulfate. After evaporation of the solvent, the obtained residue was purified by column chromatography on silica gel using ethyl acetate as eluent. The obtained product was dissolved in ethyl acetate and treated with 4N hydrogen chloride in ethyl acetate to give (2R)-1-[3,5-bis(trifluoromethyl)benzoyl]-4-[4-((3S)-3-isopropylmorpholino)-2-butenyl]-2-1(3,4-dimethylbenzyl)piperazine dihydrochloride (110 mg).

IR (KBr): 3430, 2971, 2661, 1644, 1434, 1280, 1135, 985, 680 cm$^{-1}$ NMR (DMSO-d$_6$, δ): 1.01 (6H, m), 2.00–2.20 (6H, m), 2.40 (1H, m), 2.60–5.20 (24H, m), 6.60–8.20 (6H, m) MASS: 626 (M+H)$^+$ (free) Elemental Analysis Calcd. for C$_{33}$H$_{43}$Cl$_2$F$_6$N$_3$O$_2$.3H$_2$O: C, 52.66; H, 6.56; N, 5.58. Found: C, 52.45; H, 6.55; N, 5.49.

EXAMPLE 36

To a stirred solution of (2R)-[3,5-bis(trifluoromethyl)benzoyl]-2-(3,4-dimethylbenzyl)-4-[2-((3R,3S)-3- hydroxymethylpiperidino)ethyl]piperazine (133 mg) in N,N-dimethyl-formamide (1 ml) was added 60% sodium hydride (109 mg) at ice-salt bath temperature. A solution of ethyl iodide (53 mg) in N,N-dimethylformamide (0.5 ml) was added and the whole was stirred for 15 minutes and then at room temperature for 1 hour. The reaction mixture was poured into water (20 ml) and extracted with ethyl acetate. The extract was washed with brine and concentrated under reduced pressure. The obtained residue was purified by column chromatography on silica gel using a mixture of dichloromethane and methanol (10:1) as eluent. The obtained product was dissolved in ethyl acetate and treated with 4N hydrogen chloride in ethyl acetate to give (2R)-[3,5-bis(trifluoromethyl)benzoyl]-2-(3,4-dimethylbenzyl)-4-[2-((3R,3S)-3-ethoxymethylpiperidino)ethyl]piperazine dihydrochoride (101 mg).

$[\alpha]_D^{23}$: −8.0° (C=0.50, MeOH) IR (KBr): 3400, 2630, 2540, 1645, 1435, 1280, 1180, 1135 cm$^{-1}$ NMR (DMSO-d$_6$, δ): 0.72–5.24 (32H, m), 1.12 (3H, t), 6.62–8.26 (6H, m) MASS: 614 (M+H)$^+$ (free)

EXAMPLE 37

The requisite mesylate was prepared by the treatment of (2R)-1-[3,5-bis(trifluoromethyl)benzoyl]-2-(3,4-dimethylbenzyl)-4-(2-hydroxyethyl)piperazine with methanesulfonyl chloride. A mixture of the mesylate (200 mg) and 4-hydroxymethylpiperidine hydrochloride (66 mg) in methanol (1 ml) was heated at reflux in the presence of potassium carbonate (150 mg). After 3 hours, the reaction mixture was filtered and the filtrate was concentrated under reduced pressure. The obtained residue was purified by column chromatography on silica gel using a mixture of dichloromethane and methanol (5:1) as eluent. The obtained product was dissolved in ethyl acetate and treated with 4N hydrogen chloride in ethyl acetate to give (2R)-1-[3,5-bis(trifluoromethyl)benzoyl]-4-[2-(4-hydroxymethylpiperidino)ethyl]-2-(3,4-dimethylbenzyl)piperazine dihydrochloride (32 mg).

$[\alpha]_D^{26}$: −5.8° (C=0.50, MeOH) IR (KBr): 3370, 2600, 1645, 1430, 1280, 1180, 1140 cm$^{-1}$ NMR (DMSO-d$_6$, δ): 1.40–5.24 (30H, m), 6.60–8.24 (6H, m), 8.45 (1H, s) MASS: 586 (M+H)$^+$ (free) Elemental Analysis Calcd. for $C_{30}H_{37}F_6N_3O_2$.2HCl.4.85H$_2$O: C, 48.36; H, 6.57; N, 5.64. Found: C, 48.31; H, 5.95; N, 4.96.

EXAMPLE 38

A mixture of (2R)-1-[3,5-bis(trifluoromethyl)benzoyl]-4-(4-chloro-2-butynyl)-2-(3,4-dimethylbenzyl)piperazine (150 mg), (3S)-3-ethylmorpholine hydrochloride (47 mg) and powdered potassium carbonate (117 mg) in dry N,N-dimethylformamide (1 ml) was stirred at 50° C. for 1.5 hours. The reaction mixture was poured into water (10 ml) and extracted with ethyl acetate. The extract was washed with brine and dried over magnesium sulfate. After evaporation of the solvent, the obtained residue was purified by column chromatography on silica gel using ethyl acetate as eluent. The obtained product was dissolved in ethyl acetate and treated with 4N hydrogen chloride in ethyl acetate to give (2R)-1-[3,5-bis(trifluoromethyl)benzoyl]-4-[4-((3S)-3-ethylmorpholino)-2-butynyl]-2-(3,4-dimethylbenzyl)piperazine dihydrochloride (177 mg).

$[\alpha]_D^{26}$: 4.8° (C=0.50, MeOH) IR (KBr): 3430, 2580, 1645, 1435, 1280,. 1180, 1135 cm$^{-1}$ NMR (DMSO-d$_6$, δ): 1.27 (3H, t), 1.45–5.20 (28H, m), 6.64–8.28 (6H, m) MASS: 610 (M+H)$^+$ (free) Elemental Analysis Calcd. for $C_{32}H_{37}F_6N_3O_2$.2HCl.3.5H$_2$O: C, 51.55; H, 6.22; N, 5.64. Found: C, 51.61; H, 6.02; N, 5.60.

EXAMPLE 39

The requisite mesylate was prepared by the treatment of (2R)-1-[3,5-bis(trifluoromethyl)benzoyl]-2-(3,4-dimethylbenzyl)-4-(2-hydroxyethyl)piperazine (150 mg) with methanesulfonyl chloride (37 mg). A mixture of the mesylate and (3S)-3-ethylmorpholine hydrochloride (51 mg) in N,N-dimethylformamide (1 ml) was heated at 50° C. in the presence of potassium carbonate (85 mg). After 2 hours, the reaction mixture was poured into water (10 ml) and extracted with ethyl acetate. The extract was washed with brine and dried over magnesium sulfate. After evaporation of the solvent, the obtained residue was purified by column chromatography on silica gel using ethyl acetate as eluent. The obtained product was dissolved in ethyl acetate and treated with 4N hydrogen chloride in ethyl acetate to give (2R)-1-[3,5-bis(trifluoromethyl)benzoyl]-4-[2-((3S)-3-ethylmorpholino)ethyl]-2-(3,4-dimethylbenzyl)piperazine dihydrochloride (45 mg).

$[\alpha]_D^{24}$: 1.60° (C=0.50, MeOH) IR (KBr): 3430, 2610, 1645, 1435, 1280, 1180, 1135 cm$^{-1}$ NMR (DMSO-d$_6$, δ): 0.95 (3H, s), 1.16–5.20 (28H, m), 6.64–8.24 (6H, m) MASS: 586 (M+H)$^+$ (free) Elemental Analysis Calcd. for $C_{30}H_{37}F_6N_3O_2$.2HCl.1.8H$_2$O: C, 52.15; H, 6.21; N, 6.08. Found: C, 52.15; H, 6.42; N, 6.00.

EXAMPLE 40

A mixture of (2R)-1-[3,5-bis(trifluoromethyl)benzoyl]-4-(2-methylsulfonyloxyethyl)-2-(2-naphthylmethyl)piperazine (200 mg), 3-(N-methylaminomethyl)pyridine dihydrochloride (73 mg) and triethylamine (120 mg) in dry methanol (5 ml) was refluxed for 4 hours. The reaction mixture was concentrated under reduced pressure and the resulting residue was partitioned between ethyl acetate and aqueous sodium bicarbonate solution. The organic layer was washed with brine and dried over magnesium sulfate. After evaporation of the solvent, the residue was purified by column chromatography on silica gel using a mixture of ethyl acetate and methanol (10:1) as eluent to afford an oily product, which was treated with 4N hydrogen chloride in ethyl acetate (0.5 ml) to give (2R)-1-[3,5-bis(trifluoromethyl)benzoyl]-4-[2-[(N-methyl-N-(3-pyridylmethyl)amino]ethyl]-2-(2-naphthylmethyl)piperazine dihydrochloride (78 mg).

$[\alpha]_D^{25}$: −12.9° (C=0.50, MeOH) IR (KBr): 3410, 2600, 1640, 1430, 1280, 1180, 1135 cm$^{-1}$ NMR (DMSO-d$_6$, δ): 2.40–5.28 (15H, m), 2.74 (3H, s), 7.00–9.10 (14H, m) MASS: 615 (M+H)$^+$ (free) Elemental Analysis Calcd. for $C_{33}H_{32}F_6N_4O$.2HCl.4.6H$_2$O: C, 51.45; H, 5.65; N, 7.27. Found: C, 51.40; H, 5.37; N, 7.07.

EXAMPLE 41

The following compound was obtained according to a similar manner to that of Example 40.

(2R)-1-[3,5-Bis(trifluoromethyl)benzoyl]-2-[(1H-indol-3-yl)methyl]-4-[2-[N-methyl-N-(3-pyridylmethyl)amino]ethyl]piperazine dihydrochloride $[\alpha]_D^{24}$: −0.8° (C=0.50, MeOH) IR (KBr): 3400, 2600, 1640, 1280, 1180, 1135 cm$^{-1}$ NMR (DMSO-d$_6$, δ): 1.12–5.20 (15H, m), 2.84 (3H, s), 6.63–9.00 (12H, m), 10,95 (1H, s) MASS: 604 (M+H)$^+$Elemental Analysis Calcd. for $C_{31}H_{31}F_6N_5O$.2HCl.4.5H$_2$O: C, 49.15, H 5.59; N, 9.24. Found: C, 49.19; H, 5.41; N, 9.08.

EXAMPLE 42

To a stirred mixture of (2R)-1-[3,5-[bis(trifluoromethyl)benzoyl]-2-[(1H-indol-3-yl)methyl]-4-[N-(1-piperazinyl)

carbamoylmethyl]piperazine dihydrochloride (500 mg) and triethylamine (302 mg) in tetrahydrofuran (10 ml) was added a solution of benzyl 4-bromobutanoate (192 mg) in tetrahydrofuran (2 ml) at room temperature for 24 hours. As a part of starting material remained, the reaction mixture was filtered and the filtrate was concentrated under reduced pressure. To the resulting residue were added benzyl 4-bromobutanoate (192 mg), potassium carbonate (310 mg) and N,N-dimethylformamide (2 ml). The whole was stirred at room temperature for 7 hours and then diluted with ethyl acetate and filtered. The filtrate was washed with brine and dried over magnesium sulfate. After evaporation of solvent, the residue was purified by column chromatography on a silica gel using a mixture of ethyl acetate and methanol (5:1) as eluent to afford (2R)-1-[3,5-bis(trifluoromethyl)benzoyl]-4-[N-[4-(3-benzyloxycarbonylpropyl)piperazin-1-yl]carbamoylmethyl]-2-[(1H-indol-3-yl)methyl]piperazine (296 mg).

IR (Neat): 3250, 1720, 1670, 1630, 1430, 1350, 1270, 1120 cm$^{-1}$ NMR (CDCl$_3$, $\delta$): 1.60–3.66 (25H, m), 5.10 (2H, s), 6.80–7.86 (8H, m), 7.32 (5H, s), 8.21 (1H, s) MASS: 773 (M+H)$^+$

EXAMPLE 43

A mixture of (2R)-1-[3,5-bis(trifluoromethyl)benzoyl]-4-[N-[4-(3-benzyloxycarbonylpropyl)piperazin-1-yl]carbamoylmethyl]-2-[(1H-indol-3-yl)methyl]piperazine (1.3 g), ammonium formate (265 mg) and 10% palladium on activated carbon (130 mg) in water (2.5 ml) and ethanol (25 ml) was heated at 70° C. with stirring under a nitrogen atmosphere. After 1 hour, the reaction mixture was filtered and the filtrate was concentrated under reduced pressure. The product was triturated with ethyl ether to give (2R)-1-[3,5-bis(trifluoromethyl)benzoyl]-4-[N-[4-(3-carboxypropyl)piperazin-1-yl]carbamoylmethyl]-2-[(1H-indol-3-yl)methyl]piperazine (1.19 g) as a powder.

[$\alpha$]$_D^{28}$: -18.60° (C=0.50, MeOH) IR (Neat): 3200, 1680, 1620, 1425, 1275, 1120 cm$^{-1}$ NMR (CDCl$_3$, $\delta$): 1.72–4.60 (25H, m), 6.71–7.93 (8H, m) MASS: 683 (M+H)$^+$

EXAMPLE 44

The following compounds were obtained according to a similar manner to that of Example 5-(1).
(1) (2R)-1-[3,5-Bis(trifluoromethyl)benzoyl]-4-[(2E)-3-[(3R)-4-(tert-butoxycarbonyl)morpholin-3-yl]-2-propenyl]-2-(3,4-dimethylbenzyl)piperazine IR (Neat): 2973, 1697, 1645 cm$^{-1}$ NMR (CDCl$_3$, $\delta$): 1.39 (9H, s), 2.00–2.16 (6H, m), 2.48–5.00 (18H, m), 5.40–5.80 (2H, m), 6.60–6.80 (1H, m), 6.90–7.20 (2H, m), 7.30–7.70 (3H, m), 8.13 (1H, br s) MASS: 670 (M+H)$^+$
(2) (2R)-1-[3,5-Bis(trifluoromethyl)benzoyl]-4-[(2E)-3-[(2R,2S)-4-(tert-butoxycarbonyl)morpholin-2-yl]-2-propenyl]-2-(3,4-dimethylbenzyl)piperazine NMR (DMSO-d$_6$, $\delta$): 1.41 (9H, s), 2.08–2.16 (6H, m), 2.50–4.80 (18H, m), 5.55–5.85 (2H, m), 6.60–6.80 (1H, m), 6.90–7.20 (2H, m), 7.30–7.70 (2H, m), 8.13 (1H, br s) MASS: 670 (M+H)$^+$

EXAMPLE 45

A solution of (2R)-1-[3,5-bis(trifluoromethyl)benzoyl]-4-[(2E)-3-[(3R)-4-(tert-butoxycarbonyl)morpholin-3-yl]-2-propenyl]-2-(3,4-dimethylbenzyl)piperazine (1.36 g) in ethyl acetate (13 ml) was treated 4N hydrogen chloride in ethyl acetate (3.12 ml) at room temperature for 18 hours and then at 40° C. for 5 hours. The solution was diluted with hexane and stirred for 1 hour. The resulting precipitate was collected by filtration and dried under reduced pressure to give (2R)-1-[3,5-bis(trifluoromethyl)benzoyl]-2-(3,4-dimethylbenzyl)-4-[(2E)-3-[(3R)-3-morpholinyl]-2-propenyl]piperazine dihydrochloride (1.11 g) as a white powder.

mp: 225–232° C. [$\alpha$]$_D^{25}$: -12.00° (C=0.50, MeOH) IR (KBr): 1645 cm$^{-1}$ NMR (DMSO-d$_6$, $\delta$): 2.10–2.18 (6H, m), 2.70–5.10 (18H, m), 5.80–6.25 (2H, m), 6.60–6.70 (1H, m), 6.90–7.20 (2H, m), 7.39–7.69 (2H, m), 8.15–8.20 (1H, m), 9.60–10.0 (2H, m) MASS: 570 (M+H)$^+$ (free) Elemental Analysis Calcd. for C$_{29}$H$_{33}$F$_6$N$_3$O$_2$.2HCl.1.0H$_2$O: C, 52.73; H, 5.65; N, 6.36. Found: C, 52.65; H, 5.76; N, 6.26.

EXAMPLE 46

To a solution of (2R)-1-[3,5-bis(trifluoromethyl)benzoyl]-2-(3,4-dimethylbenzyl)-4-(4-pyrazolylmethyl)piperazine (500 mg) and tert-butyl bromoacetate (225 mg) in N,N-dimethylformamide (7.5 ml) was added potassium carbonate (390 mg), and the mixture was stirred at 60° C. for 7 hours. Water was added to the mixture and the resulting mixture was extracted with ethyl acetate. The organic layer was washed with brine, dried over magnesium sulfate, evaporated under reduced pressure, and purified by column chromatography on a silica gel using a mixture of ethyl acetate and hexane (1:1) as eluent to give (2R)-1-[3,5-bis(trifluoromethyl)benzoyl]-4-[[1-(tert-butoxycarbonyl-methyl)-1H-pyrazol-4-yl]methyl]-2-(3,4-dimethylbenzyl)piperazine as an oil.

NMR (DMSO-d$_6$, $\delta$): 1.01 (9H, s), 2.05–2.15 (6H, s), 2.52–4.90 (11H, m), 4.90 (2H, s), 6.53–6.58 (1H, m), 6.90–7.00 (2H, m), 7.41 (2H, s), 7.65 (2H, s), 8.13 (1H, br s) MASS: 639 (M+H)$^+$

EXAMPLE 47

A solution of (2R)-1-[3,5-bis(trifluoromethyl)benzoyl]-4-[[1-(tert-butoxycarbonylmethyl)-1H-pyrazol-4-yl]methyl]-2-(3,4-dimethylbenzyl)piperazine (425 mg) in dichloromethane (2.5 ml) was treated with trifluoroacetic acid (2.5 ml) at room temperature for 1 hour. The mixture was adjusted to pH 7.4 with aqueous sodium bicarbonate solution and evaporated under reduced pressure. The residue was washed with a mixture of dichloromethane and methanol (9:1), and the solution was evaporated under reduced pressure and purified by column chromatography on a silica gel using a mixture of methanol and chloroform (1:9) as eluent and subsequent crystallization from ethyl acetate, isopropyl ether, and hexane to give (2R)-1-[3,5-bis(trifluoromethyl)benzoyl]-4-[[1-(carboxymethyl)-1H-pyrazol-4-yl]methyl]-2-(3,4-dimethylbenzyl)piperazine (395 mg) as a white powder.

mp: 223–230° C. [$\alpha$]$_D^{25}$: -15.10° (C=0.50, MeOH) IR (KBr): 1683, 1604 cm$^{-1}$ NMR (DMSO-d$_6$, $\delta$): 2.06–2.15 (6H, m), 2.52–4.90 (11H, m), 4.54 (2H, s), 6.50–6.60 (1H, m), 6.90–7.00 (2H, m), 7.31 (1H, s), 7.40 (1H, s), 7.57–7.64 (2H, m), 8.14 (1H, s)

EXAMPLE 48

To a solution of (2R)-1-[3,5-bis(trifluoromethyl)benzoyl]-4-[[1-(carboxymethyl)-1H-pyrazol-4-yl]methyl]-2-(3,4-dimethylbenzyl)piperazine (120 mg) in tetrahydrofuran (1 ml) were added 1-hydroxybenzotriazole hydrate (176 mg), 1-ethyl-3-(3-dimethylaminopropyl)carbodiimide hydrochloride (240 mg) and morpholine (0.11 ml) at room temperature, and the mixture was stirred at room temperature overnight. The mixture was quenched with water, and extracted with ethyl acetate. The organic layer was washed with brine, dried over magnesium sulfate, and evaporated under reduced pressure. The residue was purified by column chromatography on a silica gel using a mixture of methanol and ethyl acetate (1:9) as eluent to give a crude oil (76.7 mg). The oil was dissolved in ethyl acetate (0.7 ml) and added 4N hydrogen chloride in ethyl acetate (0.15 ml) at room temperature. After the addition of isopropyl ether, the resulting precipitate was filtered off and dried under reduced pressure to give (2R)-1-[3,5-bis(trifluoromethyl)benzoyl]-2-(3,4-dimethylbenzyl)-4-[[1-(morpholinocarboxymethyl)-1H-pyrazol-4-yl]methyl]piperazine hydrochloride (40 mg) as a powder.

mp: 120–130° C. $[\alpha]_D^{25}$: −19.40° (C=0.25, MeOH) IR (KBr): 1649 cm$^{-1}$ NMR (DMSO-d$_6$, δ): 2.06–2.16 (6H, s), 2.52–5.00 (19H, m), 5.19 (2H, s), 6.55–6.62 (1H, m), 6.92–7.03 (2H, m), 7.44 (1H, s), 7.66–7.68 (2H, m), 7.92 (1H, br s), 8.19 (1H, br s) MASS: 652 (M+H)$^+$ (free) Elemental Analysis Calcd. for C$_{22}$H$_{35}$F$_6$N$_5$O$_3$.HCl.2.6H$_2$O: C, 52.30; H, 5.65; N, 9.53. Found: C, 52.58; H, 5.63; N, 9.22.

EXAMPLE 49

The following compound was obtained according to a similar manner to that of Example 34.

(2R)-1-[3,5-Bis(trifluoromethyl)benzoyl]-2-(3,4-dimethylbenzyl)-4-[4-[(3S)-3-(2-methylpropyl) morpholino]-2-butynyl]piperazine dihydrochloride mp: 125–138° C. $[\alpha]_D^{25}$: +13.90° (C=0.50, MeOH) IR (KBr): 1645 cm$^{-1}$ NMR (DMSO-d$_6$, δ): 0.80–1.80 (9H, m), 2.09–2.18 (6H, m), 2.83–5.13 (20H, m), 6.60–6.70 (1H, m), 6.96–7.14 (2H, m), 7.46 (1H, br s), 7.67 (1H, br s), 8.16 (1H, br s) MASS: 638 (M+H)$^+$ (free) Elemental Analysis Calcd. for C$_{34}$H$_{43}$Cl$_2$F$_6$N$_3$O$_2$.1.1H$_2$O: C, 55.91; H, 6.24; N, 5.75. Found: C, 56.24; H, 6.75; N, 5.74.

EXAMPLE 50

The following compound was obtained according to a similar manner to that of Example 31.

(2R)-1-[3,5-Bis(trifluoromethyl)benzoyl]-2-(3,4-dimethylbenzyl)-4-[4-(7-oxa-4-azaspiro[2.5]octan-4-yl]-2-butynyl]piperazine dihydrochloride $[\alpha]_D^{27.9}$: −9.70° (C=0.50, MeOH) IR (KBr): 3700–3000, 2700–2200, 1645, 1534, 1463, 1280, 1184 cm$^{-1}$ NMR (DMSO-d$_6$, δ): 0.90–1.00 (4H, m), 3.00–4.70 (19H, m), 6.60–8.20 (6H, m) MASS: 608 (M+H)$^+$ (free) Elemental Analysis Calcd. for C$_{32}$H$_{35}$F$_6$N$_3$O$_2$.2HCl.2H$_2$O: C, 53.64; H, 5.77; N, 5.86. Found: C, 53.92; H, 6.05; N, 5.61.

EXAMPLE 51

The following compounds were obtained according to a similar manner to that of Example 1-(1).

(1) (2R)-1-[3,5-Bis(trifluoromethyl)benzoyl]-2-[(1H-indol-3-yl)methyl]-4-[3-(4-methoxypyridin-3-yl)-2-propynyl]piperazine NMR (CDCl$_3$, δ): 2.00–5.20 (11H, m), 3.92 (3H, s), 6.80–8.00 (11H, m), 8.30 (1H, br s) MASS: 601 (M+H)$^+$ (free)

(2) (2R)-1-[3,5-Bis(trifluoromethyl)benzoyl]-2-(3,4-dimethylbenzyl)-4-[3-(4-methoxypyridin-3-yl)-2-propynyl]piperazine NMR (CDCl$_3$, δ): 2.00–5.20 (17H, m), 3.93 (3H, s), 6.60–8.80 (9H, m), 8.02 (1H, s), 8.30–8.50 (1H, m) MASS: 590 (M+H)$^+$

EXAMPLE 52

The following compounds were obtained according to a similar manner to that of Example 5-(2).

(1) (2R)-1-[3,5-Bis(trifluoromethyl)benzoyl]-2-[(1H-indol-3-yl)methyl]-4-[3-(4-methoxypyridin-3-yl)-2-propynyl]piperazine dihydrochloride mp: 162–167° C. $[\alpha]_D^{26.6}$: +4.90° (C=0.50, MeOH) IR (KBr): 3700–3300, 2700–2300, 1641, 1502, 1430, 1363, 1280 cm$^{-1}$ NMR (DMSO-d$_6$, δ): 3.00–5.20 (14H, m), 6.60–8.30 (9H, m), 8.80–9.90 (2H, m), 10.96 (1H, br s) MASS: 601 (M+H)$^+$ (free) Elemental Analysis Calcd. for C$_{31}$H$_{26}$F$_6$N$_4$O$_2$.2HCl.2.2H$_2$O: C, 52.16; H, 4.91; N, 8.32. Found: C, 52.21; H, 4.58; N, 7.86.

(2) (2R)-1-[3,5-Bis(trifluoromethyl)benzoyl]-2-(3,4-dimethylbenzyl)-4-[3-(4-methoxypyridin-3-yl)-2-propynyl]piperazine dihydrochloride mp: 150–153° C. $[\alpha]_D^{24.9}$: −7.45° (C=0.55, MeOH) IR (KBr): 3600–3300, 2700–2200, 1639, 1500, 1430, 1317, 1280 cm$^{-1}$ NMR (DMSO-d$_6$, δ): 2.00–2.20 (6H, m), 2.80–5.20 (11H, m), 6.60–7.80 (6H, m), 8.20 (1H, br s), 8.81–8.97 (2H, m) MASS: 590 (M+H)$^+$ (free) Elemental Analysis Calcd. for C$_{31}$H$_{29}$F$_6$N$_3$O$_2$.2HCl.2.2H$_2$O: C, 52.97; H, 5.27; N, 5.93. Found: C, 53.03; H, 5.08; N, 5.98.

EXAMPLE 53

The following compounds were obtained according to a similar manner to that of Example 3.

(1) (2R)-1-[3,5-Bis(trifluoromethyl)benzoyl]-2-[(1H-indol-3-yl)methyl]-4-[3-(4-methoxypyridin-3-yl)propyl]piperazine dihydrochloride mp: 165–170° C. $[\alpha]_D^{24.9}$: −1.91° (C=0.55, MeOH) IR (KBr):3700–2300, 1643, 1502, 1432, 1363, 1280, 1222 cm$^{-1}$ NMR (DMSO-d$_6$, δ): 2.00–2.30 (2H, n), 2.60–5.20 (16H, m), 6.60–8.30 (9H, m), 8.70–8.90 (2H, m), 10.95 (1H, br s), 11.60–11.80 (2H, m) MASS: 605 (M+H)$^+$ (free) Elemental Analysis Calcd. for C$_{31}$H$_{30}$F$_6$N$_4$O$_2$.2HCl.2.8H$_2$O: C, 51.15; H, 5.21; N, 7.70. Found: C, 51.11; H, 5.40; N, 7.61.

(2) (2R)-1-[3,5-Bis(trifluoromethyl)benzoyl]-2-(3,4-dimethylbenzyl)-4-[3-(4-methoxypyridin-3-yl)propyl]piperazine dihydrochloride mp: 159–168° C. $[\alpha]_D^{26.9}$: −10.91° (C=0.55, MeOH) IR (KBr): 3600–3300, 2700–2300, 1643, 1502, 1430, 1361, 1280 cm$^{-1}$ NMR (DMSO-d$_6$, δ): 2.00–5.20.(21H, m), 4.13 (3H, s), 6.60–7.80 (6H, m), 8.20–8.30 (1H, m), 8.70–8.90 (2H, m), 11.60–11.90 (2H, m) MASS: 594 (M+H)$^+$ (free) Elemental Analysis Calcd. for C$_{31}$H$_{33}$F$_6$N$_3$O$_2$.2HCl.2.4H$_2$O: C, 52.50; H, 5.97; N, 5.60. Found: C, 52.46; H, 5.65; N, 5.92.

EXAMPLE 54

A solution of (2R)-1-[3,5-bis(trifluoromethyl)benzoyl]-2-[(1H-indol-3-yl)methyl]-4-[3-[6-(tert-butoxycarbonyl-amino)pyridin-3-yl]-2-propynyl]piperazine (127 mg) prepared by a similar manner to that of Example 5-(1) and trifluoroacetic acid (5 ml) in dichloromethane (5 ml) was stirred at room temperature for 2 hours. The reaction mixture was concentrated under reduced pressure and the residue was partitioned between saturated aqueous sodium bicarbonate solution. The organic layer was separated, dried over magnesium sulfate and concentrated under reduced pressure. The syrup obtained was dissolved into ethyl acetate and treated with 4N hydrogen chloride in ethyl acetate to give (2R)-1-[3,5-bis(trifluoromethyl)benzoyl]-2-[(1H-indol-3-yl) methyl]-4-[3-(6-aminopyridin-3-yl)-2-propynyl] piperazine dihydrochloride (80 mg).

mp: 190–195° C. $[\alpha]_D^{24.0}$: –13.47° (C=0.23, MeOH) IR (KBr): 3600–3000, 2700–2500, 1668, 1619, 1428, 1359, 1280 cm$^{-1}$ NMR (DMSO-d$_6$, δ): 3.00–5.20 (11H, m), 6.60–7.50 (6H, m), 7.70–8.30 (5H, m), 8.20–8.50 (2H, m), 11.95–11.10 (1H, br s) MASS: 586 (M+H)$^+$ (free) Elemental Analysis Calcd. for C$_{30}$H$_{25}$F$_6$N$_5$O.2HCl.2.5H$_2$O: C, 51.22; H, 4.58; N, 9.95. Found: C, 51.17; H, 4.40; N, 9.27.

EXAMPLE 55

The following compound was obtained according to a similar manner to that of Example 54.

(2R)-1-[3,5-Bis(trifluoromethyl)benzoyl]-2-(3,4-dimethylbenzyl)-4-[3-(6-aminopyridin-3-yl)-2-propynyl]piperazine dihydrochloride mp: 183–189° C. IR (KBr): 3600–2500, 1644, 1596, 1525, 1375, 1280 cm$^{-1}$ NMR (DMSO-d$_6$, δ): 2.00–2.25 (6H, m), 2.80–5.25 (13H, m), 6.60–8.40 (9H, m), 8.00–8.80 (2H, m) MASS: 575 (M+H)$^+$ (free) Elemental Analysis Calcd. for C$_{30}$H$_{28}$F$_6$N$_4$O.2HCl.1.5H$_2$O: C, 53.42; H, 4.93; N, 8.31. Found: C, 53.08; H, 5.01; N, 8.12.

EXAMPLE 56

The following compounds were obtained according to a similar manner to that of Example 5.

(1) (2R)-1-[3,5-Bis(trifluoromethyl)benzoyl]-2-(2-naphthylmethyl)-4-[3-(2-pyridyl)-2-propynyl]piperazine IR (KBr): 3700–3200, 1641, 1278, 1136 cm$^{-1}$ NMR (DMSO-d$_6$, δ): 2.20–4.00 (9H, m), 4.30–5.20 (2H, m), 7.00–8.65 (14H, m) MASS: 582 (M+H)$^+$, 467

(2) (2R)-1-[3,5-Bis(trifluoromethyl)benzoyl]-2-[(1H-indol-3-yl) methyl]-4-[(2E)-3-(3-pyridyl)-2-propenyl]piperazine dihydrochloride mp: 195–203° C. $[\alpha]_D^{24.9}$: –11.20° (C=0.50, MeOH) IR (KBr): 3600–3300, 2700–2500, 1644, 1430, 1363, 1280, 1184 cm$^{-1}$ NMR (DMSO-d$_6$, δ): 3.00–5.20 (11H, m), 6.60–7.60 (6H, m), 7.70–9.00 (8H, m), 11.00 (1H, br s), 12.00–12.40 (2H, m) MASS: 573 (M+H)$^+$ (free) Elemental Analysis Calcd. for C$_{30}$H$_{26}$F$_6$N$_4$O.2HCl.2.5H$_2$O: C, 52.18; H, 4.82; N, 8.11. Found: C, 51.94; H, 4.77; N, 7.77.

(3) (2R)-1-[3,5-Bis(trifluoromethyl)benzoyl]-2-(3,4-dimethylbenzyl)-4-[(2Z)-3-(3-pyridyl)-2-propenyl]piperazine dihydrochloride mp: 170–174° C. $[\alpha]_D^{23.0}$: –7.30° (C=0.50, MeOH) IR (KBr): 3600–3300, 2700–2500, 1644, 1550, 1430, 1363, 1280 cm$^{-1}$ NMR (DMSO-d$_6$, δ): 2.00–2.30 (6H, m), 2.80–5.20 (11H, m), 6.40–8.40 (10H, m), 8.70–8.85 (2H, m), 12.00–12.20 (2H, m) MASS: 562 (M+H)$^+$ (free) Elemental Analysis Calcd. for C$_{30}$H$_{29}$F$_6$N$_3$O.2HCl.2.5H$_2$O: C, 53.03; H, 5.34; N, 6.18. Found: C, 52.99; H, 5.41; N, 5.91.

(4) (2R)-1-[3,5-Bis(trifluoromethyl)benzoyl]-2-[(1H-indol-3-yl) methyl]-4-[4-(2-pyridyl)-3-butynyl]piperazine NMR (CDCl$_3$, δ): 1.80–5.20 (13H, m), 6.80–8.00 (12H, m), 8.19 (1H, s), 8.55 (1H, d, J=4.0 Hz) MASS: 585 (M+H)$^+$

EXAMPLE 57

The following compounds were obtained according to a similar manner to that of Example 5.

(1) (2R)-1-[3,5-Bis(trifluoromethyl)benzoyl]-2-(3,4-dimethylbenzyl)-4-[3-(6-methoxypyridin-3-yl)propyl]piperazine dihydrochloride mp: 127–137° C. $[\alpha]_D^{22.5}$: –15.93° (C=0.16, MeOH) IR (KBr): 3600–3300, 2700–2500, 1646, 1556, 1434, 1280, 1184 cm$^{-1}$ NMR (DMSO-d$_6$, δ): 1.90–5.20 (21H, m), 3.84 (3H, s), 6.60–7.30 (4H, m), 7.40–7.80 (3H, m), 8.00–8.30 (2H, m) MASS: 594 (M+H)$^+$ (free) Elemental Analysis Calcd. for C$_{31}$H$_{33}$F$_6$N$_3$O$_2$.2HCl.1.2H$_2$O: C, 54.11; H, 5.48; N, 6.11. Found: C, 54.09; H, 5.75; N, 5.83.

(2) (2R)-1-[3,5-Bis(trifluoromethyl)benzoyl]-2-[(1H-indol-3-yl) methyl]-4-[3-(6-methoxypyridin-3-yl)propyl]piperazine dihydrochloride mp: 195–200° C. $[\alpha]_D^{22.6}$: –2.03° (C=0.32, MeOH) IR (KBr): 3600–3300, 2700–2300, 1644, 1556, 1494, 1432, 1363, 1280, 1180 cm$^{-1}$ NMR (DMSO-d$_6$, δ): 2.20–5.20 (15H, m), 3.79 (3H, s), 6.60–8.30 (1H, m), 10.95 (1H, br s), 11.60–11.80 (2H, m) MASS: 605 (M+H)$^+$ (free) Elemental Analysis Calcd. for C$_{31}$H$_{30}$F$_6$N$_4$O$_2$.2HCl.1.5H$_2$O: C, 52.58; H, 5.01; N 7.95. Found: C, 52.89; H, 5.40; N, 7.63.

(3) (2R)-1-[3,5-Bis(trifluoromethyl)benzoyl]-2-(2-naphthylmethyl)-4-[3 (2-pyridyl)propyl]piperazine dihydrochloride $[\alpha]_D^{26.8}$: –27.60° (C=0.50, MeOH) IR (KBr): 3700–3000, 2700–2200, 1647, 1279, 1136 cm$^{-1}$ NMR (DMSO-d$_6$, δ): 2.20–4.30 (13H, m), 4.40–5.40 (2H, m), 7.00–8.90 (14H, m) MASS: 586 (M+H)$^+$ (free) Elemental Analysis Calcd. for C$_{32}$H$_{29}$F$_6$N$_3$O.2HCl.2.5H$_2$O: C, 54.63; H, 5.16; N, 5.97. Found: C, 54.55; H, 5.37; N, 5.56.

(4) (2R)-1-[3,5-Bis(trifluoromethyl)benzoyl]-2-[(1H-indol-3-yl) methyl]-4-[4-(2-pyridyl)butyl]piperazine dihydrochloride mp: 155–160° C. $[\alpha]_D^{27.0}$: +9.50° (C=0.10, MeOH) IR (KBr): 3700–3000, 2700–2200, 1641, 1459, 1428, 1280, 1137 cm$^{-1}$ NMR (DMSO-d$_6$, δ): 1.70–2.20 (4H, m), 2.60–5.20 (13H, m), 6.60–8.80 (12H, m), 11.00 (1H, br s), 11.40–11.80 (2H, m) MASS: 589 (M+H)$^+$ (free) Elemental Analysis Calcd. for C$_{31}$H$_{30}$F$_6$N$_4$O.2HCl.2.0H$_2$O: C, 53.38; H, 5.20; N, 8.03. Found: C, 53.34; H, 5.38; N, 7.78.

EXAMPLE 58

A mixture of (2R)-1-[3,5-bis(trifluoromethyl)benzoyl]-2-[(1H-indol-3-yl)methyl]piperazine (0.83 g), methyl α-bromophenylacetate (0.42 g), potassium carbonate (1.0 g) in N,N-dimethylformamide (5 ml) was stirred at 50° C. for 3 hours. The reaction mixture was poured into water and the resulting precipitates were collected by filtration. The precipitates were purified by column chromatography on silica gel using a mixture of dichloromethane and ethyl acetate as eluent to give a mixture of diastereoisomers, methyl (2R, 2S)-2-[(2R)-1-[3,5-bis(trifluoromethyl)benzoyl]-2-[(1H-indol-3-yl) methyl]piperazin-4-yl]-2-phenylacetate (1.00 g).

NMR (CDCl$_3$, δ): 2.00–5.20 (4H, m), 3.69 (3H, s), 6.70–8.20 (14H, m) MASS: 604 (M+H)$^+$ (free)

EXAMPLE 59

A solution of the mixture of diastereoisomers, methyl (2R,2S)-2-[(2R)-1-[3,5-bis(trifluoromethyl)benzoyl]-2-[(1H-indol-3-yl)methyl]piperazin-4-yl]-2-phenylacetate (360 mg) and 1N sodium hydroxide (1.5 ml) in methanol (5 ml) was stirred at 50° C. for 2 hours. The mixture was concentrated under reduced pressure until aqueous solution. The solution was diluted with water and the solution was made acidic (about pH 5) with diluted hydrochloric acid and extracted with ethyl acetate. The organic layer was dried over magnesium sulfate and concentrated under reduced pressure to give a mixture of diastereoisomers, (2R,2S)-2-[(2R)-1-[3,5-bis(trifluoromethyl)benzoyl]-2-[(1H-indol-3-yl)methyl]piperazin-4-yl]-2-phenylacetic acid (0.33 g).

NMR (CDCl$_3$, δ): 2.20–5.80 (10H, m), 6.60–8.20 (14H, m) MASS: 590 (M+H)$^+$ (free)

EXAMPLE 60

Isobutyl chloroformate (0.116 ml) was added dropwise to a suspension of the mixture of diastereoisomers, (2R,2S)-

2-[(2R)-1-[3,5-bis(trifluoromethyl)benzoyl]-2-[(1H-indol-3-yl) methyl]piperazin-4-yl]-2-phenylacetic acid (0.5 g) and N-methylmorpholine (0.103 ml) in 1,2-dimethoxyethane (3 ml) under −18° C. After being stirred at the same temperature for 30 minutes, a solution of sodium borohydride (32 mg) in water (0.5 ml) was added to the mixture all at once. After being stirred at room temperature for 30 minutes, 1N sodium hydroxide solution was added to the mixture and the whole was stirred at room temperature for 1 hour. The mixture was neutralized with diluted hydrochloric acid, and extracted with ethyl acetate. The extract was dried over magnesium sulfate and concentrated under reduced pressure. The residue was purified by column chromatography on silica gel using a mixed eluent of dichloromethane and methanol. The fractions containing the objective compound were collected and evaporated under reduced pressure to give a mixture of diastereoisomers, (2R)-1-[3,5-bis(trifluoromethyl)benzoyl]-2-[(1H-indol-3-yl)methyl]-4-[(1R, 1S)-1-phenyl-2-hydroxyethyl]piperazine (0.42 g).

NMR (CDCl$_3$, δ): 1.90–5.20 (13H, m), 6.60–8.20 (14H, m) MASS: 576 (M+H)$^+$

EXAMPLE 61

Methanesulfonyl chloride (0.058 ml) was added to a solution of the mixture of diastereoisomers, (2R)-1-[3,5-bis(trifluoromethyl)benzoyl]-2-[(1H-indol-3-yl)methyl]-4-[(1R, 1S)-1-phenyl-2-hydroxyethyl]piperazine (0.36 g) and triethylamine (0.16 ml) in dichloromethane (10 ml) under −18° C. After being stirred at the same temperature for 30 minutes, additional methanesulfonyl chloride (0.058 ml) and triethylamine (0.16 ml) were added to the mixture. After being stirred at the same temperature for further 30 minutes, the reaction mixture was washed with water, dried over magnesium sulfate and evaporated under reduced pressure to give the corresponding mesylate. A mixture of the mesylate and morpholine (0.4 ml) in 1,4-dioxane was stirred at 50° for 3 hours. The reaction mixture was concentrated under reduced pressure to give a syrup, which was partitioned between water and ethyl acetate. The organic layer was separated, washed with brine, dried over magnesium sulfate and concentrated under reduced pressure to give the crude mixture of diastereoisomers, which was purified by column chromatography on silica gel using a mixed eluent of dichloromethane and methanol. The faster eluting fractions were collected, evaporated under reduced pressure and treated with 4N hydrogen chloride in ethyl acetate to give a diastereoisomer of (2R)-1-[3,5-bis((trifluoromethyl)benzoyl]-2-[(1H-indol-3-yl) methyl]-4-[(1R or 1S)-1-phenyl-2-morpholinoethyl]piperazine dihydrochloride.

mp: 203–207° C. [α]$_D^{21.7}$: −6.0° (C=0.25, MeOH) IR (KBr): 3700–3300, 3100–2200, 1641, 1450, 1432, 1363, 1280 cm$^{-1}$ NMR (DMSO-d$_6$, δ): 2.40–5.20 (20H, m), 6.60–8.30 (8H, m), 10.95 (1H, s) MASS: 644 (M+H)$^+$ (free) Elemental Analysis Calcd. for C$_{34}$H$_{34}$F$_6$N$_4$O$_2$.2HCl.2/3H$_2$O: C, 55.97; H, 5.16; N, 7.68. Found: C, 55.98; H, 5.48; N, 7.26.

The slower eluting fractions were collected, evaporated under reduced pressure and treated with 4N hydrogen chloride in ethyl acetate to give a diastereoisomer of (2R)-1-[3,5-bis(trifluoromethyl)benzoyl]-2-[(1H-indol-3-yl)methyl]-4-[(1S or 1R)-1-phenyl-2-morpholinoethyl]piperazine dihydrochloride.

mp: 207–212° C. [α]$_D^{21.7}$: −3.33° (C=0.24, MeOH) IR (KBr): 3700–3200, 3000–2300, 1643, 1450, 1432, 1280, 1182 cm$^{-1}$ NMR (DMSO-d$_6$, δ): 2.40–5.20 (20H, m), 6.55–8.35 (8H, m), 10.95 (1H, s), 11.00–12.10 (2H, m) MASS: 644 (M+H)$^+$ (free) Elemental Analysis Calcd. for C$_{34}$H$_{34}$F$_6$N$_4$O$_2$.2HCl.0.5H$_2$O: C, 56.20; H, 5.13; N, 7.71. Found: C, 56.15; H, 5.52; N, 7.32.

EXAMPLE 62

The following compound was obtained according to a similar manner to that of Example 45.

(2R)-1-[3,5-Bis(trifluoromethyl)benzoyl]-2-(3,4-dimethylbenzyl)-4-[3-[(2R,2S)-2-morpholinyl]-2-propenyl] piperazine dihydrochloride mp: 160–163° C. [α]$_D^{25}$: −12.50° (C=0.50, MeOH) IR (KBr): 1645 cm$^{-1}$ NMR (DMSO-d$_6$, δ): 2.08–2.18 (6H, m), 2.55–5.10 (18H, m), 5.80–6.20 (2H, m), 6.60–6.70 (1H, m), 6.90–7.20 (2H, m), 7.47–7.70 (2H, m), 8.15–8.20 (1H, m) MASS: 570 (M+H)$^+$ (free) Elemental Analysis Calcd. for C$_{29}$H$_{35}$F$_6$N$_3$O$_2$.2HCl.1.0H$_2$O: C, 52.59; H, 5.65; N, 6.34. Found: C, 52.85; H, 5.97; N, 6.16.

EXAMPLE 63

A mixture of (2R)-1-[3,5-bis(trifluoromethyl)benzoyl]-2-(3,4-dimethylbenzyl)piperazine (500 mg) and 1,8-diazabicyclo [5.4.0]undec-7-ene (1.5 µl) in tetrahydrofuran (2.5 ml) was cooled to −30° C. with stirring under nitrogen atmosphere. Acrolein (90%, 0.225 ml) was added to the mixture while maintaining the temperature at −20~−40° C. for a period of 10 minutes and then the resulting mixture was stirred at 0° C. After 6 hours, the reaction mixture was diluted with water and extracted with ethyl acetate. The extract was washed with brine and dried over magnesium sulfate. After evaporation of the solvent under reduced pressure, the resulting residue was chromatographed on a silica gel using a mixture of hexane and ethyl acetate as eluent to give (2R)-1-[3,5-bis(trifluoromethyl)benzoyl]-2-(3,4-dimethylbenzyl)-4-(2-formylethyl)piperazine (332 mg) as an oil.

NMR (DMSO-d$_6$, δ): 1.60–4.90 (19H, m), 6.55–6.75 (1H, m), 6.90–7.15 (2H, m), 7.30–7.75 (2H, m), 8.13 (1H, br s), 9.70 (1H, s) MASS: 501 (M+H)$^+$

EXAMPLE 64

To a stirred mixture of 4-amino-3,3-dimethylmorpholine dihydrochloride (122 mg) in dichloromethane (5 ml) was added triethylamine (61 mg) at ice bath temperature. A solution of (2R)-1-[3,5-bis(trifluoromethyl)benzoyl]-2-(3,4-dimethyl benzyl)-4-(2-formylethyl)piperazine (150 mg) in dichloromethane (2 ml) was added and the resulting mixture was stirred at room temperature. After 30 minutes, the reaction mixture was concentrated under reduced pressure. The resulting residue was chromatographed on a silica gel using a mixture of hexane and ethyl acetate as eluent and the desired product was treated with 4N hydrogen chloride in ethyl acetate to give (2R)-1-[3,5-bis(trifluoromethyl) benzoyl]-2-(3,4-dimethylbenzyl)-4-[3-(3,3-dimethylmorpholino-imino)propyl]piperazine dihydrochloride (122 mg).

IR (KBr): 3425, 2700, 2625, 1645, 1430, 1280, 1180, 1135 cm$^{-1}$ NMR (DMSO-d$_6$, δ): 1.06–1.40 (6H, m), 2.00–2.40 (6H, m), 2.60–5.80 (19H, m), 6.64–8.30 (6H, mn), 10.00–12.18 (2H, m) MASS: 613 (M+H)$^+$ (free) Elemental Analysis Calcd. for C$_{31}$H$_{38}$F$_6$N$_4$O$_2$.2HCl.2H$_2$O: C, 51.60; H, 6.15; N, 7.76. Found: C, 51.82; H, 6.49; N, 7.29.

EXAMPLE 65

To a stirred mixture of 4-aminohomomorpholine dihydrochloride (100 mg) in dichloromethane (5 ml) was added triethylamine (107 mg) at ice bath temperature. A solution of (2R)-1-[3,5-bis(trifluoromethyl)benzoyl]-2-(3,4-dimethylbenzyl)-4-(2-formylethyl)piperazine (200 mg) in dichloromethane (2 ml) was added and the resulting mixture was stirred at room temperature. After 30 minutes, the reaction mixture was concentrated under reduced pressure. The resulting residue was chromatographed on a silica gel using a mixture of hexane and ethyl acetate as eluent to give (2R)-1-[3,5-bis(trifluoromethyl)benzoyl]-2-(3,4-dimethylbenzyl)-4-[3-(homomorpholinoimino)propyl] piperazine (110 mg) and an intermediate. This compound was dissolved in methanol (5 ml) and sodium borohydride (17 mg) was added at ice bath temperature. After 2 hours, additional sodium borohydride (40 mg) was added and the reaction mixture was stirred at room temperature overnight. The reaction mixture was diluted with water and then extracted with dichloromethane. The extract was washed with brine and dried over magnesium sulfate. After evaporation of the solvent, the resulting residue was purified by a silica gel column chromatography using a mixture of dichloromethane and methanol (50:) as eluent to give the desired product, which was dissolved in ethyl acetate and treated with 4N hydrogen chloride in ethyl acetate to afford (2R)-1-[3,5-bis-(trifluoromethyl) benzoyl]-2-(3,4-dimethylbenzyl)-4-[3-(homomorpholinoamino) propyl] piperazine dihydrochloride (66 mg)

$[\alpha]_D^{27}$: −13.7° (C=0.50, MeOH) IR (KBr): 3450, 2700, 2620, 1645, 1430, 1280, 1185, 1135 cm$^{-1}$ MASS: 601 (M+H)$^+$ (free) Elemental Analysis Calcd. for $C_{30}H_{38}F_6N_4O_2$.2HCl.0.7H$_2$O: C, 52.51; H, 6.08; N, 8.17. Found: C, 52.51; H, 6.05; N, 7.86.

Preparation 32

Di-tert-butyl dicarbonate (29.4 g) was added to a mixture of (2R)-2-(3,4-dimethylbenzyl)-4-benzylpiperazine dihydrochloride (45.0 g) and triethylamine (59.6 ml) in tetrahydrofuran (900 ml) under ice-cooling. After 3 hours of stirring at the same temperature, stirring was continued at room temperature for 9 hours. The mixture was poured into ice-water (1 l) and extracted with ethyl acetate (2.5 l). The extract was washed successively with 1N hydrochloric acid and brine, dried over sodium sulfate and evaporated under reduced pressure to give a crude oil of (2R)-4-benzyl-1-tert-butoxycarbonyl-1-(3,4-dimethylbenzyl)piperazine (49.6 g).

NMR (CDCl$_3$, δ): 1.40 (9H, s), 1.90–2.06 (2H, m), 2.15–2.17 (6H, m), 2.60–4.4 (9H, m), 6.86–7.05 (3H, m), 7.20–7.39 (5H, m) MASS (APCI): 395 (M+H)$^+$, 339, 295

Preparation 33

A solution of (2R)-4-benzyl-1-tert-butoxycarbonyl-2-(3,4-dimethylbenzyl)piperazine (48.5 g) in methanol (730 ml) was hydrogenated over 20% palladium hydroxide-carbon (0.3 g) at room temperture under atmospheric pressure. After removal of the catalyst by filtration, the filtrate was evaporated under reduced pressure. The residue was purified by column chromatography on silica gel using a mixed solvent of dichloromethane and methanol (10:1). The fractions containing the objective compound was collected and evaporated under reduced pressure to give an oil of (2R)-1-tert -butoxycarbonyl-2-(3,4-dimethylbenzyl)piperazine (33.7 g).

NMR (DMSO-d$_6$, δ): 1.26 (9H, s), 2.15–2.17 (6H, m), 2.30–4.05 (10H, m), 6.86–7.05 (3H, m) MASS (APCI): 305 (M+H)$^+$, 249, 205

Preparation 34

A mixture of (2R)-1-tert-butoxycarbonyl-2-(3,4-dimethylbenzyl) piperazine (29.0 g), 3,3-dimethyl-4-(4-chloro-2-butynyl)morpholinine hydrochloride (22.7 g), potassium carbonate (39.5 g) and potassium iodide (1.58 g) in N,N-dimethylformamide (145 ml) was stirred at room temperature for 2 hours, followed by 53° C. for 3 hours. After being cooled to room temperature, the mixture was poured into ice-water (1.2 l) and extracted with ethyl acetate (1.2 l). The extract was washed with water (1 l), and re-extracted with 1N hydrochlioric acid (190 ml). The acidic aqueous layer was separated and the pH of the solution was made to 10 with 1N sodium hydroxide. The alkaline solution was extracted with ethyl acetate (1.1 l) and the extract was washed with brine, dried over sodium sulfate, and evaporated under reduced pressure to give an oil of (2R)-1-tert-butoxycarbonyl-2-(3,4-dimethylbenzyl)-4-[4-(3,3-dimethylmorpholino)-2-butynyl]-piperazine (43.1 g).

NMR (DMSO-d$_6$, δ): 0.95 (6H, s), 1.26 (9H, s), 2.03–4.20 (25H, m), 6.80–7.05 (3H, m) MASS (APCI): 470 (M+H)$^+$

Preparation 35

A solution of 4N hydrogen chloride in ethyl acetate was added to a solution of (2R)-1-tert-butoxycarbonyl-2-(3,4-dimethylbenzyl)-4-[4-(3,3-dimethylmorpholino)-2-butynyl] piperazine (40.0 g) in ethanol (120 ml) at room temperature and the whole was stirred for 12 hours. The reaction mixture was concentrated under reduced pressure and the residue was partitioned between ethyl acetate (500 ml) and potassium carbonate solution. The organic layer was separated and the aqueous layer was extracted with ethyl acetate (300 ml). The combined extract was dried over sodium sulfate and evaporated under reduced pressure, and the residue was purified by column chromatography on silica gel using a mixed solvent of n-hexane and ethyl acetate (3:1). The fractions containing the objective compound were collected and evaporated under reduced pressure, and treated with 4N hydrogen chloride in ethyl acetate to give (3R)-3-(3,4-dimethylbenzyl)-1-[4-(3,3-dimethylmorpholino)-2-butynyl] piperazine trihydrochloride (37.7 g).

mp: 264–272° C. $[\alpha]_D^{27}$: −23.6° (C=0.5, MeOH) IR (KBr): 3500–3400, 2900, 2570, 2480, 1637, 1626, 1508, 1455, 1180 cm$^{-1}$ NMR (DMSO-d$_6$, δ): 1.33 (3H, s), 1.39 (3H, s), 2.21 (6H, s), 2.80–4.60 (20H, m), 6.90–7.20 (3H, m), 9.90–10.40 (3H, m) MASS (APCI): 370 (M+H)$^+$ (free)

Preparation 36

1-(3-Dimethylaminopropyl)-3-ethylcarbodiimide (0.22 ml) was added over 5 minutes to a mixture of (3R)-3-(3,4-dimethylbenzyl)-1-[4-(3,3-dimethylmorpholino)-2-butynyl]-piperazine trihydrochloride (0.48 g) and 3,5-bis (trifluoromethyl)benzoic acid (0.27 g), 1-hydroxybenzotriazole (0.15 g) and triethylamine (0.35 ml) in dichloromethane (10 ml). After 2 hours of stirring at room temperature, the reaction mixture was directly purified by column chromatography on silica gel using a mixed solvent of dichloromethane and methanol (40:1). The fractions containing the objective compound was collected and evaporated under reduced pressure. The residue was treated with 4N hydrogen chloride in ethyl acetate and recrystallized from a mixture of acetone and water to give colorless crystals of (2R)-1-[3,5-bis(trifluoromethyl)benzoyl]-2-(3,4-dimethylbenzyl)-4-[4-(3,3-dimethylmorpholino)-2-butynyl]-piperazine dihydrochloride (525 g).

mp: 180–190° C. $[\alpha]_D^{28.3}$: −7.24° (C=1.05, MeOH) IR (Nujol): 3300, 2700–2400, 1635 cm$^{-1}$ NMR (DMSO-d$_6$, δ): 1.30–1.40 (6H, m), 2.00–5.22 (25H, m), 6.60–8.20 (6H, m), 12.05–12.20 (2H, m) MASS (APCI): 610 (M+1H) (free)

Elemental Analysis Calcd. for $C_{32}H_{37}F_6N_3O_2$.2HCl.2.5H$_2$O: C, 52.82; H, 6.09; N, 5.68. Found: C, 52.84; H, 5.89; N, 5.78.

Preparation 37

3,3-Dimethylmorpholine hydrochloride (5.3 g) was added by small portions over 1 hour to a mixture of 1,4-dichloro- 2-butyne (6.9 ml) and potassium carbonate (9.8 g) in N,N-dimethylformamide (100 ml). After 20 hours of stirring, the mixture was poured into ice-water (200 ml) and extracted with isopropyl ether (100 ml) two times. The extract was washed with brine (100 ml), dried over magnesium sulfate, and evaporated under reduced pressure. The residue was purified by column chromatography on silica gel using a mixed solvent of n-hexane and ethyl acetate (4:1). The fractions containing the objective compound was collected and evaporated under reduced pressure, and treated with 4N hydrogen chloride in ethyl acetate to give brownish powders of 3,3-dimethyl-4-(4-chloro-2-butynyl)morphlinine hydrochloride (5.32 g).

NMR (DMSO-$d_6$, δ): 1.35–1.39 (6H, m), 3.20–4.40 (8H, m), 4.56 (2H, s), 11.50–11.90 (1H, m) MASS (APCI): 202 $(M+H)^+$ (free), 204

Preparation 38

A mixture of (2R)-1-[3,5-bis(trifluoromethyl)benzoyl]-2-(3,4-dimethylbenzyl)piperazine (3.0 g), propargyl bromide (0.84 g) and potassium carbonate (1.17 g) in N,N-dimethylformamide (300 ml) was stirred at room temperature for 1.5 hours. The mixture was poured into ice-water and extracted with ethyl acetate. The extract was washed with brine, dried over magnesium sulfate and evaporated under reduced pressure to give a syrup of (2R)-1-[3,5-bis(trifluoromethyl)benzoyl]-2-(3,4-dimethylbenzyl)-4-(2-propynyl)piperazine (3.80 g).

NMR (DMSO-$d_6$, δ): 2.00–5.00 (18H, m), 6.66–8.20 (6H, m) MASS (APCI): 483 $(M+H)^+$

Preparation 39

A mixture of (2R)-1-[3,5-bis(trifluoromethyl)benzoyl]-2-(3,4-dimethylbenzyl)-4-(2-propynyl)piperazine (0.49 g), 3,3-dimethylmorpholine hydrochloride (0.185 g), paraformaldehyde (62 mg), diisopropylethylamine (0.21 ml), and copper (1) iodide (20 mg) in 1,4-dioxane (5 ml) was stirred at 70° C. for 1.5 hours. After removal of the solvent by evaporation, the residue was purified by column chromatography on silica gel using a mixed solvent of dichloromethane and methanol (40:1). The fractions containing the objective compound was collected and evaporated under reduced pressure to give a syrup of (2R)-1-[3,5-bis(trifluoromethyl)benzoyl]-2-(3,4-dimethylbenzyl)-4-[4-(3,3-dimethylmorpholino)-2-butynyl]piperazine (0.45 g).

NMR (CDCl$_3$, δ): 0.97 (6H, s), 2.03–5.00 (25H, m), 6.66–8.23 (6H, m) MASS (APCI): 610 $(M+H)^+$, 513 its hydrochloride mp: 185–188° C. $[\alpha]_D^{28}$: −8.6° (C=0.18, MeOH) IR (KBr): 2928, 2585, 2515, 1633, 1433, 1279, 1180, 1132 cm$^{-1}$ NMR (DMSO-$d_6$, δ): 1.33–1.40 (6H, m), 2.09–2.18 (6H, m), 2.50–5.20 (19H, m), 6.66–8.15 (6H, m) MASS (APCI): 610 $(M+H)^+$ (free)

Preparation 40

A mixture of 37% aqueous formaldehyde (0.21 g), (2R)-1-[3,5-bis(trifluoromethyl)benzoyl]-2-(3,4-dimethylbenzyl)piperazine (0.75.g), propargyl alcohol (0.11 ml), copper(II) sulfate pentahydrate (1.3 mg) and potassium iodide (2.8 mg) in 1,4-dioxane was stirred at 100° C. for 2 hours. After being cooled to room temperature, the mixture was made basic with aqueous saturated sodium hydrogen carbonate solution. The resulting mixture was filtered and the filtrate was extracted with ethyl acetate. The extract was washed with brine, dried over magnesium sulfate and evaporated under reduced pressure. The residue was purified by column chromatography on silica gel using a mixed solvent of n-hexane and ethyl acetate (4:1). The fractions containing the objective compound was collected and evaporated under reduced pressure to give (2R)-1-[3,5-bis(trifluoromethyl) benzoyl]-2-(3,4-dimethylbenzyl)-4-(4-hydroxy-2-butynyl)piperazine (0.78 g) as a syrup.

NMR (CDCl$_3$, δ): 1.99–5.00 (19H, m), 5.15 (1H, t, J=5.9 Hz), 6.66–8.23 (6H, m) MASS (APCI): 513 $(M+H)^+$, 499, 483

Preparation 41

The following compound was obtained according to a similar manner to that of Example 39.

(2R)-1-[3,5-Bis(trifluoromethyl)benzoyl]-2-(3,4-dimethylbenzyl)-4-[4-(3,3-dimethylmorpholino)-2-butynyl]piperazine NMR (CDCl$_3$, δ): 0.97 (6H, s), 2.03–5.00 (25H, m), 6.66–8.23 (6H, m) MASS (APCI): 610 $(M+H)^+$, 513

Preparation 42

A mixture of 3,3-dimethylmorpholine hydrochloride (30.0 g), propargyl bromide (16.4 ml) and potassium carbonate (63 g) in N,N-dimethylformamide (300 ml) was stirred at 45–48° C. for 1.5 hours. After being cooled to room temperature, the mixture was poured into ice-water (800 ml) and extracted with ethyl acetate (500 ml) two times. The extract was washed with brine (400 ml), dried over magnesium sulfate and filtered. The filtrate was treated with 4N hydrogen chloride in ethyl acetate (98 ml) under ice-cooling. The solution was concentrated under reduced pressure to give a crude solid, which was collected by filtration and washed with isopropyl ether to give brownish crystals of 3,3.-dimethyl-4-(2-propynyl)morpholine hydrochloride (35 g).

IR (KBr): 3500–3400, 2900, 2570, 2480, 1637, 1626, 1508, 1455, 1180 cm$^{-1}$ NMR (DMSO-$d_6$, δ): 1.20–1.50 (6H, m), 3.20–4.20 (9H, m), 11.91 (1H, s) MASS (APCI): 154 $(M+H)^+$ (free)

Preparation 43

A mixture of 3,3-dimethyl-4-(2-propynyl)morpholine hydrochloride (0.24 g), 37% aqueous formaldehyde (0.16 ml), (2R)-1-[3,5-bis(trifluoromethyl)benzoyl]-2-(3,4-dimethylbenzyl)piperazine (0.57 g), copper(II) sulfate pentahydrate (5 mg) and potassium iodide (20 mg) in 1,4-dioxane (0.7 ml) was stirred at 90° C. for 1 hour. After being cooled to room temperature, the mixture was poured into ice-water and the aqueous mixture was made alkaline with saturated aqueous sodium hydrogen carbonate solution. The resulting mixture was extracted with ethyl acetate. The extract was washed with brine, dried over magnesium sulfate and evaporated under reduced pressure. The residue was purified by column chromatography on silica gel using a mixed solvent of dichloromethane and methanol (40:1). The fractions containing the objective compound was collected and evaporated under reduced pressure and treated with 4N hydrogen chloride in ethyl acetate solution. The resulting mixture was evaporated under reduced pressure and the residue was recrystallized from a mixture of acetone and water to give colorless crystals of (2R)-1-[3,5-bis(trifluoromethyl) benzoyl]-2-(3,4-dimethylbenzyl)-4-[4-(3,3-dimethyl-morpholino)-2-butynyl]piperazine dihydrochloride (0.64 g).

mp: 180–190° C. $[\alpha]_D^{28.3}$: −7.24° (C=1.05, MeOH) IR (Nujol): 3300, 2700–2400, 1635 cm$^{-1}$ NMR (DMSO-$d_6$, δ): 1.30–1.40 (6H, m), 2.00–5.22 (25H, m), 6.60–8.20 (6H, m), 12.05–12.20 (2H, m) MASS (APCI): 610 (M+1H) (free)

Elemental Analysis Calcd. for $C_{32}H_{37}F_6N_3O_2 \cdot 2HCl \cdot 2.5H_2O$: C, 52.82; H, 6.09; N, 5.68. Found: C, 52.84; H, 5.89; N, 5.78.

Preparation 44

The following compounds were obtained according to a similar manner to that of Preparation 1.

(1) 3-[2-(4-Methoxy)pyridyl]-2-propyn-1-ol

IR (KBr): 3130, 1598, 1562, 1471, 1425 cm$^{-1}$ NMR (DMSO-d$_6$, δ): 3.84 (3H, s), 4.31 (2H, d, J=6.0 Hz), 5.41 (1H, t, J=6.0 Hz), 6.97 (1H, dd, J=2.6, 5.8 Hz), 7.06 (1H, d, J=2.6 Hz), 8.35 (1H, d, J=5.8 Hz) MASS (APCI): 164 (M+H)$^+$134

(2) 3-[2-(4-Methoxycarbonyl)pyridyl]-2-propyn-1-ol

IR (KBr): 3133, 1598, 1568, 1430 cm$^{-1}$ NMR (DMSO-d$_6$, δ): 3.91 (3H, s), 4.35 (2H, d, J=6.0 Hz), 5.75 (1H, d, J=6.0 Hz), 7.70–7.80 (1H, m), 8.68 (1H, d, J=5.0 Hz), 8.78 (1H, d, J=5.0 Hz) MASS (APCI): 192 (M+H)$^+$

Preparation 45

(1) To a stirred solution of chloropyrazine (1.14 g) and [1,2-bis(diphenylphosphino)ethane]nickel(II) chloride (106 mg) in dry tetrahydrofuran (40 ml) was added a solution of 3,4-methylenedioxybenzylmagnesium chloride (0.6 M in tetrahydrofuran, 29 ml) at 5° C. under nitrogen atmosphere over 15 minutes. After 1 hour of stirring at 5° C., 3N hydrochloric acid was added slowly under nitrogen atmosphere and the mixture was stirred for 1 hour. The organic layer was separated and the aqueous layer was extracted with ethyl acetate. The combined extract was washed with water and dried over magnesium sulfate. The usual work up followed by flash chromatography on silica gel with a mixture of n-hexane and ethyl acetate (10:1–4:1) gave 2-(3,4-methylenedioxybenzyl)pyrazine (454 mg) as a colorless oil.

NMR (CDCl$_3$, δ): 4.59 (2H, s), 5.93 (2H, s), 6.75–6.88 (3H, m), 8.44–8.56 (3H, m) MASS (APCI): 215 (M+H)$^+$ (2) To a stirred solution of 2-(3,4-methylenedioxybenzyl)pyrazine (317 mg) in dry tetrahydrofuran (12 ml) was added a solution of diisobutylaluminum hydride (0.95 M in n-hexane, 15.6 ml) at 5° C. under nitrogen atmosphere. After 1 hour of stirring at 5° C., the mixture was added saturated sodium sulfate solution until gas evolution ceased. The insoluble materials were removed by filtration through Celite® and the organic layer was separated, dried over magnesium sulfate, and concentrated under reduced pressure. The residue was dissolved in ethyl acetate and treated with 4N hydrogen chloride in ethyl acetate to give 2-(3,4-methylenedioxy-benzyl)piperazine dihydrochloride (125 mg) as a powder.

NMR (DMSO-d$_6$, δ): 2.79–3.66 (9H, m), 6.02 (2H, s), 6.74–6.94 (3H, m), 9.79 (4H, br s) MASS (APCI): 221 (M+H)$^+$ (free)

Preparation 46

(1) To a stirred solution of 4-bromo-2-methylbenzoic acid (10.75 g) in tetrahydrofuran (50 ml) was added borane-tetrahydrofuran complex (1 M in tetrahydrofuran, 150 ml) by syringe under nitrogen atmosphere at 5° C. and the mixture was heated under reflux for 18 hours. After cooling, water (50 ml) and potassium carbonate (20 g) were added to the solution at 5° C. The organic layer was separated and the aqueous layer was extracted with ethyl acetate. The combined extract was washed with water, dried over magnesium sulfate, and concentrated under reduced pressure to give 4-bromo-2-methylbenzyl alcohol (9.55 g). This compound was used to the next reaction without further purification.

(2) Tert-butylchlorodiphenylsilane (13.06 g) and imidazole (9.7 g) were added to a solution of 4-bromo-2-methylbenzyl alcohol (9.55 g) in N,N-dimethylformamide (80 ml) at 5° C. and the mixture was allowed to warm to room temperature, and stirred for 18 hours. The mixture was extracted with ethyl acetate and the extract was washed with water, dried over magnesium sulfate, and concentrated under reduced pressure to give 1-bromo-4-(tert-butyldiphenylsilyloxymethyl)-3-methylbenzene (20.5 g) as a colorless oil.

NMR (DMSO-d$_6$, δ): 1.03 (9H, s), 2.14 (3H, s), 4.70 (2H, s), 7.34–7.71 (13H, m)

(3) To a stirred solution of 1-bromo-4-(tert-butyldiphenylsilyloxymethyl)-3-methylbenzene (2.19 g) in tetrahydrofuran (30 ml) was added 1.6 M butyllithium in hexane (4.69 ml) by syringe under nitrogen atmosphere at −78° C. After 30 minutes of stirring at −78° C., N,N-dimethylformamide (1.16 ml) was added to the solution at −78° C. and then the mixture was allowed to warm to 5° C. over 1.5 hours. Saturated ammonium chloride solution (10 ml) was added to the mixture and the organic layer was separated, and the aqueous layer was extracted with ethyl acetate. The combined extract was washed with water, dried over magnesium sulfate, and concentrated under reduced pressure to give 4-(tert-butyldiphenylsilyloxymethyl)-3-methylbenzaldehyde (1.90 g) as a colorless oil.

NMR (DMSO-d$_6$, δ): 1.06 9H, s), 2.20 (3H, s), 4.38 (2H, s), 7.37–7.83 (13H, m), 9.97 (1H, s) MASS (APCI): 389 (M+H)$^+$

4) To a stirred mixture of 4-(tert-butyldiphenylsilyloxymethyl)-3-methylbenzaldehyde (1.94 g) and 1,4-diacetyl-2,5-piperazinedione (991 mg) in a mixture of N,N-dimethylformamide (10 ml) and tert-butanol (10 ml) was added potassium tert-butoxide (561 mg) at 5° C. The mixture was stirred for 1 hour at room temperature and then poured into water (300 ml), and stirring was continued for 18 hours at room temperature. The resulting precipitates were collected by filtration and washed with water and isopropyl ether, and dried under reduced pressure to give 1-acetyl-3-(4-tert-butyldiphenylsilyloxymethyl-3-methylphenyl)methylene-2,5-piperazinedione (1.88 g) as a powder.

NMR (DMSO-d$_6$, δ): 1.05 (9H, s), 1.99 (3H, s), 2.19 (3H, s), 4.37 (2H, s), 4.77 (2H, s), 6.93 (1H, s), 7.40–7.69 (13H, m), 10.37 (1H, s) MASS (APCI): 527 (M+H)$^+$ (5) A solution of 1-acetyl-3-(4-tert-butyldiphenylsilyloxymethyl-3-methylphenyl)methylene-2,5-piperazinedione (6.3 g) in methanol (300 ml) was hydrogenated over 10% palladium-carbon (50% wet) for 4 hours at atmospheric pressure. After removal of the catalyst by filtration, to the filtrate was added hydrazine monohydrate (721 mg). The mixture was stirred for 1 hour at room temperature and concentrated under reduced pressure. The residue was triturated with a mixture of isopropyl ether (200 ml) and n-hexane (400 ml) and the precipitates were collected by filtration, and washed with isopropyl ether to give a crude product. This was purified by flash column chromatography on silica gel using ethyl acetate and a mixture of dichloromethane and methanol (15:1) as eluent to give 3-(4-tert-butyldiphenylsilyloxymethyl-3-methylbenzyl)-2,5-piperazinedione (4.67 g) as a powder.

NMR (DMSO-d$_6$, δ): 1.02 (9H, s), 2.12 (3H, s), 2.77–3.18 (3H, m), 3.37 (1H, m), 4.04 (1H, m), 4.72 (2H, s), 6.97–7.04 (2H, m), 7.29–7.66 (11H, m), 7.94 (1H, m), 8.14 (1H, m) MASS (APCI): 487 (M+H)$^+$ (6) To a stirred solution of 3-(4-tert-butyldiphenylsilyloxymethyl-3-methylbenzyl)-2,5-piperazinedione (1.46 g) in a mixture of tetrahydrofuran (40 ml) and 1,2-dimethoxyethane (40 ml) was added lithium aluminum hydride (683 mg) under nitrogen atmosphere at 5° C. and the mixture was heated under reflux for 6 hours. After cooling, the reaction mixture was quenched by sequential addition of water (1.5 ml), 15% sodium hydroxide solution (1.5 ml), and water (4.5 ml). The insoluble materials were removed by filtration through Celite®. The organic layer was dried over magnesium sulfate and concentrated under reduced pressure to leave an oil which was purified by flash column chromatography on silica gel using a mixture of dichloromethane and methanol (50:1–20:1) to give 1,4-bis (benzyloxycarbonyl)-2-(4-hydroxymethyl-3-menthylbenzyl)piperazine (242 mg) as a powder.

NMR (DMSO-$d_6$, δ): 2.09 (3H, m), 2.58–3.22 (5H, m), 3.64–4.50 (6H, m), 4.82–5.21 (5H, m), 6.86–7.72 (13H, m)

(7) A solution of 1,4-bis(benzyloxycarbonyl)-2-(4-hydroxymethyl-3-methylbenzyl)piperazine (6.3 g) in methanol (5 ml) was hydrogenated over 10% palladium-carbon (50% wet, 22 mg) for 6 hours at atmospheric pressure. After removal of the catalyst by filtration, the filtrate was treated with 4N hydrogen chloride in ethyl acetate and concentrated under reduced pressure to give 2-(4-hydroxymethyl-3-methylbenzyl)piperazine dihydrochloride (96 mg) as a powder.

MASS (APCI): 221 (M+H)$^+$ (free)

Preparation 47

(1) The following compound was obtained according to a similar manner to that of Preparation 46-(4).

1-Acetyl-3-[1,4-benzodioxan-6-yl)methylene]-2,5-piperazinedione

NMR (DMSO-$d_6$, δ): 2.48 (3H, s), 4.28 (4H, s), 4.35 (2H, s), 6.86–7.16 (4H, m), 10.30 (1H, s) MASS (APCI): 303 (M+H)$^+$ (2) The following compound was obtained according to a similar manner to that of Preparation 46-(5).

3-[(1,4-Benzodioxan-6-yl)methyl]-2,5-piperazinedione

NMR (DMSO-$d_6$, δ): 2.75 (1H, dd, J=13.6, 4.9 Hz), 2.94 (1H, m), 3.00 (1H, m), 3.43 (1H, dd, J=17.4, 2.7 Hz), 3.97 (1H, m), 4.20 (4H, s), 6.57–6.77 (3H, m), 7.93 (1H, s), 8.10 (1H, m) MASS (APCI): 263 (M+H)$^+$ (3) To a stirred suspension of 3-[(1,4-benzodioxan-6-yl)methyl]-2,5-piperazinedione (564 mg) in tetrahydrofuran (100 ml) was added borane-tetrahydrofuran complex (1 M in tetrahydrofuran, 21 ml) by syringe under nitrogen atmosphere at room temperature and the mixture was heated under reflux for 18 hours. After cooling, the reaction mixture was filtered, and the filtrate was slowly added 12% hydrogen bromide in acetic acid (10 ml). To the mixture was added n-hexane (100 ml) and the whole was stirred for 1 hour at 5° C. The resulting precipitates were collected by filtration and dried under reduced pressure to give 2-[(1,4-benzodioxan-6-yl) methyl]piperazine dihydrobromide (831 mg) as a powder.

NMR (DMSO-$d_6$, δ): 2.62–3.80 (9H, m), 4.23 (4H, s), 6.71–6.88 (3H, m) MASS (APCI) 235 (M+H)$^+$ (free)

Preparation 48

(1) The following compound was obtained according to a similar manner to that of Preparation 46-(4).

1-Acetyl-3-[(4-methoxy-3-methylphenyl)methylene]-2,5-piperazinedione

NMR (DMSO-$d_6$, δ): 2.17 (3H, s), 2.49 (3H, s), 3.83 (3H, s), 4.35 (2H, s), 6.90 (1H, s), 6.94 (1H, d, J=15.7 Hz), 7.32 (2H, m), 10.28 (1H, s) MASS (APCI): 289 (M+H)$^+$ (2) The following compound was obtained according to a similar manner to that of Preparation 46-(5).

3-(4-Methoxy-3-methylbenzyl)-2,5-piperazinedione

NMR (DMSO-$d_6$, δ): 2.09 (3H, s), 2.73–3.04 (3H, m), 3.34 (1H, m), 3.75 (3H, s), 3.99 (1H, m), 6.81–6.97 (3H, m), 7.89 (1H, s), 8.11 (1H, m) MASS (APCI): 249 (M+H)$^+$ (3) The following compound was obtained according to a similar manner to that of Preparation 47-(3).

2-(4-Methoxy-3-methylbenzyl)piperazine dihydrobromide

NMR (DMSO-$d_6$, δ): 2.09 (3H, s), 2.60–3.72 (9H, m), 3.78 (3H, s), 6.55 (2H, m), 6.87–7.14 (3H, m), 9.09 (2H, m)

MASS (APCI): 221 (M+H)$^+$ (free)

Preparation 49

(1) The following compound was obtained according to a similar manner to that of Preparation 46-(4).

1-Acetyl-3-[(2,3-dimethoxyphenyl)methylene]-2,5-piperazinedione

IR (KBr): 1712, 1697, 1685, 1647, 1624, 1373, 1271, 1225 cm$^{-1}$ NMR (DMSO-$d_6$, δ): 2.51 (3H, s), 3.74 (3H, s), 3.83 (3H, s), 4.35 (2H, s), 7.03–7.16 (4H, m), 10.07 (1H, s) MASS (APCI): 305 (M+H)$^+$ (2) A solution of 1-acetyl-3-[(2,3-dimethoxyphenyl) methylene]-2,5-piperazinedione (2.40 g) in a mixed solvent of tetrahydrofuran (120 ml) and methanol (80 ml) was hydrogenated using 10% palladium-carbon (50% wet, 0.55 g) at atmospheric pressure for 3 hours. The catalyst was removed by filtration and the filtrate was concentrated under reduced pressure. The resulting precipitates were collected by filtration to give gray solid of 1-acetyl-3-(2,3-dimethoxyenzl)-2,5-piperazinedione (2.55 g).

IR (KBr): 3265, 1726, 1711, 1689, 1487, 1460, 1358, 1275, 1257 cm$^{-1}$ NMR (DMSO-$d_6$, δ): 2.42 (3H, s), 2.90–3.20 (2H, m), 3.57–3.83 (1H, m), 3.72 (3H, s), 3.79 (3H, s), 4.14–4.23 (2H, m), 6.74–7.04 (3H, m), 8.34 (1H, s) MASS (APCI): 307 (M+H)$^+$ (3) To a suspension of 1-acetyl-3-(2,3-dimethoxybenzyl)-2,5-piperazinedione (2.49 g) in tetrahydrofuran (38 ml) was added hydrazine monohydrate (0.43 ml) at room temperature and the mixture was stirred at the same temperature for 30 minutes. The resulting precipitates were collected by filtration and washed with tetrahydrofuran to give powders of 3-(2,3-dimethoxybenzyl)-2,5-piperazinedione (1.40 g)

IR (KBr): 3195, 3053, 1682, 1658, 1460, 1271, 1078 cm$^{-1}$ NMR (DMSO-$d_6$, δ): 2.87–3.09 (2H, m), 3.42–3.54 (2H, m), 3.73 (3H, s), 3.79 (3H, s), 3.88–3.96 (1H, m), 6.73–7.02 (3H, m), 7.94–8.00 (2H, m) MASS (APCI): 265 (M+H)$^+$ (4) A suspension of 3-(2,3-dimethoxybenzyl)-2,5-piperazinedione (1.26 g) in a mixed solvent of tetrahydrofuran (50 ml) and 1,2-dimethoxyethane (50 ml) was heated at 60° C. with stirring and lithium aluminum hydride (0.905 g) was added thereto portionwise carefully. After the reaction mixture was heated at 70° C. with stirring for 3 hours, lithium aluminum hydride (0.20 g) and tetrahydrofuran (30 ml) were added thereto again and the suspension was stirred at the same temperature for 12 hours. After being cooled with ice-water, the mixture was quenched by sequential addition of water (1.3 ml), 15% aqueous sodium hydroxide (1.3 ml), water (3.8 ml) and the whole was stirred at room temperature for 2 hours. The resulting insoluble materials were removed by filtration and the filtrate was dried over sodium sulfate, and evaporated under reduced pressure to give light yellowish oil of 2-(2,3-dimethoxybenzyl) piperazine (0.97 g).

IR (KBr): 2941, 1481, 1475, 1275, 1080 cm$^{-1}$ NMR (DMSO-$d_6$, δ): 2.07–3.60 (9H, m), 3.69 (3H, s), 3.78 (3H, s), 6.71–7.00 (3H, m) MASS (APCI): 237 (M+H)$^+$ (5) A solution of benzyloxycarbonyl chloride (0.59 g) in dichloromethane (3.0 ml) was added dropwise to a solution of 2-(2,3-dimethoxybenzyl)piperazine (0.91 g) and triethylamine (0.64 ml) in dichloromethane (18 ml) below 5° C. over 5 minutes under ice-cooling, and the reaction mixture was stirred at the same temperature for 15 minutes. After 2 hours of stirring at room temperature, the mixture was poured into a mixed solvent of water (40 ml) and dichloromethane (25 ml) and the whole was adjusted to pH 9 with aqueous sodium hydrogen carbonate solution. The organic layer was separated, washed with brine, dried over sodium sulfate and evaporated under reduced pressure. The residue was purified by column chromatography on silica gel (20 g) using a mixed solvent of dichloromethane and methanol (40:1). The fractions containing the objective compound were collected and evaporated under reduced pressure to give colorless oil of 1-(benzyloxycarbonyl)-3-(2,3-dimethoxybenzyl)piperazine (0.68 g).

IR (KBr): 1714, 1699, 1685, 1273, 1244, 1225 cm$^{-1}$ NMR (CDCl$_3$, δ): 1.71 (1H, s), 2.23–3.00 (9H, m), 3.82 (3H, s), 3.86 (3H, s), 5.13 (2H, s), 6.74–7.03 (3H, m), 7.34 (5H, s) MASS (APCI): 371 (M+H)$^+$

Preparation 50

A solution of 1-[3,5-bis(trifluoromethyl)benzoyl]-4-(benzyloxycarbonyl)-2-(2,3-dimethoxybenzyl)piperazine (0.81 g) in methanol (20 ml) was hydrogenated over 10% palladium-carbon (50% wet, 0.30 g) at room temperature under atmospheric pressure for 90 minutes. After removal of the catalyst by filtration, the filtrate was evaporated under reduced pressure to give colorless oil of 1-[3,5-bis(trifluoromethyl)benzoyl]-2-(2,3-dimethoxybenzyl)piperazine (0.64 g).

IR (KBr): 1645, 1635, 1281, 1184, 1134 cm$^{-1}$ NMR (CDCl$_3$, δ): 2.60–5.30 (10H, m), 3.81 (3H, s), 3.82 (3H, s), 6.40–7.10 (3H, m), 7.20–8.49 (3H, m)

MASS (APCI): 477 (M+H)$^+$

Preparation 51

(1) The following compound was obtained according to a similar manner to that of Preparation 46-(4).

1-Acetyl-3-[(1H-indol-2-yl)methylene]-2,5-piperazinedione

IR (KBr): 3332, 1714, 1685, 1668, 1419, 1221 cm$^{-1}$ NMR (DMSO-d$_6$, δ): 2.50 (3H, s), 4.38 (2H, s), 6.52–8.21 (6H, m), 9.84–12.00 (2H, br) MASS (APCI): 284 (M+H)$^+$ (2) The following compound was obtained according to a similar manner to that of Preparation 49-(2).

1-Acetyl-3-[(1H-indol-2-yl)methyl]-2,5-piperazinedione

IR (KBr): 3325, 1730, 1697, 1682, 1653, 1456, 1205 cm$^{-1}$ NMR (DMSO-d$_6$, δ): 2.43 (3H, s), 2.80–5.25 (5H, m), 6.18–8.73 (6H, m), 10.96 (1H, s) MASS (APCI): 286 (M+H)$^+$ (3) The following compound was obtained according to a similar manner to that of Preparation 49-(3).

3-[(1H-Indol-2-yl)methyl]-2,5-piperazinedione

IR (KBr): 3363, 3317, 1682, 1645, 1456, 1323 cm$^{-1}$ NMR (DMSO-d$_6$, δ): 3.03–3.61 (4H, m), 4.09–4.15 (1H, m), 6.18 (1H, s), 6.89–7.05 (2H, m), 7.31 (1H, d, J=7.9 Hz), 7.43 (1H, d, J=7.2 Hz), 7.99 (1H, s), 8.11 (1H, s), 10.85 (1H, s) MASS (APCI): 244 (M+H)$^+$ (4) The following compound was obtained according to a similar manner to that of Preparation 49-(4).

2-[(1H-Indol-2-yl)methyl]piperazine

IR (KBr): 3305, 2941, 1653, 1456 cm$^{-1}$ NMR (DMSO-d$_6$, δ): 1.80–3.70 (11H, m), 6.12 (1H, s), 6.87–7.02 (2H, m), 7.27 (1H, d, J=7.9 Hz), 7.40 (1H, d, J=6.9 Hz), 10.89 (1H, s) MASS (APCI): 216 (M+H)$^+$ (5) The following compound was obtained according to a similar manner to that of Preparation 49-(5).

1-(Benzyloxycarbonyl)-3-[(1H-indol-2-yl)methyl]piperazine

IR (KBr): 3303, 2908, 1697, 1684, 1456, 1433, 1248 cm$^{-1}$ NMR (DMSO-d$_6$, δ): 2.34–2.90 (8H, m), 3.78–3.89 (2H, m), 5.03 (2H, s), 6.17 (1H, s), 6.90–7.04 (2H, m), 7.26–7.43 (7H, m), 10.93 (1H, s) MASS (APCI): 350 (M+H)$^+$

Preparation 52

The following compound was obtained according to a similar manner to that of Preparation 50.

1-[3,5-Bis((trifluoromethyl)benzoyl]-2-[(1H-indol-2-yl)methyl]piperazine

IR (KBr): 1653, 1647, 1635, 1281, 1184, 1136 cm$^{-1}$ NMR (DMSO-d$_6$, δ): 2.50–4.90 (10H, m), 5.98–6.28 (1H, m), 6.90–7.42 (5H, m), 7.76–8.48 (2H, m), 10.59–11.03 (1H, m) MASS (APCI) 456 (M+H)$^+$

Preparation 53

(1) The following compound. was obtained according to a similar manner to that of Preparation 46-(4).

1-Acetyl-3-(3-methoxyphenyl)methylene-2,5-piperazinedione

NMR (DMSO-d$_6$, δ): 2.50 (3H, s), 3.79 (3H, s), 4.36 (2H, s), 6.9–7.0 (2H, m), 7.1–7.2 (2H, m), 7.3–7.4 (1H, m), 10.4 (1H, br s) MASS (APCI): 275 (M+H)$^+$ (2) The following compound was obtained according to a similar manner to that of Preparation 49-(2).

1-Acetyl-3-(3-methoxybenzyl)-2,5-piperazinedione

NMR (DMSO-d$_6$, δ): 2.42 (3H, s), 2.9–3.1 (2H, m), 3.33 (1H, d, J=17 Hz), 3.71 (3H, s), 4.02 (1H, d, J=17 Hz), 4.3–4.4 (1H, m), 6.7–6.9 (3H, m), 7.1–7.3 (1H, m), 8.43 (1H, br s) MASS (APCI): 277 (M+H)$^+$ (3) The following compound was obtained according to a similar manner to that of Preparation 49-(3).

3-(3-Methoxybenzyl)-2,5-piperazinedione

NMR (DMSO-d$_6$, δ): 2.8–3.5 (4H, m), 3.71 (3H, s), 4.0–4.1(1H, m), 6.7–6.9 (3H, m), 7.1–7.3 (1H, m), 7.91 (1H,br s), 8.13 (1H, br s) MASS (APCI): 235 (M+H)$^+$ (4) The following compound was obtained according to a similar manner to that of Preparation 49-(4).

2-(3-Methoxybenzyl)piperazine

NMR (DMSO-d$_6$, δ): 2.2–2.9 (9H, m), 3.5–3.8 (2H, m), 3.73 (3H, s), 6.7–6.8 (3H, m), 7.1–7.3 (1H, m) MASS (APCI): 207 (M+H)$^+$ (5) A solution of di-tert-butyl dicarbonate (1.99 g) in tetrahydrofuran (20 ml) was added dropwise to a mixture of 2-(3-methoxybenzyl)piperazine (1.88 g) and triethylamine (1.90 ml) in tetrahydrofuran (19 ml) with ice-water cooling. After 1 hour of stirring, ethyl acetate (100 ml) and water (50 ml) were added to the mixture. The organic layer was separated, washed with brine, dried over sodium sulfate, and evaporated in vacuo. The residue was purified by column chromatography on silica gel using a mixture-of dichloromethane and methanol (40:1) to give 2-(3-methoxybenzyl)-4-(tert-butoxycarbonyl)piperazine (1.18 g) as an oil.

NMR (DMSO-d$_6$, δ): 1.34 (9H, s), 2.1–2.9 (8H, m), 3.6–3.8 (2H, m), 3.73 (3H, s), 6.7–6.8 (3H, m), 7.1–7.3 (1H, m) MASS (APCI): 307 (M+H)$^+$ (6) The following compound was obtained according to a similar manner to that of Example 86.

1-[3,5-Bis(trifluoromethyl)benzoyl]-4-tert-butoxycarbonyl-2-(3-methoxybenzyl)piperazine NMR (DMSO-d$_6$, δ): 1.44 (9H, s), 2.5–5.0 (12H, m), 6.5–8.3 (7H, m) MASS (APCI): 447 (M+H)$^+$ (7) The following compound was obtained according to a similar manner to that of Preparation 35.

1-[3,5-Bis(trifluoromethyl-)benzoyl]-3-(3-methoxybenzyl)piperazine hydrochloride NMR (DMSO-d$_6$, δ): 2.7–5.2 (12H, m), 6.4–8.3 (7H, m), 9.4–10.2 (2H, m) MASS (APCI): 447 (M+H)$^+$ (free)

Preparation 54

(1) 3,4-Dimethylbenzyl chloride (10.2 g) and diethyl acetamidomalonate (14.3 g) were added successively into a solution of sodium ethoxide (4.94 g) in ethanol. The mixture was stirred under reflux for 2 hours and filtered through Celite®. The filtrate was concentrated under reduced pressure to give crystals which were collected by filtration and washed with isopropyl ether to give colorless crystals of diethyl 2-acetylamino-2-(3,4-dimethylbenzyl)malonate (11.8 g).

mp: 107–109° C. IR (KBr): 3335, 3275, 1750, 1645, 1520, 1460, 1380, 1280, 1185 cm$^{-1}$ NMR (DMSO-d$_6$, δ): 1.17 (6H, t, J=7.2 Hz), 1.90–1.93 (3H, m), 2.02–2.20 (6H, mn), 3.30–3.50 (3H, m), 4.14 (2H, q, J=7.2 Hz), 6.60–7.05 (3H, m), 7.97, 8.07 (1H, 2s) MASS (EI): 335 (M)$^+$, 276, 119

(2) Diethyl 2-acetylamino-2-(3,4-dimethylbenzyl) malonate (13.8 g) and potassium hydroxide (2.76 g) were dissolved into a mixed solution of ethanol (138 ml) and water (138 ml) and the solution was stirred under reflux for 8.5 hours. After being cooled to room temperature, the solution was concentrated under reduced pressure and the resulting aqueous solution was adjusted to pH 10 with aqeuous saturated sodium hydrogen carbonate solution. The solution was washed with ethyl acetate and made acidic with diluted hydrochloric acid, and extracted with ethyl acetate. The extract was dried over magnesium sulfate and evaporated under reduced pressure to give crystals of N-acetyl-3, 4-dimethyl-DL-phenylalanine (5.42 g).

mp: 136–139° C. IR (Nujol): 3337, 2700–2400, 1710, 1610, 1540, 1450, 1380, 1355 cm$^{-1}$ NMR (DMSO-d$_6$, δ): 1.67 (3H, s), 2.17–2.21 (6H, m), 2.60–3.15 (2H, m), 4.25–4.40 (1H, m), 6.90–7.05 (3H, m), 8.10–8.25 (1H, m)

MASS (EI): 235 (M)$^+$, 176, 119

(3) N-Acetyl-3,4-dimethylphenyl-DL-alanine (498.0 g) was dissolved into a mixture of 1N sodium hydroxide (2.12 L) and water (2.49 L). Cobalt dichloride hexahydrate (2.49 g) and acylase (Acylase Amano 15000, 24.9 g) were added to the solution and the mixture was stirred at 37° C. for 20 hours with controlling the pH of the reaction mixture to 7.5 with 1N sodium hydroxide. The resulting precipitates were collected by filtration and washed with water (500 ml×2) to give crystals of L-3,4-dimethylphenylalanine (120.7 g). The pH of the filtrate was adjusted to 1 with aqueous diluted hydrochloric acid and the solution was extracted with ethyl acetate. The extract was dried over magnesium sulfate and evaporated under reduced pressure to give a solid of N-acetyl-3,4-dimethylphenyl-D-alanine (160.72 g).

mp: 156–159° C. IR (Nujol): 3400, 3350, 2500–2400, 1710, 1620, 1560, 1450 cm$^{-1}$ NMR (DMSO-d$_6$, δ): 1.78 (3H, s), 2.16 (6H, s), 2.68–3.20 (2H, m), 4.28–4.40 (1H, m), 6.90–7.05 (3H, m), 8.18 (1H, d, J=8.0 Hz), 12.61 (1H, s) MASS (EI): 235 (M)$^+$, 176, 119

(4) A solution of N-acetyl-3,4-dimethylphenyl-D-alanine (5.0 g) in a mixture of concentrated hydrochloric acid (50 ml) and acetic acid (50 ml) was stirred under reflux for 20 hours. After being cooled to room temperature, the resulting precipitates were collected by filtration and washed with ethyl acetate to give colorless crystals of 3,4-dimethylphenyl-D-alanine hydrochloride (3.75 g).

mp: >250° C. [α]$_D^{26}$: -3.3° (C=1.0, MeOH) IR (Nujol): 2800–2400, 1730, 1600, 1500, 1480 cm$^{-1}$ NMR (DMSO-d$_6$, δ): 2.19 (6H, s), 3.07 (2H, d, J=6.2 Hz), 4.07 (1H, t, J=6.2 Hz), 6.90–7.10 (3H, m), 8.30–8.60 (3H, m) MASS (APCI): 194 (M+H)$^+$ (free)

(5) Thionyl chloride (5.4 ml) was added dropwise to methanol (60 ml) below 5° C. with ice-salt bath cooling and stirring was continued for 10 minutes at the same temperature. 3,4-Dimethylphenyl-D-alanine hydrochloride (5.0 g) was added to the mixture by small portions over 20 minutes at -15° C. and the whole was stirred at room temperature for 6 hours, and evaporated under reduced pressure. The resulting solid was triturated with isopropyl ether to give colorless crystals of 3,4-dimethylphenyl-D-alanine methyl ester hydrochloride (5.10 g).

mp: 190.0–190.5° C. [α]$_d^{30}$: -10.36° (C=0.55, MeOH) IR (Nujol): 3400, 1735 cm$^{-1}$ NMR (DMSO-d$_6$, δ): 2.19 (6H, s), 3.03 (1H, dd, J=7.3, 14.0 Hz), 3.15 (1H, dd, J=5.7, 14.0 Hz), 3.66 (3H, s), 4.16 (1H, dd, J=7.3, 5.7 Hz), 6.93 (1H, d, J=7.6 Hz), 6.99 (1H, s), 7.08 (1H, d, J=7.6 Hz), 8.78 (3H, s) MASS (APCI): 208 (M+H)$^+$ (free)

(6) Potassium carbonate (5.45 g) was added by small portions with ice-cooling to a mixture of 3,4-dimethylphenyl-D-alanine methyl ester hydrochloride (4.81 g) in a mixed solvent of dichloromethane and water. Chloroacetyl chloride (2.20 ml) was added to the mixture below 5° C. over 10 minutes and the whole was stirred for 30 minutes. The organic layer was separated, washed with brine, dried over magnesium sulfate, and evaporated under reduced pressure to give an oil of methyl (2R)-2-(2-chloroacetylamino)-3-(3,4-dimethylphenyl)propionate (6.01 g).

IR (Neat): 3400, 1735, 1650, 1460 cm$^{-1}$ NMR (CDCl$_3$, δ): 2.22 (6H, 5), 3.08 (1H, d, J=5.7 Hz), 3.74 (3H, s), 4.02 (2H, s), 4.77–4.87 (1H, m), 6.80–7.10 (4H, m) MASS (APCI): 283 (M+H)$^+$, 441

(7) Benzylamine (5.4 ml) and potassium carbonate (4.08 g) were added successively to a solution of methyl (2R)-2-(2-chloroacetylamino)-3-(3,4-dimethylphenyl)propionate (5.33 g) in N,N-dimethylformamide (25 ml) at 20° C. After 3 hours of stirring at 35° C., the mixture was poured into a mixture of ice-water (40 ml) and dichloromethane (40 ml). After the mixture was adjusted to pH 6 with concentrated hydrochloric acid (ca. 1.4 ml), the organic layer was separated, washed with brine (20 ml), dried over magnesium sulfate, and evaporated under reduced pressure. The residue was triturated with n-hexane and filtered to give colorless powders of (3R)-1-benzyl-3-(3,4-dimethylbenzyl)-2,5-piperazinedione (1.51 g). The filtrate was evaporated under reduced pressure to give an oil of methyl (2R)-2-[(2-benzylaminoacetyl)amino]-3-(3,4-dimethylphenyl) propionate (5.67 g).

IR (Neat) 3400, 1735, 1650, 1460 cm$^{-1}$ NMR (CDCl$_3$, δ): 2.12–2.21 (6H, m), 3.04–3.10 (2H, m), 3.29 (2H, d, J=2.0 Hz), 3.66 (2H, s), 3.74 (3H, s), 4.80–4.90 (1H, m), 6.80–7.40 (9H, m), 7.90–8.05 (1H, m) MASS (APCI): 355 (M+H)$^+$ (8) A mixture of methyl (2R)-2-[(2-benzylaminoacetyl) amino]-3-(3,4-dimethylphenyl)propionate (2.5 g) and acetic acid (0.2 ml) in isopropyl alcohol (8.8 ml) was stirred for 5 hours under reflux. After being cooled to room temperature, isopropyl ether was added to the mixture. The resulting precipitates were collected by filtration and washed with isopropyl ether to give colorless crystals of (3R)-1-benzyl-3-(3,4-dimethylbenzyl)-2,5-piperazinedione (1.26 g).

mp: 191–192° C. [α]$_D^{25}$: -23.3° (C=1, DMF) IR (Nujol): 3180, 1640, 1500, 1340 cm$^{-1}$ NMR (DMSO-d$_6$, δ): 2.11 and 2.16 (3H, 2s), 2.82 (1H, dd, J=4.8, 13.5 Hz), 3.13 (1H, dd, J=4.2, 13.5 Hz), 2.76 (1H, d, J=17.1 Hz), 3.46 (1H, d, J=17.1 Hz), 4.22 (1H, d, J=14.5 Hz), 4.55 (1H, d, J=14.5 Hz), 4.2–4.3 (1H, m), 6.7–6.9 (3H, m), 7.0–7.1 (2H, m), 7.2–7.3 (3H, m), 8.31 (1H, s) MASS: 323 (M+1)

(9) The following compound was obtained according to a similar manner to that of Preparation 49-(4).

(3R)-1-Benzyl-3-(3,4-dimethylbenzyl)piperazine

IR (Neat): 3000–2750, 1670, 1500, 1450, 1360, 1320 cm$^{-1}$ NMR (CDCl$_3$, δ): 2.26 (6H, m), 1.8–3.0 (9H, m), 3.4–3.6 (2H, m), 6.9–7.1 (3H, m), 7.2–7.5 (5H, m) MASS: 295 (M+1)

its hydrochloride mp: 186–188° C. $[\alpha]_D^{29.2}$: +12.72° (C=0.55, MeOH) IR (Nujol): 3500, 2350 cm$^{-1}$ NMR (DMSO-d$_6$, δ): 2.20 (6H, s), 2.73–3.90 (9H, m), 4.34 (1H, d, J=13.1 Hz), 4.42 (1H, d, J=13.1 Hz), 6.97 (1H, d, J=7.6 Hz), 7.02 (1H, s), 7.11 (1H, d, J=7.6 Hz), 7.36–7.65 (5H, m) MASS (APCI): 295 (M+H)$^+$ (free)

(10) The following compound was obtained according to a similar manner to that of Example 86.

(2R)-1-[3,5-Bis(trifluoromethyl)benzoyl]-2-(3,4-dimethylbenzyl)-4-benzylpiperazine IR (Neat): 3000–2700, 1640, 1500, 1430, 1350 cm$^{-1}$ NMR (CDCl$_3$, δ): 2.1–2.3 (6H, m), 2.1–2.2 (2H, m), 2.6–3.7 (8H, m), 4.5–5.1 (1H, m), 6.5–6.7 (2H, m), 6.9–7.6 (7H, m), 7.8–7.9 (2H, m) MASS: 535 (M+1)

(11) A mixture of (2R)-1-[3,5-bis(trifluoromethyl) benzoyl]-2-(3,4-dimethylbenzyl)-4-benzylpiperazine (2.94 g), ammonium formate (1.74 g) and 10% palladium-carbon (0.58 g) in a mixed solvent of methanol (11.8 ml), water (5.9 ml) and tetrahydrofurane (10 ml) was stirred for 5.5 hours at 50° C. under nitrogen atmosphere. The reaction mixture was cooled to room temperature and filtered through Celite® pad. The filtrate was concentrated under reduced pressure and the residue was dissolved in ethyl acetate. The solution was washed with water and brine, dried over magnesium sulfate, and evaporated under reduced pressure. The residue was dissolved in methanol and treated with fumaric acid (468 mg) to give colorless powder of fumaric acid salt (1:1) of (2R)-1-[3,5-bis(trifluoromethyl)benzoyl]-2-(3,4-dimethylbenzyl)piperazine (0.24 g).

mp: 186–188° C. $[\alpha]_D^{31}$: −23.99° (C=0.55, MeOH) IR (Nujol) 2320, 1720, 1705, 1630, 1270 cm$^{-1}$ NMR (DMSO-d$_6$, δ): 1.57–2.34 (6H, m), 2.56–5.08 (9H, m), 6.10–8.52 (11H, m) MASS (APCI): 445 (M+H)$^+$ (free)

Preparation 55

(1) Benzaldehyde (17.4 ml) was added dropwise to a solution of 2-amino-2-methyl-1,3-propanediol (20 g) in methanol (200 ml) at 0° C. and the whole was stirred at room temperature for 2 hours. Sodium borohydride (11.5 g) was added thereto in portions at 0° C. and the mixture was stirred for 10 minutes. 1N Sodium hydroxide solution and ethyl acetate were added and the organic layer was separated, dried over magnesium sulfate, and evaporated in vacuo to give 2-benzylamino-2-methyl-1,3-propanediol (28.54 g).

NMR (CDCl$_3$, δ): 1.08 (3H, s), 3.54 (4H, s), 3.73 (2H, s), 7.20–7.45 (5H, m) MASS (APCI): 196 (M+H)$^+$ (2) Chloroacetyl chloride (14.0 ml) was added dropwise to a mixture of 2-benzylamino-2-methyl-1,3-propanediol (28.5 g), potassium carbonate (30.3 g) in dichloromethane (150 ml) and water (150 ml) at 0° C., and the whole was stirred at room temperature for 2 hours. The mixture was extracted with dichloromethane and the extract was washed successively with water, 1N hydrochloric acid and brine, dried over magnesium sulfate and evaporated in vacuo. The residue was dissolved in tert-butanol (400 ml) and the solution was added potassium tert-butoxide (16.38 g) portionwisely and the whole was refluxed for 30 minutes. After cooling, the solvent was removed by evaporation and ethyl acetate and water were added thereto. The organic layer was separated, dried over magnesium sulfate, and evaporated in vacuo. The residue was purified by column chromatography on silica gel with a mixture of ethyl acetate and n-hexane (1:1) as an eluent to give 4-benzyl-5-hydroxymethyl-5-methyl-3-morpholinone (10.89 g).

NMR (CDCl$_3$, δ): 1.12 (3H, s), 2.50 (1H, br s), 3.44 (1H, d, J=11.7 Hz), 3.56 (1H, d, J=11.9 Hz), 3.67 (1H, d, J=11.7 Hz), 3.98 (1H, d, J=11.9 Hz), 4.29 (2H, s), 4.67 (2H, s), 7.10–7.40 (5H, m) MASS (APCI): 236 (M+H)$^+$ (3) Sodium bis(2-methoxyethoxy)aluminum hydride (3.46 M solution in toluene; 42 ml) was added to a solution of 4-benzyl-5-hydroxymethyl-5-methyl-3-morpholinone (10.77 g) in toluene (100 ml) at 0° C. under nitrogen atmosphere and the whole was stirred at room temperature for 1 hour. Ethanol (20 ml) was added to the mixture at 0° C. and the pH of the mixture was adjusted to 12 by 1N sodium hydroxide solution. The organic layer was separated, added 1N hydrochloric acid and the acidic aqueous layer was separated. This procedure was repeated twice and the combined aqueous layer was made alkaline with 4 M sodium hydroxide solution. It was extracted with ethyl acetate, dried over magnesium sulfate and evaporated in vacuo to give 4-benzyl-3-hydroxymethyl-3-methylmorpholine (9.35 g) as an oil.

NMR (CDCl$_3$, δ): 1.12 (3H, s), 2.50–2.64 (2H, m), 3.10–4.05 (8H, m), 7.20–7.50 (5H, m) MASS (APCI): 222 (M+H)$^+$ (4) A solution of 4-benzyl-3-hydroxymethyl-3-methylmorpholine (1 g) in tetrahydrofuran (10 ml) was added dropwise to a suspension of sodium hydride (60% oil suspension; 0.27 g) in tetrahydrofuran (20 ml) at room temperature under nitrogen atmosphere and the whole was stirred at 70° C. for 1 hour. After cooling, methyl iodide (0.34 ml) was added to the mixture and the whole was stirred at 40° C. for 1 hour. After cooling, ethyl acetate and water were added to the mixture and the organic layer was separated, dried over magnesium sulfate and evaporated in vacuo. The residue was purified by column chromatography on silica gel with a mixture of ethyl acetate and n-hexane (1:4) as an eluent to give 4-benzyl-3-methoxymethyl-3-methylmorpholine (0.77 g) as an oil.

NMR (CDCl$_3$, δ): 1.15 (3H, s), 2.30–2.64 (2H, m), 3.20–3.70 (8H, m), 3.36 (3H, s), 7.14–7.40 (5H, m) MASS (APCI): 236 (M+H)$^+$ (5) A solution of 4-benzyl-3-methoxymethyl-3-methylmorpholine (0.77 g) in methanol (20 ml) was hydrogenated in the presence of 10% palladium-carbon (80 mg) at room temperature. After 1 hour, palladium-carbon was removed by filtration and the filtrate was evaporated in vacuo. The residue was dissolved in ethyl acetate (20 ml) and the solution was added 4N hydrogen chloride in ethyl acetate (4.08 ml). The mixture was evaporated in vacuo to give 3-methoxymethyl-3-methylmorpholine hydrochloride (0.4 g) as a white solid.

mp: 80–90° C. IR (KBr): 3240–3270, 2976, 1090, 1049 cm$^{-1}$ NMR (DMSO-d$_6$, δ): 1.29 (3H, s), 3.00–3.92 (8H, m), 3.36 (3H, s) MASS (APCI) 146 (M+H)$^+$ (free)

Preparation 56

(1) A solution of (3R)-4-benzyl-3-hydroxymethylmorpholine (0.94 g) in tetrahydrofuran (10 ml) was added dropwise to a suspension of sodium hydride (60% oil suspension, 0.22 g) in tetrahydrofuran (20 ml) at room temperature under nitrogen atmosphere and the whole was stirred at 70° C. for 1 hour. After cooling, methyl iodide (0.31 ml) was added thereto and the mixture was stirred at 40° C. for 1 hour. After cooling, the mixture was poured into ice water, and extracted with ethyl acetate. The extract was dried over magnesium sulfate and evaporated in vacuo. The residue was purified by column chromatography on silica gel with a mixture of ethyl acetate and n-hexane (3:7) as an eluent to give (3R)-4-benzyl-3-methoxymethylmorpholine (0.88 g) as an oil.

NMR (CDCl$_3$, δ): 2.20–2.40 (1H, m), 2.56–2.86 (2H, m), 3.26–4.26 (8H, m), 3.34 (3H, s), 7.20–7.48 (5H, m) MASS (APCI): 222 (M+H)$^+$ (2) The following compound was obtained according to a similar manner to that of Preparation 55-(5).

(3R)-3-Methoxymethylmorpholine hydrochloride mp: 150–152° C. $[\alpha]_D^{27}$: +16.31° (C=0.42, MeOH) IR (KBr): 2964, 2947, 2929, 2897, 2887, 2835, 2810, 2789, 2765, 2727, 2698, 2490, 1450, 1311, 1194, 1136, 1111, 1095 cm$^{-1}$ NMR (DMSO-d$_6$, δ): 2.94–3.24 (2H, m), 3.31 (3H, s), 3.36–3.78 (5H, m), 3.80–3.98 (2H, m), 9.52 (2H, br s) MASS (APCI): 132 (M+H)$^+$ (free)

Preparation 57

(1) The following compound was obtained according to a similar manner to that of Preparation 56-(1).

(3S)-4-Benzyl-3-methoxymethylmorpholine

NMR (CDCl$_3$, δ): 2.15–2.34 (1H, m), 2.54–2.72 (2H, m), 3.33 (3H, s), 3.33 (1H, d, J=13.5 Hz), 3.40–3.90 (6H, m), 4.07 (1H, d, J=13.5 Hz), 7.18–7.40 (5H, m) MASS (APCI): 222 (M+H)$^+$ (2) The following compound was obtained according to a similar manner to that of Preparation 55-(5).

(3S)-3-Methoxymethylmorpholine hydrochloride mp: 150–152° C. $[\alpha]_D^{27}$: −14.70° (C=0.50, MeOH) IR (KBr): 2964, 2947, 2929, 2887, 2833, 2810, 2789, 2765, 2727, 2698, 2490, 1450, 1311, 1194, 1136, 1111, 1095, 1041 cm$^{-1}$ NMR (DMSO-d$_6$, δ): 2.94–3.24 (2H, m), 3.31 (3H, s), 3.38–3.75 (5H, m), 3.84–3.96 (2H, m), 9.45 (2H, br s) MASS (APCI): 132 (M+H)$^+$ (free)

Preparation 58

(1) The following compound was obtained according to a similar manner to that of Preparation 56-(1).

(3S)-4-Benzyl-3-ethoxymethylmorpholine

NMR (CDCl$_3$, δ): 1.20 (3H, t, J=7.0 Hz), 2.15–2.40 (1H, m), 2.54–2.84 (2H, m), 3.24–4.20 (10H, m), 7.20–7.45 (5H, m) MASS (APCI): 236 (M+H)$^+$ (2) The following compound was obtained according to a similar manner to that of Preparation 55-(5).

(3S)-3-Ethoxymethylmorpholine hydrochloride mp: 100–115° C. $[\alpha]_D^{27}$: −13.07° (C=0.505, MeOH) IR (KBr): 2976, 2922, 2900, 2866, 2790, 2767, 2746, 2721, 2468, 1458, 1450, 1435, 1309, 1176, 1147, 1126, 1101, 1043, 1030 cm$^{-1}$ NMR (DMSO-d$_6$, δ): 1.15 (3H, t, J=7.0 Hz), 2.94–3.28 (2H, m), 3.28–3.80 (7H, m), 3.80–4.00 (2H, m), 9.47 (2H, br s) MASS (APCI): 146 (M+H)$^+$ (free)

Preparation 59

The following compound was obtained according to a similar manner to that of Preparation 55-(5).

(3S)-3-Hydroxymethylmorpholine hydrochloride mp: 123–126° C. $[\alpha]_D^{27}$: −15.80° (C=0.44, MeOH) IR (KBr): 3290–3480, 2945, 1105, 1047 cm$^{-1}$ NMR (DMSO-d$_6$, δ): 2.86–4.00 (9H, m), 5.41 (1H, br s), 9.25 (1H, br s), 9.56 (1H, br s) MASS (APCI) 118 (M+H)$^+$ (free)

Preparation 60

(1) Hexafluoropropene diethylamine complex (1.58 ml) was added dropwise to a solution of (3R)-4-benzyl-3-hydroxymethylmorpholine (1.5 g) in dichloromethane (100 ml) at −30° C. under nitrogen atmosphere and the whole was stirred at room temperature for 3 hours. The solution was washed with water and saturated sodium hydrogen carbonate solution, dried over magnesium sulfate and evaporated in vacuo. The residue was dissolved in methanol (100 ml) and the solution was added 30% sodium methoxide solution in methanol (2.9 ml). After 30 minutes of stirring, acetic acid (0.9 ml) was added to the mixture and the whole was evaporated in vacuo. Dichloromethane and water were added to the residue and the organic phase was separated, dried over magnesium sulfate, and evaporated in vacuo. The reside was purified by column chromatography on silica gel to give a crude mixture (2.26 g) containing mainly (3R)-4-benzyl-3-fluoromethylmorpholine and 4-benzyl-6-fluoroperhydro-1,4-oxazepine. The obtained mixture was used to the next reaction without further purification.

(2) The crude mixture (2.2 g) obtained by the previous procedure, which contained mainly (3R)-4-benzyl-3-fluoromethylmorpholine and 4-benzyl-6-fluoroperhydro-1,4-oxazepine, was dissolved in methanol (50 ml). The solution was hydrogenated in the presence of 10% palladium-carbon (200 mg) at room temperature. After 1 hour of stirring, palladium-carbon was removed by filtration and the filtrate was evaporated under reduced pressure. The two isomers were separated by column chromatography using 2% of methanol in dichloromethane as an eluent to give (3R)-3-fluoromethylmorpholine and 6-fluoroperhydro-1,4-oxazepine (the former was less polar). The products were converted to their hydrochloride as a conventional manner using 4N hydrogen chloride in ethyl acetate, respectively.

(3R)-3-Fluoromethylmorpholine hydrochloride (0.21 g)

NMR (DMSO-d$_6$, δ): 3.02–3.34 (2H, m), 3.48–3.82 (3H, m), 3.82–4.10 (2H, m), 4.57 (1H, d, J=4.0 Hz), 4.80 (1H, d, J=4.0 Hz), 9.84 (2H, br s) MASS (APCI): 120 (M+H)$^+$ (free)

6-Fluoroperhydro-1,4-oxazepine hydrochloride (0.26 g)

NMR (DMSO-d$_6$, δ): 3.10–3.32 (2H, m), 3.40–3.60 (2H, m), 3.68–4.16 (4H, m), 4.94–5.30 (1H, m) MASS (APCI): 120-(M+H)$^+$ (free)

Preparation 61

Triphenylphosphine (7.31 g) was added to a solution of carbon tetrabromide (4.62 g) in dichloromethane (15 ml) at 0° C. and the mixture was stirred at 0° C. for 15 minutes. A solution of (3S)-4-tert-butoxycarbonyl-3-formylmorpholine (1.5 g) in dichloromethane (15 ml) was added dropwise to the solution over 10 minutes at 0° C. and stirred for 3 hours, and the mixture was added saturated sodium hydrogen carbonate solution. The organic layer was separated and the aqueous layer was extracted with ethyl acetate three times. The combined organic layer was washed with brine, dried over magnesium sulfate, and evaporated under reduced pressure. The residue was purified by column chromatography on silica gel using a mixture of ethyl acetate and n-hexane (4:6) to give (3R)-4-tert-butoxycarbonyl-3-(2,2-dibromoethenyl)morpholine as an oil.

This oil was dissolved in tetrahydrofuran (15 ml) and butyllithium (1.62 M in hexane, 9.45 ml) was added to the solution at −78° C. After 30 minutes of stirring at −78° C., the mixture was quenched with-water and extracted with ethyl acetate twice. The combined organic layer was washed with brine, dried over magnesium sulfate, and evaporated under reduced pressure. The residue was purified by column chromatography on silica gel using a mixture of ethyl acetate and hexane (2:8) to give (3R)-4-tert-butoxycarbonyl-3-ethynylmorpholine (1.385 g) as a pale yellow oil.

NMR (CDCl$_3$, δ): 1.48 (9H, s), 2.31 (1H, d, J=2.3 Hz), 3.19–3.96 (6H, m), 4.74 (1H, br s) MASS (APCI): 112 (M-Boc)$^+$

Preparation 62

(1) The following compound was obtained according to a similar manner to that of Preparation 55-(5).

(3S)-3-Ethoxycarbonylmorpholine hydrochloride

NMR (CDCl$_3$, δ): 1.33 (3H, t, J=7.1 Hz), 3.20–3.75 (2H, m), 3.90–4.30 (5H, m), 4.32 (2H, q, J=7.1 Hz), 10.04 (1H, br s), 10.74 (1H, br s) MASS (APCI): 160 (M+H)$^+$ (free)

(2) A mixture of (3S)-3-ethoxycarbonylmorpholine hydrochloride (0.3 g), propargyl bromide (0.34 ml) and potassium carbonate (0.91 g) in N,N-dimethylformamide (10 ml) was stirred at room temperature for 1 hour and then the solvent was removed under reduced pressure. Ethyl acetate and sodium hydrogen carbonate solution were added to the residue and the organic layer was separated, dried over magnesium sulfate, and evaporated in vacuo. The residue was purified by column chromatography on silica gel with a mixture of ethyl acetate and n-hexane (3:7) as an eluent to give (3S)-3-ethoxycarbonyl-4-(2-propynyl)morpholine (0.22 g) as an oil.

NMR (CDCl$_3$, δ): 1.29 (3H, t, J=7.1 Hz), 2.28 (1H, t, J=2.5 Hz), 2.70–2.95 (2H, m), 3.40–4.05 (7H, m), 4.21 (2H, q, J=7.1 Hz) MASS (APCI): 198 (M+H)$^+$

Preparation 63

(1) Sodium triacetoxyborohydride (4.63 g) was added portionwisely to a mixture of (R)-(-)-2-amino-1-butanol (1.5 g) and benzaldehyde (1.79 g) in dichloromethane (50 ml) at 0° C. and the whole was stirred at room temperature overnight. The mixture was washed with sodium carbonate solution and brine, dried over sodium sulfate, and evaporated in vacuo to give (R)-2-benzylamino-1-butanol (2.69 g) [IR (Neat): 3292, 1460, 1350, 1136, 1061 cm$^{-1}$]. A solution of chloroacetyl chloride (2.1 g) in tetrahydrofuran (4 ml) was added to a mixture of the obtained oil (2.69 g) and potassium carbonate (4.6 g) in a mixture of acetone (20 ml) and water (20 ml) at 0° C. After 1 hour of stirring, the solvent was replaced with ethyl acetate. The organic layer was separated, washed with brine, dried over sodium sulfate, and evaporated in vacuo. The residue was purified by column chromatography on silica gel to give N-benzyl-N-[(2R)-2-(1-hydroxybutyl)]-2-chloroacet amide (2.73 g) [IR (Neat): 3430, 1640, 1450, 1420, 1355, 1045 cm$^{-1}$, MASS (APCI): 256 (M+H)$^+$, 220] as an oil. Potassium tert-butoxide (1.22 g) was added to a solution of the above obtained oil (2.7 g) in tert-butanol (20 ml) portionwisely at room temperature and the whole was stirred overnight. The mixture was evaporated in vacuo, and ethyl acetate and water were added to the residue. The organic layer was separated, washed with brine, dried over sodium sulfate, and evaporated in vacuo to give (5R)-4-benzyl-5ethyl-3-morpholinone (2.33 g) as an oil.

IR (Neat): 1655, 1640, 1450, 1430, 1360, 1340, 1260, 1155, 1128 cm$^{-1}$ NMR (CDCl$_3$, δ): 0.91 (3H, t, J=7.5 Hz), 1.60–1.96 (2H, m), 2.94–3.14 (1H, m), 3.55–3.94 (2H, m)? 3.92 (1H, d, J=15.0 Hz), 4.21 (1H, d, J=16.7 Hz), 4.31 (1H, d, J=16.7 Hz), 5.43 (1H, d, J=15.0 Hz), 7.20–7.44 (5H, m) MASS (APCI): 220 (M+H)$^+$ (2) A solution of (5R)-4-benzyl-5-ethyl-3-mrorpholinone (2.3 g) in tetrahydrofuran (7 ml) was added portionwisely to a suspension of lithium aluminum hydride (0.4 g) in tetrahydrofuran (15 ml) and the whole was refluxed for 2 hours. After cooling, 50% aqueous tetrahydrofuran solution (4 ml) was added thereto and stirring was continued for 15 minutes. The mixture was filtered through Celite® pad, and the pad was washed with tetrahydrofuran. The combined filtrate was evaporated in vacuo and the residue was purified by column chromatography on silica gel to give (3R)-4-benzyl-3-ethylmorpholine (1.44 g) as an oil.

IR (Neat): 1495, 1450, 1355, 1130, 1060 cm$^{-1}$ NMR (CDCl$_3$, δ): 0.93 (3H, t, J=7.5 Hz), 1.44–1.94 (2H, m), 2.08–2.45 (2H, m), 2.54–2.70 (1H, m), 3.15 (1H, d, J=13.3 Hz), 3.55–3.86 (4H, m), 4.06 (1H, d, J=13.3 Hz), 7.15–7.40 (5H, m) MASS (APCI): 205 (M+H)$^+$ A solution of the obtained oil (1.44 g) in ethanol (15 ml) was hydrogenated using 10% palladium-carbon (200 mg) at atmospheric pressure. After the reaction was completed (7 hours), the catalyst was removed by filtration. The filtrate was added 4N hydrogen chloride in ethyl acetate (2.5 ml) and the whole was evaporated in vacuo. The residue was triturated with ethyl acetate and the resulting precipitates were collected by filtration and dried to give (3R)-3-ethylmorpholine hydrochloride (1.0 g).

mp: 223–225° C. [α]$_D^{28}$: +9.5° (C=0.5, MeOH) IR (KBr): 2729, 2696, 2472, 1458, 1427, 1360, 1313, 1109, 1061 cm$^{-1}$ NMR (DMSO-d$_6$, δ): 0.93 (3H, t, J=7.5 Hz), 1.40–1.78 (2H, m), 2.88–3.55 (4H, m), 3.60–4.04 (3H, m), 9.60 (2H, br s) MASS (APCI): 116 (M+H)$^+$ (free)

Preparation 64

(1) The following compound was obtained according to a similar manner to that of Preparation 63-(1).

(3S)-4-Benzyl-5-ethyl-3-morpholinone

IR (Neat): 1653, 1462, 1348, 1263, 1155, 1122 cm$^{-1}$ NMR (CDCl$_3$, δ): 0.91 (3H, t, J=7.5 Hz), 1.60–1.96 (2H, m), 2.95–3.14 (1H, m), 3.58–3.94 (2H, m), 3.92 (1H, d, J=15.0 Hz), 4.21 (1H, d, J=16.7 Hz), 4.30 (1H, d, J=16.7 Hz), 5.43 (1H, d, J=15.0 Hz), 7.15–7.44 (5H, m) MASS (APCI): 220 (M+H)$^+$ (2) The following compound was obtained according to a similar manner to that of Preparation 63-(2).

(3S)-3-Ethylmorpholine hydrochloride mp: 221–224° C. [α]$_D^{26}$: -11.2° (C=0.5, MeOH) IR (KBr): 2729, 2625, 2472, 1454, 1356, 1313, 1109, 1061 cm$^{-1}$ NMR (DMSO-d$_6$, δ): 0.93 (3H, t, J=7.5 Hz), 1.40–1.78 (2H, m), 2.90–3.54 (4H, m), 3.60–4.04 (3H, m), 9.57 (2H, br s) MASS (APCI): 116 (M+H)$^+$ (free)

Preparation 65

A mixture of 7-oxa-4-azaspiro[2.5]octane hydrochloride (200 mg), 2-bromoethanol (0.28 ml) and potassium carbonate (550 mg) in N,N-dimethylformamide (2 ml) was stirred at 90° C. for 48 hours and cooled. The mixture was poured into brine and extracted with dichloromethane. The extract was dried over magnesium sulfate and evaporated under reduced pressure, and purified by column chromatography on silica gel using a mixture of methanol and chloroform (2:98) to give 4-(2-hydroxyethyl)-7-oxa-4-azaspiro[2.5]octane as an oil. This oil was dissolved in ethyl acetate (5 ml) and the solution was added methanesulfonyl chloride (0.16 ml) and triethylamine (0.3 ml). After 30 minutes of stirring at room temperature, the mixture was filtered, evaporated, and purified by column chromatography on silica gel using a mixture of ethyl acetate and n-hexane (20:80~30:70) to give 4-(2-chloroethyl)-7-oxa-4-azaspiro[2.5]octane (140 mg) as an oil.

NMR (CDCl$_3$, δ): 0.61–0.67 (2H, m), 0.95–1.05 (2H, m), 3.10–3.15 (2H, m), 3.22 (2H, t, J=6.9 Hz), 3.50 (2H, br s), 3.54–3.64 (2H, m), 3.80 (2H, t, J=4.7 Hz) MASS (APCI): 176 (M+H)$^+$

Preparation 66

A mixture of (3R)-3-ethylmorpholine hydrochloride (0.2 g), 1,4-dichloro-2-butyne (0.5 ml) and potassium carbonate (0.71 g) in N,N-dimethylformamide (10 ml) was stirred at room temperature for 2 hours. After removal of the solvent, ethyl acetate and sodium hydrogen carbonate solution were added thereto. The organic layer was separated and the aqueous layer was extracted with ethyl acetate twice. The combined organic layer was dried over magnesium sulfate and evaporated in vacuo. The residue was purified by column chromatography on silica gel with a mixture of ethyl acetate and n-hexane (1:1) as an eluent to give (3R)-4-(4-chloro-2-butynyl)-3-ethylmorpholine (0.2 g) as an oil.

NMR (CDCl$_3$, δ): 0.89 (3H, t, J=7.5 Hz), 1.20–1.74 (2H, m), 2.42–2.84 (3H, m), 3.20–3.90 (6H, m), 4.18 (2H, t, J=2.0 Hz) MASS (APCI): 202 (M+H)$^+$

Preparation 67

(1) A mixture of (3S)-3,5-dimethylmorpholine hydrochloride (8.3 g), di-tert-butyl dicarbonate (14.34 g) and sodium hydroxide (5.48 g) in water (30 ml) were stirred at room temperature overnight. Water (50 ml) and isopropyl ether were added to the mixture and the organic layer was separated, dried over magnesium sulfate, and evaporated in vacuo. The residue was purified by column chromatography on silica gel with a mixture of ethyl acetate and n-hexane (1:9) as an eluent to give (3S,5S)-4-tert-butoxycarbonyl-3,5-dimethylmorpholine (3.55 g) and meso-4-tert-butoxycarbonyl-3,5-dimethylmorpholine (2.84 g) (the former was less polar). (3S,5S)-4-tert-butoxycarbonyl-3,5-dimethylmorpholine (3.55 g) was dissolved in a mixture of dichloromethane (20 ml) and trifluoroacetic acid (20 ml) and the mixture was stirred at room temperature for 2 hours. After removal of the solvent under reduced pressure, 1N sodium hydroxide solution (20 ml) and dichoromethane were added thereto. The organic phase was separated, dried over magnesium sulfate, and was added 4N hydrogen chloride in ethyl acetate (20 ml). The mixture was evaporated in vacuo and the residue was triturated with a mixture of dichloromethane and isopropyl ether to give (3S,5S)-3,5-dimethylmorpholine hydrochloride (1.56 g) as a white solid.

mp: 172–173° C. $[\alpha]_D^{26}$: +16.37° (C=0.333, MeOH) IR (KBr): 3049, 2993, 2978, 2970, 2935, 2916, 2873, 2829, 2817, 2800, 2785, 2742, 2723, 1460, 1433, 1385, 1136, 1107, 1028 cm$^{-1}$ NMR (CDCl$_3$, δ): 1.50 (6H, d, J=6.5 Hz), 3.44–4.08 (6H, m), 9.97 (2H, br s) MASS (APCI): 116 (M+H)$^+$ (free)

meso-3,5-Dimethylmorpholine hydrochloride (2.84 g) was prepared from meso-4-tert-butoxycarbonyl-3,5-dimethylmorpholine in a similar manner to the preparation of (3S,5S)-3,5-dimethylmorpholine hydrochloride (1.84 g).

mp: 85–90° C. IR (KBr): 2981, 2945, 2929, 2873, 2860, 2808, 2802, 2773, 2748, 2735, 2727, 1672, 1624, 1205, 1182, 1138, 1117, 1057 cm$^{-1}$ NMR (CDCl$_3$, δ): 1.35 (6H, d, J=6.6 Hz), 3.22–4.00 (6H, m), 9.44 (1H, br s), 10.22 (1H, br s) MASS (APCI): 116 (M+H)$^+$ (free)

(2) The following compound was obtained according to a similar manner to that of Preparation 66.

(3S,5S)-4-(4-Chloro-2-butynyl)-3,5-dimethylmorpholine

NMR (CDCl$_3$, δ): 1.06 (6H, d, J=6.5 Hz), 2.95–3.14 (2H, m), 3.34–3.54 (4H, m), 3.72,(2H, dd, J=11.0, 3.1 Hz), 4.16 (2H, t, J=2.1 Hz) MASS (APCI): 202 (M+H)$^+$

Preparation 68

(1) The following compound was obtained according to a similar manner to that of Preparation 65.

2-(3,3-Dimethylmorpholin-4-yl)ethanol

NMR (DMSO-d$_6$, δ): 0.91 (6H, s), 2.3 (2H, t, J=6.7 Hz), 2.4–2.5 (2H, m), 3.19 (2H, s), 3.3–3.4 (2H, m), 3.5–3.6 (2H, m), 4.27 (1H, t, J=5.4 Hz) MASS (APCI): 160 (M+H)$^+$ (2) The following compound was obtained according to a similar manner to that of Preparation 65.

2-(3,3-Dimethylmorpholin-4-yl)ethyl methanesulfonate

The compound was used to the next step without further purification.

Preparation 69

The following compound was obtained according to a similar manner to that of Preparation 62-(2).

4-(3-Chloropropyl)-3,3-dimethylmorpholine

NMR (DMSO-d$_6$, δ): 0.92 (6H, s), 1.77 (2H, qui, J=6.4 Hz), 2.3–2.5 (4H, m), 3.19 (2H, s), 3.55–3.60 (2H, m), 3.67 (2H, t, J=6.4 Hz) MASS (APCI): 192 (M+H)$^+$ Preparation 70

(1) The following compound was obtained according to a similar manner to that of Preparation 53-(5) starting from (3R)-1-benzyl-3-[(1H-indol-3-yl)methyl]piperazine.

(2R)-4-Benzyl-1-tert-butoxycarbonyl-2-[(1H-indol-3-yl) methyl]piperazine mp: 143–145° C. IR (KBr): 3305, 2976, 2922, 2810, 1664, 1454, 1425, 1367, 1336, 1299, 1261, 1223 cm$^{-1}$ NMR (DMSO-d$_6$, δ): 1.00–1.50 (9H, m), 1.80–2.10 (2H, m), 2.60–4.30 (9H, m), 6.80–7.70 (10H, m), 10.72 (1H, br s) MASS (APCI): 406 (M+H)$^+$ (2) The following compound was obtained according to a similar manner to that of Preparation 33.

(2R)-1-tert-Butoxycarbonyl-2-[(1H-indol-3-yl)methyl] piperazine

IR (KBr): 3410, 3311, 2976, 2924, 1672, 1454, 1417, 1365, 1259 cm$^{-1}$ NMR (DMSO-d$_6$, δ): 1.22 (9H, br s), 2.25–4.20 (10H, m), 6.88–7.70 (5H, m) 10.78 (1H, br s) MASS (APCI): 316 (M+H)$^+$ (3) The following compound was obtained according to a similar manner to that of Preparation 34.

(2R)-1-tert-Butoxycarbonyl-4-[4-(3,3-dimethylmorpholino)-2-butynyl]-2-[(1H-indol-3-yl)methyl]piperazine IR (KBr): 3500–3300, 2972, 2935, 1687, 1456, 1417, 1365, 1333, 1227 cm$^{-1}$ NMR (DMSO-d$_6$, δ): 0.94 (6H, s), 1.21 (9H, s), 1.82–2.20 (2H, m), 2.50–4.30 (17H, m), 6.85–7.66 (5H, m), 10.81 (1H, br s) MASS (APCI): 481 (M+H)$^+$ (4) The following compound was obtained according to a similar manner to that of Preparation 35.

(3R)-1-[4-(3,3-Dimethylmorpholino)-2-butynyl]-3-[(1H-indol-3-yl)methyl]piperazine trihydrochrolide mp: 209–230° C. $[\alpha]_D^{26}$: 10.9° (C=0.5, MeOH) IR (KBr): 3600–3300, 2900, 2700–2400, 1645, 1628, 1539, 1516, 1454, 1429, 1344 cm$^{-1}$ NMR (DMSO-d$_6$, δ): 1.20–1.50 (6H, m), 3.10–4.42 (20H, m), 6.95–7.80 (5H, m), 9.90–10.25 (2H, m), 11.15 (1H, br s), 11.90 (1H, br s) MASS (APCI) 381 (M+H)$^+$ (free)

Preparation 71

(1) Acetic acid (5.4 ml) was added to a solution of 2-amino-2-methyl-1-propanol (8.4 g) and benzaldehyde (10 g) in 1,2-dichloroethane (140 ml) under ice-cooling. After 30 minutes of stirring at the same temperature, sodium triacetoxyborohydride (26 g) was added by small portions to the solution over 10 minutes. After 2 hours of stirring at room temperature, the mixture was poured into a solution of sodium hydrogen carbonate (48 g) in water (300 ml). The aqueous layer was separated and adjusted to pH 12 with 24% sodium hydroxide aqueous solution. The alkaline solution was extracted with ethyl acetate (2 times). The extract was dried over sodium sulfate and evaporated under reduced pressure to give colorless crystals of 2-benzylamino-2-methyl-1-propanol (13.2 g).

mp: 46.0–47.0° C. IR (Nujol): 3330, 3100, 2900, 1450, 1380, 1355 cm$^{-1}$ NMR (DMSO-d$_6$, δ): 0.99 (6H, s), 3.23 (2H, d, J=3.9 Hz), 3.62 (2H, s), 4.50–4.60 (1H, m), 7.16–7.36 (5H, m) MASS (APCI): 180 (M+H)$^+$ (2) 2-Benzylamino-2-methyl-1-propanol (6.0 g) and potassium carbonate (6.95 g) were dissolved in a mixture of dichloromethane (30 ml) and water (30 ml) under ice-cooling. Chloroacetyl chloride (2.95 ml) was added to the mixture over 25 minutes and the whole was stirred for 2 hours at room temperature. The organic layer was separated, washed with diluted hydrochloric acid and brine successively, dried over magnesium sulfate and evaporated under reduced pressure. The residue was dissolved into tert-butyl alcohol (40 ml) and potassium tert-butoxide (3.76 g) was added to the solution. The whole was stirred for 4 hours under reflux under nitrogen atmosphere. After cooling to room temperature, the insoluble mass was filtered off and washed with ethyl acetate. The filtrate and washing were combined and the whole was washed with diluted hydrochloric acid and brine successively, dried over magnesium sulfate and evaporated under reduced pressure. The residue was triturated with a mixture of hexane and diisopropyl ether (1:1) and the resulting crystals were collected by filtration and washed with a mixed solvent of hexane and diisopropyl ether (1:1) to give colorless crystals of 4-benzylamino-5,5-dimethyl-3-morpholinone (4.53 g).

mp: 76–77° C. IR (Nujol): 1635, 1600, 1490, 1460, 1380, 1355 cm$^{-1}$ NMR (CDCl$_3$, δ): 1.20 (6H, s), 3.61 (2H, s), 4.32 (2H, s), 4.64 (2H, s), 7.18–7.36 (5H, m) MASS (APCI): 220 (M+H)$^+$ (3) 4-Benzyl-5,5-dimethyl-3-morpholinone (4.45 g) was added to an ice-cooled suspension of lithium aluminum hydride (0.77 g) in dried tetrahydrofuran (20 ml) under nitrogen atmosphere. After 5 hours of stirring at 50° C., the reaction mixture was cooled below 5° C., and water (0.36 ml), 12% sodium hydroxide aqueous solution (0.36 ml) and water (1 ml) were added thereto successively. After 30 minutes of stirring, the mixture was filtrated through Celite® pad, and the pad was washed with ethyl acetate. The filtrate and washing were combined and the whole was dried over magnesium sulfate, and evaporated under reduced pressure. The residue was purified by column chromatography on silica gel using a mixture of n-hexane and ethyl acetate. The fractions containing the objective compound were collected and evaporated under reduced pressure to give 4-benzyl-3,3-dimethylmorpholine as an oil. The obtained oil and ammonium formate (5.7 g) were dissolved into a mixed solvent of ethanol (35 ml) and water (5 ml), and the whole was stirred under reflux for 1 hour under nitrogen atmosphere. After cooling, the mixture was filtrated through Celite® pad. The filtrate was evaporated under reduced pressure. The residue was dissolved into methanol and 4N hydrogen chloride in ethyl acetate solution was added-thereto. The whole mixture was evaporated and the residue was triturated with a mixture of ethanol and n-hexane (1:1). The resulting crystals were collected by filtration and washed with a mixed solvent of ethanol and n-hexane (1:1) to give colorless crystals of 3,3-dimethylmorpholine hydrochloride (1.56 g).

mp: 196–197° C. IR (Nujol): 3300, 2750, 2650, 2500, 1590, 1460 cm$^{-1}$ NMR (DMSO-d$_6$, δ): 1.21 (6H, s), 3.05–3.11 (2H, m), 3.51 (2H, s), 3.76–3.81 (2H, m), 9.66 (2H, br s)

EXAMPLE 66

Paraformaldehyde (30 mg) and copper(I) iodide (9 mg) were added to a mixture of (2R)-1-[3,5-bis(trifluoromethyl)benzoyl]-2-(3,4-dimethylbenzyl)piperazine (0.16 g), (3S)-3-ethoxycarbonyl-4-(2-propynyl)morpholine (0.08 g) and N,N-diisopropylethylamine (0.09 ml) in 1,4-dioxane (10 ml) and the whole was stirred at room temperature for 30 minutes, and then heated at 90° C. for 30 minutes. After cooling, ethyl acetate and sodium hydrogen carbonate solution were added to the mixture. The organic layer was separated, dried over magnesium sulfate, and evaporated in vacuo. The residue was purified by column chromatography on silica gel with a mixture of ethyl acetate and n-hexane (1:1) as an eluent to give (2R)-1-[3,5-bis(trifluoromethyl)benzoly]-2-(3,4-dimethylbenzyl)-4-[4-((3S)-3-ethoxycarbonylmorpholino)-2-butynyl]piperazine (0.21 g).

NMR (CDCl$_3$, δ): 1.20–5.30 (31H, m), 6.55–7.90 (6H, m) MASS (APCI): 654 (M+H)$^+$

EXAMPLE 67

The following compound was obtained according to a similar manner to that of Example 66.

(2R)-1-[3,5-Bis(trifluoromethyl)benzoyl]-2-(3,4-dimethylbenzyl)-4-[3-[(3R)-(4-tert-butoxycarbonyl)morpholin-3-yl]-2-propynyl]piperazine NMR (DMSO-d$_6$, δ): 1.39 (9H, s), 2.09–2.17 (6H, m), 2.30–5.00 (18H, m), 6.60–8.15 (6H, m) MASS (APCI): 668 (M+H)$^+$ (free)

EXAMPLE 68

To a solution of (2R)-1-[3,5-bis(trifluoromethyl)benzoyl]-2-(3,4-dimethylbenzyl)-4-[3-[(3R)-(4-tert-butoxycarbonyl)morpholin-3-yl]-2-propynyl]piperazine (1.607 g) in ethyl acetate (16 ml) was added hydrogen chloride (4N in ethyl acetate, 3 ml). After 8 hours of stirring at room temperature, the mixture was evaporated under reduced pressure to give (2R)-1-[3,5-bis(trifluoromethyl)benzoyl]-2-(3,4-dimethylbenzyl)-4-[3-[(3R)-morpholin-3-yl]-2-propynyl]piperazine dihydrochloride (1.43 g) as a solid.

mp: 190–191° C. [α]$_D^{27}$: -14.0° (C=0.5, MeOH) IR (KBr): 2927, 1643 cm$^{-1}$ NMR (DMSO-d$_6$, δ): 2.10–2.18 (6H, m), 2.80–5.25 (18H, m), 6.65–8.25 (6H, m) MASS (APCI): 568 (M+H)$^+$ (free)

EXAMPLE 69

Paraformaldehyde (0.034 g) and copper(I) iodide (12 mg) were added to a mixture of (2R)-1-[3,5-bis(trifluoromethyl)benzoyl]-2-(3,4-dimethylbenzyl)-47(2-propynyl)piperazine (0.21 g), (3S)-3-methoxymethylmorpholine (0.09 g) and N,N-diisopropylethylamine (0.1 ml) in 1,4-dioxane (5 ml) and the whole was stirred at room temperature for 30 minutes and then heated at 70° C. for 2.5 hours. After cooling, ethyl acetate and sodium hydrogen carbonate solution were added to the mixture. The organic layer was separated, dried over magnesium sulfate, and evaporated in vacuo. The residue was purified by column chromatography on silica gel with 3% of methanol in chloroform as an eluent to give (2R)-1-[3,5-bis(trifluoromethyl)benzoyl]-2-(3,4-dimethylbenzyl)-4-[4-((3S)-3-methoxymethylmorpholino)-2-butynyl]piperazine. It was dissolved in ethyl acetate and the solution was added 4N hydrogen chloride in ethyl acetate. The mixture was evaporated in vacuo and the residue was triturated with a mixture of ethyl acetate and isopropyl ether to give (2R)-1-[3,5-bis(trifluoromethyl)benzoyl]-2-(3,4-dimethylbenzyl)-4-[4-((3S)-3-methoxymethylmorpholinc)-2-butynyl]piperazine dihydrochloride (0.16 g).

mp: 60–70° C. [α]$_D^{28}$: -1.8° (C=0.25, MeOH) IR (KBr): 1684, 1645, 1512, 1460, 1448, 1431, 1371, 1365, 1325, 1281, 1184, 1136, 1072 cm$^{-1}$ NMR (DMSO-d$_6$, δ): 2.00–2.28 (6H, m), 2.60–5.30 (25H, m), 6.60–8.30 (6H, m) MASS (APCI): 626 (M+H)$^+$ (free)

EXAMPLE 70

The following compounds were obtained according to a similar manner to that of Example 69.
(1) (2R)-1-[3,5-Bis(trifluoromethyl)benzoyl]-2-(3,4-dimethylbenzyl)-4-[4-((3R)-3-fluoromethylmorpholino)-2-butynyl]piperazine dihydrochloride
mp: 118–128° C. [α]$_D^{28}$: -6.8° (C=0.25, MeOH). IR (KBr): 1645, 1502, 1435, 1365, 1321, 1282, 1182, 1136, 1049 cm$^{-1}$ NMR (DMSO-d$_6$, δ): 2.00–2.30 (6H, m), 2.60–5.30 (22H, m), 6.60–8.30 (6H, m) MASS (APCI) 614 (M+H)$^+$ (free)

(2) (2R)-1-[3,5-Bis(trifluoromethyl)benzoyl]-2-(3,4-dimethylbenzyl)-4-[4-(tetrahydro-6-fluoro-1,4-oxazepin-4(5H)-yl)-2-butynyl]piperazine dihydrochloride mp: 90–100° C. $[\alpha]_D^{28}$: +1.6° (C=0.25, MeOH) IR (KBr): 1645, 1504, 1433, 1373, 1365, 1323, 1282, 1219, 1182, 1136 cm$^{-1}$ NMR (DMSO-d$_6$, δ): 2.00–2.30 (6H, m), 2.60–5.30 (22H, m), 6.60–8.28 (6H, m) MASS (APCI): 614 (M+H)$^+$ (free)

EXAMPLE 71

The following compounds were obtained according to a similar manner to that of Example 31.

(1) (2R)-1-[3,5-Bis(trifluoromethyl)benzoyl]-2-(3,4-dimethylbenzyl)-4-[4-(3-methoxymethyl-3-methylmorpholino)-2-butynyl]piperazine dihydrochloride mp: 155–160° C. $[\alpha]_D^{25}$: −11.6° (C=0.25, MeOH) IR (KBr): 1645, 1437, 1362, 1323, 1281, 1219, 1182, 1138, 1055 cm$^{-1}$ NMR (DMSO-d$_6$, δ): 1.20–1.50 (3H, m), 2.05–2.26 (6H, m), 2.60–5.20 (24H, m), 6.60–8.30 (6H, m) MASS (APCI): 640 (M+H)$^+$ (free)

(2) (2R)-1-[3,5-Bis(trifluoromethyl)benzoyl]-2-(3,4-dimethylbenzyl)-4-[4-((3S)-3-ethoxymethylmorpholino)-2-butynyl]piperazine dihydrochloride mp: 155–160° C. $[\alpha]_D^{25}$: +0.6° (C=0.25, MeOH) IR (KBr): 1645, 1439, 1371, 1281, 1217, 1182, 1136, 1072, 1032 cm$^{-1}$ NMR (DMSO-d$_6$, δ): 1.13 (3H, t, J=7.0 Hz), 2.02–5.24 (30H, m), 6.60–8.28 (6H, m) MASS (APCI) 640 (M+H)$^+$ (free)

(3) (2R)-1-[3,5-Bis(trifluoromethyl)benzoyl]-2-(3,4-dimethylbenzyl)-4-[4-((3S,5S)-3,5-dimethylmorpholino)-2-butynyl]piperazine dihydrochloride mp: 160–165° C. $[\alpha]_D^{26}$: +14.2° (C=0.25, MeOH) IR (KBr): 1657, 1649, 1643, 1433, 1356, 1281, 1186, 1136, 1109 cm$^{-1}$ NMR (DMSO-d$_6$, δ): 1.10–1.45 (6H, m), 2.00–2.28 (6H, m), 2.60–5.20 (19H, m), 6.60–8.28 (6H, m) MASS (APCI): 610 (M+H)$^+$ (free)

(4) (2R)-1-[3,5-Bis(trifluoromethyl)benzoyl]-2-(3,4-dimethylbenzyl)-4-[4-((3S)-3-hydroxymethylmorpholino)-2-butynyl]piperazine dihydrochloride mp: 130–150° C. $[\alpha]_D^{28}$: −2.6° (C=0.25, MeOH) IR (KBr): 1691, 1645, 1512, 1458, 1442, 1433, 1371, 1365, 1325, 1281, 1217, 1182, 1136, 1059 cm$^{-1}$ NMR (DMSO-d$_6$, δ): 2.00–2.30 (6H, m), 2.60–5.30 (22H, m), 6.60–8.28 (6H, m) MASS (APCI) 612 (M+H)$^+$ (free)

(5) (2R)-1-[3,5-Bis(trifluoromethyl)benzoyl]-2-(3,4-dimethylbenzyl)-4-[4-((2S)-2-methoxymethylmorpholino)-2-butynyl]piperazine dihydrochloride mp: 85–95° C. $[\alpha]_D^{25}$: −4.71° (C=0.255, MeOH) IR (KBr): 1641, 1631, 1442, 1281, 1134 cm$^{-1}$ NMR (DMSO-d$_6$, δ): 2.00–2.30 (6H, m), 2.60–5.28 (25H, m), 6.60–8.30 (6H, m) MASS (APCI): 626 (M+H)$^+$ (free)

(6) (2R)-1-[3,5-Bis(trifluoromethyl)benzoyl]-2-(3,4-dimethylbenzyl)-4-[4-((2R)-2-methoxymethylmorpholino)-2-butynyl]piperazine dihydrochloride mp: 80–90° C. $[\alpha]_D^{25}$: −15.00° (C=0.24, MeOH) IR (KBr): 1657, 1649, 1641, 1631, 1441, 1431, 1281, 1186, 1176, 1136, 1109 cm$^{-1}$ NMR (DMSO-d$_6$, δ): 2.00–2.30 (6H, m), 2.60–5.20 (25H, m), 6.60–8.30 (6H, m) MASS (APCI): 626 (M+H)$^+$ (free)

(7) (2R)-1-[3,5-Bis(trifluoromethyl)benzoyl]-2-(3,4-dimethylbenzyl)-4-[(E)-4-((3R)-3-methoxymethylmorpholino)-2-butenyl]piperazine dihydrochloride mp: 240–250° C. $[\alpha]_D^{28}$: −19.47° (C=0.19, MeOH) IR (KBr): 1647, 1635, 1618, 1456, 1435, 1379, 1281, 1186, 1132, 1108 cm$^{-1}$ NMR (DMSO-d$_6$, δ): 2.00–2.28 (6H, m), 2.60–5.20 (25H, m), 5.80–8.30 (8H, m) MASS (APCI): 628 (M+H)$^+$ (free)

EXAMPLE 72

A mixture of (2R)-1-[3,5-bis(trifluoromethyl)benzoyl]-2-(3,4-dimethylbenzyl)-4-[4-chloro-2-butynyl]piperazine (1.2 g) and (3S)-3-ethoxycarbonylmorpholine hydrochloride (0.43 g), potassium carbonate (1.09 g) and a trace of potassium iodide in N,N-dimethylformamide (50 ml) was stirred at 55° C. for 12 hours. After cooling, the solvent was removed by evaporation, and ethyl acetate and water were added thereto. The organic layer was separated, dried over magnesium sulfate, and evaporated in vacuo. The residue was purified by column chromatography on silica gel with a mixture of ethyl acetate and n-hexane (2:3) as an eluent to give (2R)-1-[3,5-bis(trifluoromethyl)benzoyl]-2-(3,4-dimethylbenzyl)-4-[4-((3S)-3-ethoxycarbonylmorpholino)-2-butynyl]piperazine (0.29 g) as an oil.

NMR (CDCl$_3$, δ): 1.20–5.30 (31H, m), 6.55–7.90 (6H, m) MASS (APCI): 654 (M+H)$^+$

EXAMPLE 73

The following compounds were obtained according to a similar manner to that of Example 72.

(1) (2R)-1-[3,5-Bis(trifluoromethyl)benzoyl]-2-(3,4-dimethylbenzyl)-4-[4-((3R)-3-ethylmorpholino)-2-butynyl]piperazine dihydrochloride $[\alpha]_D^{27}$: −22.7° (C=0.5, MeOH) IR (KBr): 3600, 1645, 1460, 1280, 1180, 1135 cm$^{-1}$ NMR (DMSO-d$_6$, δ): 0.83–5.17 (31H, m), 6.62–8.24 (6H, m) MASS (APCI): 610 (M+H)$^+$ (free)

(2) (2R)-1-[3,5-Bis(trifluoromethyl)benzoyl]-4-[4-((3S)-3-ethylmorpholino)-2-butynyl]-2-[(1H-indol-3-yl)methyl]piperazine dihydrochloride $[\alpha]_D^{28}$: +11.2° (C=0.5, MeOH) IR (KBr): 3365, 2600, 1645, 1430, 1280, 1180, 1135 cm$^{-1}$ NMR (DMSO-d$_6$, δ): 0.67–5.20 (25H, m), 6.60–8.28 (8H, m), 10.96 (1H, s) MASS (APCI): 621 (M+H)$^+$ (free)

(3) (2R)-1-[3,5-Bis(trifluoromethyl)benzoyl]-2-(3,4-dimethylbenzyl)-4-[(E)-4-((3S)-3-methoxymethylmorpholino)-2-butenyl]piperazine dihydrochloride mp: 130–140° C. $[\alpha]_D^{27}$: +2.0° (C=0.25, MeOH) IR (KBr): 1653, 1647, 1637, 1282, 1188, 1134 cm$^{-1}$ NMR (DMSO-d$_6$, δ): 2.00–2.28 (6H, m), 2.70–5.28 (25H, m), 6.00–8.32 (8H, m) MASS (APCI): 628 (M+H)$^+$ (free)

EXAMPLE 74

A solution of (2R)-1-[3,5-bis(trifluoromethyl)benzoyl]-2-(3,4-dimethylbenzyl)-4-[4-((3S)-3-ethoxycarbonylmorpholino)-2-butynyl]piperazine (0.42 g) in ethanol (30 ml) was added 1N sodium hydroxide solution (30 ml) and the whole was stirred at room temperature for 2 hours. The solvent was removed under reduced pressure and the residual aqueous solution was neutralized with conc. hydrochloric acid. The solution was extracted with dichloromethane. The extract was dried over magnesium sulfate and evaporated in vacuo to give (2R)-1-[3,5-bis(trifluoromethyl)benzoyl]-2-(3,4-dimethylbenzyl)-4-[((3S)-3-carboxymorpholino)-2-butynyl]piperazine (0.26 g) as an oil.

NMR (CDCl$_6$, δ): 2.00–5.28 (26H, m), 6.50–7.90 (6H, m) MASS (APCI): 626 (M+H)$^+$

EXAMPLE 75

A tetrahydrofuran solution of dimethylamine (2 M, 0.32 ml) was added to a mixture of (2R)-1-[3,5-bis(trifluoromethyl)benzoyl]-2-(3,4-dimethylbenzyl)-4-[4-

((3S)-3-carboxymorpholino)-2-butynyl]piperazine (0.13 g), 1-hydroxybenzotriazole (85 mg) and 1-(3-dimethylaminopropyl)-3-ethylcarbodiimide hydrochloride (0.12 g) in N,N-dimethylformamide (5 ml), and the whole was stirred at room temperature for 5 hours. After the solvent was removed by evaporation, dichloromethane and sodium hydrogen carbonate solution were added to the residue. The organic layer was separated, dried over magnesium sulfate, and evaporated in vacuo. The residue was purified by column chromatography on silica gel with 3% of methanol in dichloromethane as an eluent to give (2R)-1-[3,5-bis(trifluoromethyl)benzoyl]-2-(3,4-dimethylbenzyl)-4-[4-((3S)-3-dimethylcarbamoylmorpholino)-2-butynyl]piperazine. It was dissolved in ethyl acetate (10 ml) and the solution was added 4N hydrogen chloride in ethyl acetate (0.26 ml). The mixture was evaporated in vacuo and the residue was triturated with a mixture of ethyl acetate and isopropyl ether to give (2R)-1-[3,5-bis(trifluoromethyl)benzoyl]-2-(3,4-dimethylbenzyl)-4-[4-((3S)-3-dimethylcarbamoylmorpholino)-2-butynyl]piperazine dihydrochloride (0.12 g) as a solid.

mp: 150–160° C. $[\alpha]_D^{27}$: −33.2° (C=0.25, MeOH) IR (KBr): 1653, 1506, 1433, 1371, 1325, 1281, 1182, 1136, 1063, 1026 cm$^{-1}$ NMR (DMSO-d$_6$, δ): 2.00–2.30 (6H, m), 2.60–5.20 (26H, m), 6.60–8.30 (6H, m) MASS (APCI): 653 (M+H)$^+$ (free)

EXAMPLE 76

The following compounds were obtained according to a similar manner to that of Example 5.
(1) (2R)-1-[3,5-Bis(trifluoromethyl)benzoyl]-2-[(1H-indol-3-yl)methyl]-4-{3-[2-(4-methoxy)pyridyl]-2-propynyl}piperazine dihydrochloride mp: 130–135° C. $[\alpha]_D^{28}$: +2.8° (C=0.5, MeOH) IR (KBr): 3600, 3314, 1640, 1625, 1430, 1280, 1180, 1135 cm$^{-1}$ NMR (DMSO-d$_6$, δ): 3.95 (3H, s), 2.74–5.24 (11H, m), 6.60–8.60 (11H, m), 10.92 (1H, s) MASS (APCI): 601 (M+H)$^+$ (free)
(2) (2R)-1-[3,5-Bis(trifluoromethyl)benzoyl]-2-(3,4-dimethylbenzyl)-4-{3-[2-(4-methoxy)pyridyl]-2-propynyl}piperazine dihydrochloride mp: 95–100° C. $[\alpha]_D^{28}$: −6.2° (C=0.5, MeOH) IR (KBr): 3405, 2930, 2590, 1625, 1430, 1280, 1180, 1135 cm$^{-1}$ NMR (DMSO-d$_6$, δ): 2.51 (3H, s), 2.03–5.20 (17H, m), 6.66–8.66 (9H, m) MASS (APCI): 590 (M+H)$^+$ (free)
(3) (2R)-1-[3,5-Bis(trifluoromethyl)benzoyl]-2-[(1H-indol-3-yl)methyl]-4-{3-[2-(4-methyl)pyridyl]-2-propynyl}piperazine dihydrochloride mp: 150–155° C. $[\alpha]_D^{27}$: −3.3° (C=0.5, MeOH) IR (KBr): 3335, 1645, 1498, 1430, 1280, 1185 cm$^{-1}$ NMR (DMSO-d$_6$, δ): 2.37 (3H, s), 2.10–5.24 (11H, m), 6.60–8.67 (11H, m), 10.93 (1H, s) MASS (APCI): 585 (M+H)$^+$ (free)
(4) (2R)-1-[3,5-Bis(trifluoromethyl)benzoyl]-2-(3,4-dimethylbenzyl)-4-{3-[2-(4-methoxycarbonyl)pyridyl]-2-propynyl}piperazine dihydrochloride mp: 125–130° C. $[\alpha]_D^{28}$: −30.3° (C=0.5, MeOH) IR (KBr): 2600, 1740, 1645, 1430, 1280, 1180 cm$^{-1}$ NMR (DMSO-d$_6$, δ): 3.93 (3H, s), 2.00–5.20 (17H, m), 6.60–8.90 *(9H, m) MASS (APCI): 618 (M+H)$^+$ (free)

EXAMPLE 77

A mixture of (2R)-1-[3,5-bis(trifluoromethyl)benzoyl]-2-[(1H-indol-3-yl)methyl]piperazine (0.20 g), (3S, 5S)-3,5-dimethyl-4-(4-chloro-2-butynyl)morpholine (0.11 g) and potassium carbonate (0.31 g) in N,N-dimethylformamide (4 ml) was stirred at 60° C. for 3 hours. After cooling, the solvent was removed under reduced pressure and the residue was partitioned between ethyl acetate and sodium hydrogen carbonate solution. The organic layer was separated, dried over magnesium sulfate, and evaporated in vacuo. The residue was purified by column chromatography on silica gel with 3% of methanol in ethyl acetate as an eluent to give (2R)-1-[3,5-bis(trifluoromethyl)benzoyl]-4-[4-((3S,5S)-3,5-dimethylmorpholino)-2-butynyl]-2-[(1H-indol-3-yl)methyl]piperazine. It was dissolved in ethyl acetate and the solution was added 4N hydrogen chloride in ethyl acetate. The mixture was evaporated in vacuo and the residue was triturated with isopropyl ether to give (2R)-1-[3,5-bis-trifluoromethyl)benzoyl]-4-[4-((3S,5S)-3,5-dimethylmorpholino)-2-butynyl]-2-[(1H-indol-3-yl)methyl]piperazine dihydrochloride (0.11 g).

mp: 170–180° C. $[\alpha]_D^{27}$: +21.57° (C=0.255, MeOH) IR (KBr): 1645, 1637, 1458, 1431, 1360, 1281, 1184, 1136, 1111 cm$^{-1}$ NMR (DMSO-d$_6$, δ): 1.10–1.45 (6H, m), 2.70–5.30 (19H, m), 6.60–8.28 (8H, m) MASS (APCI): 621 (M+H)$^+$ (free)

EXAMPLE 78

The following compounds were obtained according to a similar manner to that of Example 77.
(1) (2R)-1-[3,5-Bis(trifluoromethyl)benzoyl]-4-[4-((3R)-3-ethylmorpholino)-2-butynyl]-2-[(1H-indol-3-yl)methyl]piperazine dihydrochloride mp: 176–180° C. $[\alpha]_D^{26}$: −12.2° (C=0.25, MeOH) IR (KBr): 1635, 1454, 1437, 1358, 1333, 1281, 1223, 1182, 1138, 1068 cm$^{-1}$ NMR (DMSO-d$_6$, δ): 0.68–5.30 (25H, m), 6.55–8.30 (8H, m), 10.95 (1H, s) MASS (APCI): 621 (M+H)$^+$ (free)
(2) (2R)-1-[3,5-Bis(trifluoromethyl)benzoyl]-4-[3-(3,3-dimethylmorpholino)propyl]-2-[(1H-indol-3-yl)methyl]piperazine dihydrochloride mp: 107~° C. $[\alpha]_D^{27}$: −7.0° (C=0.5, MeOH) IR (KBr): 3500–3400, 2933, 2599, 1645, 1637, 1458, 1435, 1362, 1280 cm$^{-1}$ NMR (DMSO-d$_6$, δ) 1.2–1.4 (6H, m), 2.1–1.6 (2H, m), 2.7–5.2 (19H, m), 6.6–8.3 (8H, m), 10.9–11.8 (3H, m) MASS (APCI): 611 (M+H)$^+$ (free)
(3) (2R)-1-[3,5-Bis(trifluoromethyl)benzoyl]-2-(3,4-dimethylbenzyl)-4-{2-[7-oxa-4-azaspiro[2.5]octan-4-yl]ethyl}}piperazine dihydrochloride mp: 110–113° C. $[\alpha]_D^{28}$: −13.8° (C=0.5, MeOH) IR (KBr): 3435, 1645 cm$^{-1}$ NMR (DMSO-d$_6$, δ): 0.80–0.95 (2H, m), 1.20–1.50 (2H, m), 2.11–2.19 (6H, m), 3.00–5.15 (19H, m), 6.65–8.17 (6H, m) MASS (APCI): 584 (M+H)$^+$ (free)
(4) (2R)-1-[3,5-Bis(trifluoromethyl)benzoyl]-2-(3,4-dimethylbenzyl)-4-[3-(3,3-dimethylmorpholino)propyl]piperazine dihydrochloride mp: 197° C. $[\alpha]_D^{27}$: −17.8° (C=0.5, MeOH) IR (KBr): 3500–3400, 2933, 2692, 1645, 1637, 1456, 1430, 1435, 1280, cm$^{-1}$ NMR (DMSO-d$_6$, δ): 1.33 (6H, s), 1.92–5.2 (27H, m), 6.6–8.3 (6H, m), 11.0–11.5 (2H, m) MASS (APCI): 600 (M+H)$^+$ (free)

EXAMPLE 79

The following compounds were obtained according to a similar manner to that of Example 5.
(1) (2R)-1-[3,5-Bis(trifluoromethyl)benzoyl]-4-[2-(3,3-dimethylmorpholino)ethyl]-2-[(1H-indol-3-yl)methyl]piperazine dihydrochloride mp: 247–258° C. $[\alpha]_D^{27}$: −4.5° (C=0.5, MeOH) IR (KBr): 3500–3400, 1645, 1637, 1280 cm$^{-1}$ NMR (DMSO-d$_6$, δ): 1.2–1.5 (6H, m), 2.8–5.3 (19H, m), 6.6–8.3 (8H, m), 11.0 (1H, br s), 11.5–12.1 (2H, m) MASS (APCI): 597 (M+H)$^+$ (free)

(2) (2R)-1-[3,5-Bis(trifluoromethyl)benzoyl]-2-(3,4-dimethylbenzyl)-4-[2-(3,3-dimethylmorpholino)ethyl]piperazine dihydrochloride mp: 190–210° C. $[\alpha]_D^{27}$: −13.9° (C=0.5, MeOH) IR (KBr): 3500–3400, 1643, 1450, 1430, 1384, 1363, 1280, 1185 cm$^{-1}$ NMR (DMSO-d$_6$, δ): 1.40 (6H, s), 2.10–2.2 (6H, m), 2.7–5.2 (19H, m), 6.6–8.2 (6H, m), 11.6–12.2 (2H, m) MASS (APCI): 586 (M+H)$^+$ (free)

EXAMPLE 80

The following compounds were obtained according to a similar manner to that of Example 39.

(1) (2R)-1-[3,5-Bis(trifluoromethyl)benzoyl]-2-(3,4-dimethylbenzyl)-4-[2-((3R)-3-ethylmorpholino)ethyl]piperazine dihydrochloride $[\alpha]_D^{28}$: −23.6° (C=0.5, MeOH) IR (KBr): 3425, 2600, 1645, 1640, 1280, 1185, 1135 cm$^{-1}$ NMR (DMSO-d$_6$, δ): 0.95 (3H, t, J=7.2 Hz), 1.57–5.20 (28H, m), 6.66–8.28 (6H, m) MASS (APCI): 586 (M+H)$^+$ (free)

(2) (2R)-1-[3,5-Bis(trifluoromethyl)benzoyl]-2-(3,4-dimethylbenzyl)-4-[2-((3S)-3-hydroxymethylmorpholino)ethyl]piperazine dihydrochloride mp: 150–160° C. $[\alpha]_D^{26}$: −8.4° (C=0.25, MeOH) IR (KBr): 1643, 1437, 1375, 1323, 1282, 1221, 1184, 1138, 1047 cm$^{-1}$ NMR (DMSO-d$_6$, δ): 2.00–2.28 (6H, m), 2.60–5.20 (23H, m), 6.58–8.28 (6H, m) MASS (APCI): 588 (M+H)$^+$ (free)

(3) (2R)-1-[3,5-Bis(trifluoromethyl)benzoyl]-2-(3,4-dimethylbenzyl)-4-[2-((2S)-2-methoxyrmethylmorpholino)ethyl]piperazine dihydrochloride mp: 180–190° C. $[\alpha]_D^{26}$: −12.36° (C=0.275, MeOH) IR (KBr): 1653, 1647, 1635, 1282, 1182, 1136 cm$^{-1}$ NMR (DMSO-d$_6$, δ): 2.00–5.20 (31H, m), 6.60–8.30 (6H, m) MASS (APCI): 602 (M+H)$^+$ (free)

(4) (2R)-1-[3,5-Bis(trifluoromethyl)benzoyl]-2-(3,4-dimethylbenzyl)-4-[2-((3S)-3-methoxymethylmorpholino)ethyl]piperazine dihydrochloride mp: 90–100° C. $[\alpha]_D^{27}$: −9.8° (C=0.25, MeOH) IR (KBr): 1645, 1512, 1506, 1460, 1433, 1371, 1325, 1282, 1223, 1184, 1136, 1053 cm$^{-1}$ NMR (DMSO-d$_6$, δ): 2.00–2.30 (6H, m), 2.60–5.20 (25H, m), 6.60–8.40 (6H, m) MASS (APCI): 602 (M+H)$^+$ (free)

(5) (2R)-1-[3,5-Bis(trifluoromethyl)benzoyl]-2-(3,4-dimethylbenzyl)-4-[2-(2-methoxymethylmorpholino)ethyl]piperazine dihydrochloride mp: 150–154° C. $[\alpha]_D^{28}$: −5.8° (C=0.5, MeOH) IR (KBr): 3463–3406, 1647 cm$^{-1}$ NMR (DMSO-d$_6$, δ): 2.10–2.18 (6H, m), 2.40–5.10 (25H, m), 6.55–8.16 (6H, m) MASS (APCI): 602 (M+H)$^+$ (free)

(6) (2R)-1-[3,5-Bis(trifluoromethyl)benzoyl]-2-(3,4-dimethylbenzyl)-4-[3-((3S)-3-methoxymethylmorpholino)propyl]piperazine dihydrochloride mp: 55–60° C. $[\alpha]_D^{27}$: −1.4° (C=0.25, MeOH) IR (KBr): 1653, 1647, 1635, 1282, 1182, 1134, 1109 cm$^{-1}$ NMR (DMSO-d$_6$, δ): 1.80–5.22 (33H, m), 6.60–8.30 (6H, m) MASS (APCI): 616 (M+H)$^+$ (free)

(7) (2R)-1-[3,5-Bis(trifluoromethyl)benzoyl]-2-(3,4-dimethylbenzyl)-4-[3-(2-methoxymethylmorpholino)propyl]piperazine hydrochloride mp: 145–155° C. $[\alpha]_D^{28}$: −11.9° (C=0.5, MeOH) IR (KBr): 3455–3407, 1645 cm$^{-1}$ NMR (DMSO-d$_6$, δ): 2.10–2.19 (6H, m), 2.10–5.10 (27H, m), 6.68–8.17 (6H, m) MASS (APCI): 616 (M+H)$^+$ (free)

(8) (2R)-1-[3,5-Bis(trifluoromethyl)benzoyl]-2-[(1H-indol-3-yl)methyl]-4-[2-((3S)-3-methoxymethylmorpholino)ethyl]piperazine dihydrochloride mp: 175–185° C. $[\alpha]_D^{27}$: −0.6° (C=0.25, MeOH) IR (KBr): 1645, 1637, 1458, 1431, 1383, 1362, 1281, 1184, 1138, 1111 cm$^{-1}$ NMR (DMSO-d$_6$, δ): 2.80–5.28 (25H, m), 6.60–8.30 (8H, m) MASS (APCI): 613 (M+H)$^+$ (free)

(9) (2R)-1-[3,5-Bis(trifluoromethyl)benzoyl]-2-[(1H-indol-3-yl)methyl]-4-[2-((3R)-3-methoxymethylmorpholino)ethyl]piperazine dihydrochloride mp: 130–150° C. $[\alpha]_D^{26}$: −15.8° (C=0.25, MeOH) IR (KBr): 1653, 1645, 1635, 1281 cm$^{-1}$ NMR (DMSO-d$_6$, δ): 2.60–5.25 (25H, m), 6.60–8.32 (8H, m), 10.96 (1H, s) MASS (APCI): 613 (M+H)$^+$ (free)

(10) (2R)-1-[3,5-Bis(trifluoromethyl)benzoyl]-2-(3,4-dimethylbenzyl)-4-[3-((3R)-3-methoxymethylmorpholino)propyl]piperazine dihydrochloride mp: 80–100° C. $[\alpha]_D^{28}$: −21.59° (C=0.22, MeOH) IR (KBr): 1653, 1647, 1637, 1618, 1508, 1473, 1464, 1456, 1448, 1435, 1431, 1385, 1373, 1363, 1281, 1215, 1184, 1136, 1109 cm$^{-1}$ NMR (DMSO-d$_6$, δ): 2.00–5.40 (33H, m), 6.55–8.30 (6H, m) MASS (APCI): 616 (M+H)$^+$ (free)

EXAMPLE 81

The following compounds were obtained according to a similar manner to that of Example 37.

(1) (2R)-1-[3,5-Bis(trifluoromethyl)benzoyl]-2-(3,4-dimethylbenzyl)-4-[2-((3R)-3-fluoromethylmorpholino)ethyl]piperazine dihydrochloride mp: 145–155° C. $[\alpha]_D^{26}$: −19.2° (C=0.25, MeOH) IR (KBr): 1643, 1437, 1367, 1321, 1281, 1221, 1184, 1138, 1034 cm$^{-1}$ NMR (DMSO-d$_6$, δ): 2.00–2.28 (6H, m), 2.60–5.20 (22H, m), 6.60–8.32 (6H, m) MASS (APCI): 590 (M+H)$^+$ (free)

(2) (2R)-1-[3,5-Bis(trifluoromethyl)benzoyl]-2-(3,4-dimethylbenzyl)-4-[2-(3-methoxymethyl-3-methylmorpholino)ethyl]piperazine dihydrochloride mp: 60–70° C. $[\alpha]_D^{27}$: −15.5° (C=0.3, MeOH) IR (KBr): 1643, 1469, 1439, 1375, 1369, 1360, 1323, 1282, 1225, 1184, 1138 cm$^{-1}$ NMR (DMSO-d$_6$, δ): 1.10–1.50 (3H, s), 2.00–5.22 (30H, m), 6.60–8.30 (6H, m) MASS (APCI): 616 (M+H)$^+$ (free)

(3) (2R)-1-[3,5-Bis(trifluoromethyl)benzoyl]-2-(3,4-dimethylbenzyl)-4-[2-((3S)-3-ethoxymethylmorpholino)ethyl]piperazine dihydrochloride mp: 60–65° C. $[\alpha]_D^{27}$: −8.2° (C=0.25, MeOH) IR (KBr): 1643, 1437, 1369, 1321, 1281, 1221, 1182, 1138, 1072, 1051 cm$^{-1}$ NMR (DMSO-d$_6$, δ): 1.10–1.30 (3H, m), 2.00–5.25 (30H, m), 6.60–8.40 (6H, m) MASS (APCI): 616 (M+H)$^+$ (free)

(4) (2R)-1-[3,5-Bis(trifluoromethyl)benzoyl]-2-(3,4-dimethylbenzyl)-4-[2-((3R)-3-methoxymethylmorpholino)ethyl]piperazine dihydrochloride mp: 90–100° C. $[\alpha]_D^{27}$: −26.48° (C=0.287, MeOH) IR (KBr): 1635, 1469, 1454, 1437, 1375, 1369, 1360, 1321, 1282, 1221, 1184, 1136, 1074 cm$^{-1}$ NMR (DMSO-d$_6$, δ): 2.00–5.22 (31H, m), 6.60–8.28 (6H, m) MASS (APCI): 602 (M+H)$^+$ (free)

(5) (2R)-1-[3,5-Bis(trifluoromethyl)benzoyl]-2-(3,4-dimethylbenzyl)-4-[2-((2R)-2-methoxymethylmorpholino)ethyl]piperazine dihydrochloride mp: 160–170° C. $[\alpha]_D^{27}$: −17.40° (C=0.27, MeOH) IR (KBr): 1645, 1454, 1431, 1383, 1363, 1321, 1281, 1215, 1184, 1138, 1109 cm$^{-1}$ NMR (DMSO-d$_6$, δ): 2.00–2.28 (6H, m), 2.60–5.22 (25H, m), 6.60–8.28 (6H, m) MASS (APCI): 602 (M+H)$^+$ (free)

(6) (2R)-1-[3,5-Bis(trifluoromethyl)benzoyl]-2-(2-naphthylmethyl)-4-[2-((3S)-3-ethylmorpholino)ethyl]piperazine dihydrochloride $[\alpha]_D^{28}$: −16.2° (C=0.5, MeOH) IR (KBr): 3400, 2610, 1430, 1280, 1185, 1135 cm$^{-1}$ NMR (DMSO-d$_6$, δ): 0.86–5.31 (25H, m), 7.00–8.20 (10H, m) MASS (APCI): 608 (M+H)$^+$ (free)

(7) (2R)-1-[3,5-Bis(trifluoromethyl)benzoyl]-2-[(1H-indol-3-yl)methyl]-4-[2-((2S)-2-methoxympethylmorpholino)ethyl]piperazine dihydrochloride mp: 160–170° C. $[\alpha]_D^{27}$: −3.0° (C=0.25, MeOH) IR (KBr): 1645, 1637, 1618, 1458, 1429, 1362, 1281, 1184, 1138, 1109, 1099 cm$^{-1}$ NMR (DMSO-d$_6$, δ): 2.60–5.30 (25H, m), 6.60–8.30 (8H, m) MASS (APCI): 613 (M+H)$^+$ (free)

(8) (2R)-1-[3,5-Bis(trifluoromethyl)benzoyl]-2-[(1H-indol-3-yl)methyl]-4-[2-((2R)-2-methoxymethylmorpholino)ethyl]piperazine dihydrochloride mp: 190–200° C. $[\alpha]_D^{27}$: −15.0° (C=0.24, MeOH) IR (KBr): 1641, 1458, 1421, 1362, 1282, 1176, 1130, 1113, 1099, 1074 cm$^{-1}$ NMR (DMSO-d$_6$, δ) 2.60–5.28 (25H, m), 6.60–8.28 (8H, m), 10.94 (1H, s) MASS (APCI): 613 (M+H)$^+$ (free)

(9) (2R)-1-[3,5-Bis(trifluoromethyl)benzoyl]-2-[(1H-indol-3-yl)methyl]-4-[2-((3S, 5S)-3,5-dimethylmorpholino)ethyl]piperazine dihydrochloride mp: 170–180° C. $[\alpha]_D^{27}$: +13.49° (C=0.315, MeOH) IR (KBr): 1645, 1637, 1458, 1448, 1429, 1362, 1281, 1184, 1136, 1111 cm$^{-1}$ NMR (DMSO-d$_6$, δ) 1.08–1.50 (6H, m), 2.60–5.20 (19H, m), 6.55–8.30 (8H, m) MASS (APCI): 597 (M+H)$^+$ (free)

(10) (2R)-1-[3,5-Bis(trifluoromethyl)benzoyl]-4-[2-((3R)-3-ethylmorpholino)ethyl]-2-[(1H-indol-3-yl)methyl]piperazine dihydrochloride $[\alpha]_D^{28}$: −14.9° (C=0.5, MeOH) IR (KBr): 3365, 2590, 2470, 1645, 1430, 1280, 1185, 1140 cm$^{-1}$ NMR (DMSO-d$_6$, δ): 1.53–5.20 (25H, m), 6.60–8.28 (8H, m), 10.95 (1H, s) MASS (APCI): 597 (M+H)$^+$ (free)

(11) (2R)-1-[3,5-Bis(trifluoromethyl)benzoyl]-4-[2-((3S)-3-ethylmorpholino)ethyl]-2-[(1H-indol-3-yl)methyl]piperazine dihydrochloride $[\alpha]_D^{28}$: +6.0° (C=0.5, MeOH) IR (KBr): 3300, 2670, 2610, 1645, 1430, 1280, 1180, 1140 cm$^{-1}$ NMR (DMSO-d$_6$, δ): 0.84–5.20 (25H, m), 6.64–8.28 (8H, m), 10.94 (1H, s) MASS (APCI): 597 (M+H)$^+$ (free)

EXAMPLE 82

A solution of (2R)-1-[3,5-bis(trifluoromethyl)benzoyl]-2-(3,4-dimethylbenzyl)-4-[4-((3S)-3-methoxymethylmorpholino)-2-butynyl]piperazine (0.09 g) in methanol (10 ml) was hydrogenated in the presence of 10% palladium-carbon (40 mg) at room temperature. After 1 hour, palladium-carbon was removed by filtration and the filtrate was evaporated under reduced pressure. The residue was purified by column chromatography on silica gel with a mixture of methanol and ethyl acetate as an eluent to give (2R)-1-[3,5-bis-(trifluoromethyl)benzoyl]-2-(3,4-dimethylbenzyl)-4-[4-((3S)-3-methoxymethylmorpholino)butyl]piperazine. It was dissolved in ethyl acetate (10 ml) and 4N hydrogen chloride in ethyl acetate (0.5 ml) was added thereto. The mixture was evaporated in vacuo and the residue was triturated with a mixture of ethyl acetate and isopropyl ether to give (2R)-1-[3,5-bis(trifluoromethyl)benzoyl]-2-(3,4-dimethylbenzyl)-4-[4-((3S)-3-methoxymethylmorpholino)butyl]piperazine dihydrochloride (0.03 g) as a solid.

NMR (DMSO-d$_6$, δ): 1.60–2.00 (4H, m), 2.00–2.30 (6H, m), 2.60–5.20 (25H, m), 6.60–8.30 (6H, m), 10.40–11.60 (2H, m) MASS (APCI): 630 (M+H)$^+$ (free)

EXAMPLE 83

The following compounds were obtained according to a similar manner to that of Example 82.

(1) (2R)-1-[3,5-Bis(trifluoromethbyl)benzoyl]-2-(3,4-dimethylbenzyl)-4-{3-[2-(4-methoxy)pyridyl]propyl}piperazine dihydrochloride mp: 130–140° C. $[\alpha]_D^{28}$: −10.4° (C=0.5, MeOH) IR (KBr): 3425, 2400, 1640, 1500, 1430, 1280, 1180, 1135 cm$^{-1}$ NMR (DMSO-d$_6$, δ): 4.08 (3H, s), 2.05–5.14 (21H, m), 6.60–8.72 (9H, m) MASS (APCI): 594 (M+H)$^+$ (free)

(2) (2R)-1-[3,5-Bis(trifluoromethyl)benzoyl]-2-[(1H-indol-3-yl)methyl]-4-{3-[2-(4-methyl)pyridyl]propyl}piperazine dihydrochloride mp: 120–130° C. $[\alpha]_D^{27}$: −5.0° (C=0.5, MeOH) IR (KBr): 3420, 1645, 1498, 1430, 1280, 1135 cm$^{-1}$ NMR (DMSO-d$_6$, δ): 2.55 (3H, s), 2.14–5.20 (15H, m), 6.64–8.74 (11H, m), 10.95 (1H, s) MASS (APCI) 589 (M+H)$^+$ (free)

(3) (2R)-1-[3,5-Bis(trifluoromethyl)benzoyl]-2-(3,4-dimethylbenzyl)-4-{3-[2-(4-methoxycarbonyl)pyridyl]propyl}piperazine dihydrochloride mp: 115–125° C. $[\alpha]_D^{28}$: −11.7° (C=0.5, MeOH) IR (KBr): 2650, 2625, 1740, 1645, 1460, 1280, 1135 cm$^{-1}$ NMR (DMSO-d$_6$, δ): 3.92 (3H, s), 2.07–5.14 (21H, m), 6.60–8.78 (9H, m) MASS (APCI): 622 (M+H)$^+$ (free)

EXAMPLE 84

To a stirred suspension of 2-(3,4-methylenedioxybenzyl)piperazine dihydrochloride (104 mg) and potassium carbonate (196 mg) in N,N-dimethylformamide (4 ml) was added 4-(4-chloro-2-butynyl)-3,3-dimethylmorpholine hydrochloride (84.5 mg) at 5° C. under nitrogen atmosphere and the mixture was gradually warmed to room temperature over night. To the above stirred suspension was added 3,5-bis(trifluoromethyl)benzoyl chloride (98.2 mg) at 5° C. and the mixture was stirred for 1 hour at this temperature. The mixture was extracted with ethyl acetate and the extract was washed with water, and dried over magnesium sulfate. The usual work up followed by flash chromatography on silica gel with a mixture of dichloromethane and methanol (50:1) gave 1-[3,5-bis-(trifluoromethyl)benzoyl]-4-[4-(3,3-dimethylmorpholino)-2-butynyl]-2-(3,4-methylenedioxybenzyl)piperazine, which was dissolved in ethyl acetate and treated with 4N hydrogen chloride in ethyl acetate to give 1-[3,5-bis-(trifluoromethyl)benzoyl]-4-[4-(3,3-dimethylmorpholino)-2-butynyl]-2-(3,4-methylenedioxybenzyl)piperazine dihydrochloride (107 mg) as a powder.

NMR (DMSO-d$_6$, δ): 1.32 (6H, m), 2.20–5.00 (19H, m), 5.96 (2H, s), 6.43–8.17 (6H, m) MASS (APCI): 626 (M+H)$^+$ (free)

EXAMPLE 85

The following compounds were obtained according to a similar manner to that of Example 84.

(1) 1-[3,5-Bis(trifluoromethyl)benzoyl]-4-[4-(3,3-dimethylmorpholino)-2-butynyl]-2-(4-hydroxymethyl-3-methylbenzyl)piperazine dihydrochloride NMR (DMSO-d$_6$, δ): 1.32–1.38 (6H, m), 2.00–5.22 (25H, m), 6.55–8.17 (6H, m) MASS (APCI): 626 (M+H)$^+$ (free)

(2) 2-[(1,4-Benzodioxan-6-yl)methyl]-1-[3,5-bis-(trifluoromethyl)benzoyl]-4-[4-(3,3-dimethylmorpholino)-2-butynyl]piperazine dihydrochloride NMR (DMSO-d$_6$, δ): 1.21–1.23(6H, m), 2.62–5.00 (23H, m), 6.37–8.48 (6H, m) MASS (APCI): 640 (M+H)$^+$ (free)

(3) 1-[3,5-Bis(trifluoromethyl)benzoyl]-4-[4-(3,3-dimethylmorpholino)-2-butynyl]-2-(4-methoxy-3-methylbenzyl)piperazine dihydrochloride NMR (DMSO-d$_6$, δ): 1.33–1.40 (6H, m), 2.00–5.22 (25H, m), 6.64–8.15 (6H, m) MASS (APCI): 626 (M+H)$^+$ (free)

EXAMPLE 86

To a mixed solution of 1-(benzyloxycarbonyl)-3-(2,3-dimethoxybenzyl)piperazine (0.65 g) and triethylamine (0.293 ml) in dichloromethane (17 ml) was added dropwise a solution of 3,5-bis(trifluoromethyl)benzoyl chloride (0.534 g) in dichloromethane (2.5 ml) under ice-cooling. After being stirred at the same temperature for 2 hours, the reaction mixture was poured into a mixed solvent of water (40 ml) and dichloromethane (25 ml) and the whole was adjusted to pH 9 with aqueous sodium hydrogen carbonate solution. The organic layer was separated, washed with brine, dried over sodium sulfate and evaporated under reduced pressure. The residue was purified by column chromatography on silica gel (10 g) using a mixed solvent of n-hexane and ethyl acetate (2:1). The fractions containing the objective compound were collected and evaporated under reduced pressure to give 1-[3,5-bis(trifluoromethyl)benzoyl]-4-(benzyloxycarbonyl)-2-(2,3-dimethoxybenzyl)piperazine (0.84 g).

IR (KBr): 1732, 1714, .1705, 1647, 1431, 1281, 1134 cm$^{-1}$ NMR (CDCl$_3$, δ): 2.60–4.70 (9H, m), 3.79 (6H, s), 5.20 (2H, s), 6.40–8.60 (11H, m) MASS (APCI): 611 (M+H)$^+$

EXAMPLE 87

A mixture of 1-[3,5-bis(trifluoromethyl)benzoyl]-2-(2,3-dimethoxybenzyl)piperazine (0.192 g), 3,3-dimethyl-4-(4-chloro-2-butynyl)morpholinine hydrochloride (0.106 g), potassium carbonate (0.167 g) and potassium iodide (67 mg) in N,N-dimethylformamide (1.3 ml) was stirred at 65° C. for 90 minutes and cooled. The mixture was poured into ice-water (30 ml) and the whole was adjusted to pH 9 with sodium bicarbonate, and extracted with ethyl acetate (30 ml). The extract was washed with brine (30 ml), dried over sodium sulfate and evaporated under reduced pressure. The residue was purified by column chromatography on silica gel (8 g) using a mixed solvent of dichloromethane and methanol (40:1). The fractions containing the objective compound were collected and evaporated under reduced pressure to give a colorless oil of 1-[3,5-bis(trlfluoromethyl)benzoyl]-2-(2,3-dimethoxybenzyl)-4-[4-(3,3-dimethylmorpholino)-2-butynyl]piperazine. The oil was dissolved in ethyl acetate (2 ml) and the solution was treated with 4N hydrogen chloride in ethyl acetate solution (0.30 ml) under ice-cooling, and evaporated under reduced pressure to give colorless powder of 1-[3,5-bis(trifluoromethyl)benzoyl]-2-(2,3-dimethoxybenzyl)-4-[4-(3,3-dimethylmorpholino)-2-butynyl]piperazine dihydrochloride (0.18 g).

mp: 170° C. IR (KBr): 2933, 2575, 1647, 1637, 1433, 1281, 1186, 1136 cm$^{-1}$ NMR (DMSO-d$_6$, δ): 1.33 (3H, s), 1.41 (3H, s), 2.60–5.20 (19H, m), 3.75 (6H, s), 6.50–7.00 (3H, m), 7.50–8.20 (3H, m) MASS (APCI): 642 (M+H)$^+$ (free)

EXAMPLE 88

The following compound was obtained according to a similar manner to that of Example 86.

1-[3,5-Bis(trifluoromethyl)benzoyl]-4-(benzyloxycarbonyl)-2-[(1H-indol-2-yl)methyl]piperazine IR (KBr): 1714, 1699, 1684, 1647, 1635, 1458, 1281 cm$^{-1}$ NMR (DMSO-d$_6$, δ): 2.60–5.10 (9H, m), 5.15 (2H, s), 5.98–8.48 (13H, m), 10.58–11.04 (1H, m) MASS (APCI): 590 (M+H)$^+$

EXAMPLE 89

The following compounds were obtained according to a similar manner to that of Example 87.

(1) 1-[3,5-Bis(trifluoromethyl)benzoyl]-2-[(1H-indol-2-yl)methyl]-4-[4-(3,3-dimethylmorpholino)-2-butynyl]piperazine dihydrochloride mp: 185° C. IR (KBr): 1651, 1647, 1637, 1281, 1188, 1136 cm$^{-1}$ NMR (DMSO-d$_6$, δ): 1.31 (3H, s), 1.40 (3H, s), 3.00–5.22 (19H, m), 6.02–6.40 (1H, m), 6.90–8.20 (7H, m), 11.70–11.17 (1H, m) MASS (APCI): 621 (M+H)$^+$ (free)

(2) 1-[3,5-Bis(trifluoromethyl)benzoyl]-2-(3-methoxybenzyl)-4-[4-(3,3-dimethyl)morpholino-2-butynyl]piperazine dihydrochloride mp: 223–225° C. IR (KBr): 3600–3300, 2900, 2600–2300, 1647, 1635, 1458, 1435, 1280 cm$^{-1}$ NMR (DMSO-d$_6$, δ) 1.32 (3H, s), 1.40 (3H, s), 2.8–5.2 (22H, m), 6.5–8.20 (7H, m), 12.1–12.6 (2H, m) MASS (APCI): 612 (M+H)$^+$ (free)

EXAMPLE 90

The following compounds were obtained according to a similar manner to that of Example 9.

(1) (2R)-4-[4-(3,3-Dimethylmorpholino)-2-butynyl]-2-[(1H-indol-3-yl)methyl]-1-[3-(methylamino)-5-(trifluoromethyl)benzoyl]piperazine dihydrochloride mp: 215–230° C. [α]$_D^{27}$: +41.8° (C=0.5, MeOH) IR (KBr): 3600–3300, 2900, 2600–2300, 1645, 1624, 1614, 1458, 1419 cm$^{-1}$ NMR (DMSO-d$_6$, δ): 1.20–1.50 (6H, m), 2.69 (3H, s), 2.90–5.30 (19H, m), 6.55–7.90 (9H, m), 10.98 (1H, br s), 11.90–12.60 (2H, m) MASS (APCI): 582 (M+H)$^+$ (free)

(2) (2R)-1-[3-(Dimethylamino)-5-(trifluoromethyl)benzoyl]-4-[4-(3,3-dimethylmorpholino)-2-butynyl]-2-[(1H-indol-3-yl)methyl]piperazine dihydrochloride mp: 210–225° C. [α]$_D^{27}$: +31.8° (C=0.5, MeOH) IR (KBr): 3600–3300, 2900, 2600–2300, 1653, 1647, 1635, 1558, 1541, 1508, 1473, 1458, 1419 cm$^{-1}$ NMR (DMSO-d$_6$, δ): 1.20–1.50 (6H, m), 2.70–5.28 (19H, m), 2.94 (6H, s), 6.48–7.90 (8H, m), 10.99 (1H, br s), 12.00–12.50 (2H, m) MASS (APCI): 596 (M+H)$^+$ (free)

(3) (2R)-4-[4-(3,3-Dimethylmorpholino)-2-butynyl]-2-[(1H-indol-3-yl)methyl]-1-[3-nitro-5-(trifluoromethyl)benzoyl]piperazine dihydrochloride mp: 198–220° C. IR (KBr): 3600–3300, 2900, 2600–2300, 1645, 1635, 1543, 1471, 1458, 1421, 1358, 1331 cm$^{-1}$ NMR (DMSO-d$_6$, δ): 1.33 (3H, s), 1.41 (3H, s), 2.80–5.22 (19H, m), 6.50–8.62 (8H, m), 10.99 (1H, s), 11.80–12.60 (2H, m) MASS (APCI): 598 (M+H)$^+$ (free)

(4) (2R)-2-(3,4-Dimethylbenzyl)-4-[4-(3,3-dimethylmorpholino)-2-butynyl]-1-[3-(methylamino)-5-(trifluoromethyl)benzoyl]piperazine dihydrochloride mp: 195–205° C. [α]$_D^{27}$: +10.8° (C=0.5, MeOH) IR (KBr): 3600–3300, 2900, 2600–2300, 1647, 1635, 1616, 1456, 1419 cm$^{-1}$ NMR (DMSO-d$_6$, δ) 1.32 (3H, s), 1.40 (3H, s), 2.00–2.30 (6H, m), 2.70 (3H, s), 2.90–5.20 (19H, m), 6.20–7.20 (7H, m), 12.22 (2H, br s) MASS (APCI): 571 (M+H)$^+$ (free)

(5) (2R)-1-[3-(Dimethylamino)-5-(trifluoromethyl)benzoyl]-2-(3,4-dimethylbenzyl)-4-[4-(3,3-dimethylmorpholino)-2-butynyl]piperazine dihydrochloride mp: 108–185° C. [α]$_D^{27}$: +8.80° (C=0.5, MeOH) IR (KBr): 3600–3300, 2900, 2600–2300, 1647, 1635, 1616, 1608, 1506, 1456, 1425 cm$^{-1}$ NMR (DMSO-d$_6$, δ): 1.32 (3H, s), 1.40 (3H, s), 2.02–2.30 (6H, m), 2.95 (6H, s), 3.00–5.25 (19H, m), 6.20–7.20 (6H, m), 12.28 (2H, br s) MASS (APCI): 585 (M+H)$^+$ (free)

(6) (2R)-2-(3,4-Dimethylbenzyl)-4-[4-(3,3-dimethylmorpholino)-2-butynyl]-1-[3-nitro-5-(trifluoromethyl)benzoyl]piperazine dihydrochloride mp: 157–200° C. [α]$_D^{26}$: +19.5° (C=0.5, MeOH) IR (KBr): 3600–3300, 2900, 2600–2300, 1647, 1637, 1543, 1456, 1423, 1356, 1330, 1319 cm$^{-1}$ NMR (DMSO-d$_6$, δ): 1.33 (3H, s), 1.41 (3H, s), 1.95–2.34 (6H, m), 2.62–5.20 (19H, m), 6.60–8.60 (6H, m), 12.10–12.50 (2H, m) MASS (APCI): 587 (M+H)$^+$ (free)

Preparation 72

The following compounds were obtained by a similar manner to that of Preparation 38.

(1) (2R)-1-[3,5-Bis(trifluoromethyl)benzoyl]-2-[(1H-indol-3-yl)methyl]-4-(2-hydroxyethyl)piperazine IR (Neat): 3300, 2930, 2800, 1623 cm$^{-1}$ NMR (DMSO-d$_6$, δ): 2.00–5.00 (14H, m), 6.60–8.28 (8H, m), 10.86 (.1H, s) MASS (APCI): 500 (M+H)$^+$ (2) (2R)-1-[3,5-Bis(trifluoromethyl)benzoyl]-2-(3,4-dimethylbenzyl)-4-(2-hydroxyethyl)piperazine IR (Neat): 3400, 1640, 1430, 1280, 1170 cm$^{-1}$ NMR (DMSO-d$_6$, δ): 2.00–5.00 (20H, m), 6.60–8.20 (6H, m)

Preparation 73

The following compounds were obtained by a similar manner to that of Example 39.

(1) (2R)-1-[3,5-Bis(trifluoromethyl)benzoyl]-2-[(1H-indol-3-yl)methyl]-4-(2-methanesulfonyloxyethyl)piperazine IR (Neat): 3340, 3300, 3000, 2930, 2800, 1624 cm$^{-1}$ NMR (DMSO-d$_6$, δ) 2.10–4.70 (13H, m), 3.24 (3H, s), 6.26–8.28 (8H, m), 10.90 (1H, s) MASS (APCI): 578 (M+H)$^+$ (2) (2R)-1-[3,5-Bis(trifluoromethyl)benzoyl]-2-(3,4-dimethylbenzyl)-4-(2-methanesulfonyloxyethyl)piperazine IR (Neat): 1640, 1430, 1280, 1150 cm$^{-1}$ NMR (DMSO-d$_6$, δ): 2.00–5.00 (23H, m), 6.60–8.20 (6H, m) MASS (APCI): 567, 489

Preparation 74

The following compound was obtained by a similar manner to that of Preparation 37.

(2R)-1-[3,5-Bis(trifluoromethyl)benzoyl]-2-[(1H-indol-3-yl)methyl]-4-(4-chloro-2-butynyl)piperazine IR (Neat): 3300, 3050, 2800, 2600, 1630, 1430 cm$^{-1}$ NMR (CDCl$_3$, δ): 2.20–5.30 (13H, m), 6.75–8.20 (8H, m) MASS (APCI): 542 (M+H)$^+$ Preparation 75

(1) The following compound was obtained by a similar manner to that of Preparation 46-(4).

1-Acetyl-3-(3-methoxy-4-methylphenyl)methylene-2,5-piperazinedione

NMR (DMSO-d$_6$, δ): 2.17 (3H, s), 2.50 (3H, s), 3.83 (3H, s), 4.37 (2H, s), 6.95 (1H, s), 7.08–7.22 (3H, m), 10.33 (1H, s) MASS (APCI): 289 (M+H)$^+$ (2) The following compound was obtained by a similar manner to that of Preparation 46-(5).

3-(3-Methoxy-4-methylbenzyl)-2,5-piperazinedione

NMR (DMSO-d$_6$, δ): 2.11 (3H, s), 2.75 (1H, d, J=17.4 Hz), 2.84 (1H, m), 3.05 (1H, dd, J=13.4, 4.5 Hz), 3.35 (1H, m), 3.73 (3H, s), 4.04 (1H, m), 6.63 (1H, d, J=7.4 Hz), 6.73 (1H, s), 7.03 (1H, d, J=7.4 Hz), 7.88 (1H, m), 8.13 (1H, m) MASS (APCI): 249 (M+H)$^+$ (3) The following compound was obtained by a similar manner to that of Preparation 47-(3).

2-(3-Methoxy-4-methylbenzyl)piperazine dihydrobromide

NMR (DMSO-d$_6$, δ): 2.13 (3H, s), 2.78–3.78 (9H, m), 3.81 (3H, s), 6.73–7.15 (3H, m), 9.11 (4H, m) MASS (APCI): 221 (M+H)$^+$ (free)

(4) A stirred solution of 2-(3-methoxy-4-methylbenzyl)piperazine dihydrobromide (240 mg) in 48% hydrobromic acid (8 ml) was heated under reflux for 48 hours. After cooling, the mixture was concentrated under reduced pressure. The residue was triturated with ethyl acetate and the resulting precipitates were collected by filtration, and washed with ethyl acetate to give 2-(3-hydroxy-4-methylbenzyl)piperazine dihydrobromide (175 mg) as a powder.

NMR (DMSO-d$_6$, δ): 2.11 (3H, s), 2.67–3.78 (9H, m), 6.70–6.95 (3H, m), 9.09 (4H, m) MASS (APCI): 207 (M+H)$^+$ (free)

EXAMPLE 91

The following compounds were obtained by a similar manner to that of Example 84.

(1) 1-[3,5-Bis(trifluoromethyl)benzoyl]-4-[4-(3,3-dimethylmorpholino)-2-butynyl]-2-(3-hydroxy-4-methylbenzyl)piperazine dihydrochloride NMR (DMSO-d$_6$, δ): 1.32–1.38 (6H, m), 2.08 (3H, s), 2.68–5.03 (20H, m), 6.18–8.20 (6H, m) MASS (APCI): 612 (M+H)$^+$ (free)

(2) 1-[3,5-Bis(trifluoromethyl)benzoyl]-4-[4-(3,3-dimethylmorpholino)-2-butynyl]-2-(3-methoxy-4-methylbenzyl)piperazine dihydrochloride NMR (DMSO-d$_6$, δ): 1.33–1.38 (6H, m), 2.10 (3H, s), 2.73–5.10 (22H, m), 6.40–8.18 (6H, m) MASS (APCI): 626 (M+H)$^+$ (free)

(3) 1-[3,5-Bis(trifluoromethyl)benzoyl]-4-[4-(3,3-dimethylmorpholino)-2-butynyl]-2-(4-hydroxy-3-methylbenzyl)piperazine dihydrochloride NMR (DMSO-d$_6$, δ): 1.32–1.38 (6H, m), 2.09 (3H, s), 2.73–4.98 (20H, m), 6.55–8.20 (6H, m) MASS (APCI): 612 (M+H)$^+$ (free)

Preparation 76

The following compound was obtained according to a similar manner to that of Preparation 75-(4).

2-(4-Hydroxy-3-methylbenzyl)piperazine dihydrobromide

NMR (DMSO-d$_6$, δ): 2.10 (3H, s), 2.67–3.57 (9H, m), 6.57–7.11 (3H, m), 9.12–9.39 (5H, m) MASS (APCI): 207 (M+H)$^+$ (free)

Preparation 77

(1) The following compound was obtained according to a similar manner to that of Preparation 46-(4).

1-Acetyl-3-(3-nitrophenyl)methylene-2,5-piperazinedione mp: 190–200° C. NMR (DMSO-d$_6$, δ): 2.51 (3H, s), 4.32 (2H, s), 7.03 (1H, s), 7.65 (1H, m), 7.94 (1H, d, J=7.8 Hz), 8.16 (1H, dd, J=1.6, 7.8 Hz), 8.37 (1H, d, J=1.6 Hz), 10.80 (1H, br s) MASS (APCI): 290 (M+H)$^+$ 79

(2) A mixture of 1-acetyl-3-(3-nitrophenyl)methylene-2,5-piperazinedione (10.2 g), triethylamine (6.43 ml) and di-tert-butyl dicarbonate (23.5 g) in N,N-dimethylformamide (50 ml) was hydrogenated over 10% palladium-carbon (50% wet, 1 g) at room temperature under 2–3 atmospheres. After removal of catalyst by filtration, the filtrate was concentrated by evaporation, the residue was partitioned between ethyl acetate and water. The organic layer was washed with brine, dried over magnesium sulfate and evaporated under reduced pressure. The residue was purified by column chromatography on silica gel using a mixture of dichloromethane and methanol (20:1). The fractions containing the objective compound were collected and evaporated under reduced pressure. The resulting precipitates were collected by filtration and washed with methanol to give 1-acetyl-3-[3-(tert-butoxycarbonylamino)benzyl]-2,5-piperazinedione (1.3 g) as colorless powders.

mp: 189–190° C. IR (KBr): 3334, 1727, 1704, 1681, 1602, 1590, 1540 cm$^{-1}$ NMR (DMSO-d$_6$, δ): 1.46 (9H, s), 2.43 (3H, s), 2.94 (1H, dd, J=6.4, 14.2 Hz), 3.10 (1H, dd,

J=6.4, 14.2), 3.15 (1H, d, J=17.4 Hz), 3.96 (1H, d, J=17.4 Hz), 4.30–4.35 (1H, m), 6.58 (1H, d, J=7.1 Hz), 7.15 (1H, m), 7.23 (1H, d, J=7. Hz), 7.43 (1H, s), 7.42 (1H, d, J=2.8 Hz), 9.32 (1H, s) MASS (APCI): 306 (M–(CH$_3$)$_3$)$^+$ (3) The following compound was obtained according to a similar manner to that of Preparation 46-(5).

3-[3-(tert-Butoxycarbonylamino)benzyl]-2,5-piperazinedione mp: 230–233° C. IR (KBr): 3301, 3212, 3083, 2981, 1716, 1675, 1608 cm$^{-1}$ NMR (DMSO-d$_6$, δ): 1.47 (9H, s), 2.89 (1H, dd, J=5.3, 9.1 Hz), 2.95 (1H, d, J=17.0 Hz), 2.96 (1H, dd, J=5.3, 9.1 Hz), 3.36 (1H, dd, J=3.8, 17.0 Hz), 3.95–4.00 (1H, m), 6.78 (1H, d, J=7.8 Hz), 7.14 (1H, m), 7.30–7.35 (2H, m), 7.91 (1H, br s), 8.13 (1H, br s), 9.30 (1H, s) MASS (APCI): 320 (M+H)$^+$, 264

(4) A solution of 3-[3-(tert-butoxycarbonylamino)benzyl]-2,5-piperazinedione. (0.75 g) in trifluoroacetic acid (10 ml) was stirred for 4 hours at room temperature. After removal of the solvent by evaporation, the residue was dissolved in a mixture of dichloromethane (10 ml) and methanol (3 ml) and thereto benzaldehyde (0.742 g) and sodium triacetoxyborohydride (2.11 g) were added. The whole was stirred for 2 hours at room temperature and concentrated under reduced pressure. The residue was purified by column chromatography on silica gel using a mixture of dichloromethane and methanol (25:1). The fractions containing the objective compound were collected and triturated with isopropyl alcohol to give 2-[3-(benzylamino)benzyl]-3,6-piperazinedione (0.43 g) as colorless crystals.

mp: 160–161° C. IR (KBr): 3168, 3056, 2975, 2867, 1677, 1606, 1550 cm$^{-1}$ NMR (DMSO-d$_6$, δ): 2.86 (1H, d, J=17.2 Hz), 2.82 (1H, dd, J=4.8, 13.3 Hz), 2.92 (1H, dd, J=4.8, 13.3 Hz), 3.33 (1H, dd, J=3.0, 17.2 Hz), 3.96 (1H, d, J=3.0 Hz), 4.21 (2H, d, J=6.0 Hz), 6.16 (1H, m), 6.33 (1H, d, J=7.4 Hz), 6.41–6.45 (2H, m), 6.92 (1H, m), 7.18–7.33 (5H, m), 7.78 (1H, br s), 8.04 (1H, d, J=2.2 Hz) MASS (APCI): 310 (M+H)$^+$ (5) A suspension of 2-[3-(benzylamino)benzyl]-3,6-piperazinedione (0.45 g), 37% aqueous formaldehyde (81 mg), sodium triacetoxyborohydride (0.62 g) and acetic acid (175 mg) in a mixture of 1,2-dichloroethane (15 ml) and N,N-dimethylformamide (5 ml) was stirred for 5 hours at room temperature. Then additional 37% aqueous formaldehyde (0.1 ml), acetic acid (0.2 ml) and sodium triacetoxyborohydride (0.60 g) were added to the reaction mixture and the whole was stirred for further 2 hours. The mixture was concentrated under reduced pressure and the residue was purified by column chromatography on silica gel using a mixture of dichloromethane and methanol (10:1). The fractions containing the objective compound were collected and evaporated under reduced pressure. The resulting precipitates were collected by filtration and washed with isopropyl alcohol to give 2-[3-(N-benzyl-N-methylamino)benzyl]-3,6-piperazinedione (0.46 g) as colorless crystals.

NMR (DMSO-d$_6$, δ): 2.71–3.03 (3H, m), 2.94 (3H, s), 3.27–3.37 (1H, m), 4.00–4.05 (1H, m), 4.53 (2H, s), 6.42 (1H, d, J=7.5 Hz), 6.57–6.61 (2H, m), 6.98–7.06 (1H, m), 7.16–7.34 (5H, m), 7.85 (1H, s), 8.09 (1H, d, J=2.2 Hz) MASS (APCI): 324 (M+H)$^+$ (6) The following compound was obtained according to a similar manner to that of Preparation 49-(4).

2-[3-(N-Benzyl-N-methylamino)benzyl]piperazine

The compound was used to the next step without further purification.

Preparation 78

The following compound was obtained according to a similar manner to that of Preparation 50.

1-[3,5-Bis(trifluoromethyl)benzoyl]-2-[3-(N-methylamino)benzyl]piperazine

NMR (CDCl$_3$, δ): 2.20–5.20 (10H, m), 2.99 (3H, s), 6.00–7.40 (7H, m), 8.16 (1H, s) MASS (APCI): 446 (M+H)$^+$

EXAMPLE 92

The following compound was obtained according to a similar manner to that of Preparation 49-(5) through a similar manner to that of Example 86.

1-[3,5-Bis(trifluoromethyl)benzoyl]-2-[3-N-benzyl-N-methylamino)benzyl]-4-(benzyloxycarbonyl)piperazine IR (Neat): 1705, 1645, 1605, 1505 cm$^{-1}$ NMR (CDCl$_3$, δ): 2.60–4.80 (14H, m), 5.18 (2H, s), 6.10–7.40 (16H, m), 7.84 (1H, s) MASS (APCI): 670 (M+H)$^+$

EXAMPLE 93

The following compound was obtained according to a similar manner to that of Example 87.

1-[3,5-Bis(trifluoromethyl)benzoyl]-4-[4-(3,3-dimethylmorpholino)-2-butynyl]-2-[3-(N-methylamino)benzyl]piperazine IR (Neat): 3400, 1680, 1640, 1610 cm$^{-1}$ NMR (CDCl$_3$, δ): 1.06 (6H, br s), 2.10–5.20 (20H, m), 3.34 (3H, s), 5.95–7.80 (7H, m) MASS (APCI): 611 (M+H)$^+$ its trihydrochloride mp: 192–195° C. IR (KBr): 3500–3300, 3000–2800, 2700–2300, 1644 cm$^{-1}$ NMR (CDCl$_3$, δ): 1.36 (6H, s), 2.71–2.81 (3H, m), 3.20–5.20 (20H, m), 6.60–8.21 (7H, m) MASS (APCI): 611 (M+H)$^+$ (free)

EXAMPLE 94

A suspension of 1-[3,5-bis(trifluoromethyl)benzoyl]-4-[4-(3,3-dimethylmorpholino)-2-butynyl]-2-[3-(N-methylamino)benzyl]piperazine (0.19 g), 37% aqueous formaldehyde (50 μl), sodium triacetoxyborohydride (79 mg) and acetic acid (22 μl) in dichloromethane (5 ml) was stirred for 2 hours at room temperature. Then additional 37% aqueous formaldehyde (25 μl), acetic acid (10 μl) and sodium triacetoxyborohydride (40 mg) were added to the reaction mixture and the whole was stirred for further 1 hour. The mixture was poured into aqueous saturated sodium hydrogen carbonate solution and extracted with dichloromethane. The extract was dried over magnesium sulfate and evaporated under reduced pressure. The residue was purified by column chromatography on silica gel using a mixture of dichloromethane and methanol (40:1). The fractions containing the objective compound were collected and evaporated under reduced pressure and treated with 4N hydrogen chloride in ethyl acetate solution to give 1-[3,5-bis(trifluoromethyl)benzoyl]-2-[3-(N,N-dimethylamino)benzyl]-4-[4-(3,3-dimethylmorpholino)-2-butynyl]piperazine trihydrochloride (0.21 g).

mp: 205–210° C. IR (KBr): 3500–3300, 2900–2500, 1644 cm$^{-1}$ NMR (DMSO-d$_6$, δ): 1.32 (3H, s), 1.41 (3H, s), 2.91 (3H, s), 3.03 (3H, s), 3.20–5.20 (19H, m), 6.40–8.25 (7H, m) MASS (APCI): 625 (M+H)$^+$ (free)

What is claimed is:
1. A compound of the formula:

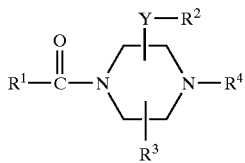

wherein
Y is bond or lower alkylene,
$R^1$ is aryl which may have substituent(s),
$R^2$ is aryl or indolyl, each of which may have substituent(s),
$R^3$ is hydrogen or lower alkyl,
$R^4$ is pyridyl(lower)alkylamino(lower)alkynyl;
N-(lower alkyl)-N-[pyridyl(lower)alkyl]amino-(lower)alkyl;
hydroxy(lower)alkoxy(lower)alkyl;
lower alkanoyl(lower)alkoxy(lower)alkyl;
phenyl(lower)alkyl which has hydroxy(lower)alkyl or morpholinyl(lower)alkyl;
ar(lower)alkoxycarbonyl;
(2-pyridyl) (lower)alkyl which may have 1 to 3 substituent(s) selected from the group consisting of lower alkyl, lower alkoxy, lower alkoxycarbonyl, mono(or di or tri)halo(lower)alkyl and halogen;
(3-pyridyl)propyl which may have lower alkoxy or amino;
(3-pyridyl)butyl which may have lower alkoxy or amino;
pyridyl(lower)alkenyl which may have lower alkoxy or amino;
(2-pyridyl) (lower)alkynyl which may have 1 to 3 substituent(s) selected from the group consisting of lower alkyl, lower alkoxy, lower alkoxycarbonyl, mono(or di or tri)halo(lower)alkyl and halogen;
(3-pyridyl) (lower) alkynyl which may have lower alkoxy or amino;
pyridyl, thiazolyl, imidazolyl or pyrazolyl, each of which may have substituent(s);
imidazolyl(lower)alkyl which may have 1 or 2 substituent(s) selected from the group consisting of lower alkyl, lower alkynyl, ar(lower)alkyl, pyridyl (lower)alkyl, mono(or di or tri)halo(lower)alkyl and halogen;
pyrazolyl(lower)alkyl which may have hydroxy(lower)alkyl, carboxy(lower)alkyl, lower alkoxycarbonyl (lower)alkyl, morpholinyl(lower)alkyl or morpholinylcarbonyl(lower)alkyl;
thiazolyl(lower)alkyl which may have lower alkyl;
piperidyl(lower)alkyl which may have hydroxy(lower)alkyl or lower alkoxy;
morpholinyl(lower)alkyl which has 1 or 2 substituent(s) selected from the group consisting of ethyl, hydroxy(lower)alkyl, halo(lower)alkyl and lower alkoxy(lower)alkyl;
morpholinyl(lower)alkyl which has lower alkyl and lower alkoxy(lower)alkyl;
(3,5-dimethylmorpholino)(lower)alkyl;
morpholino(lower)alkenyl which may have lower alkyl or lower alkoxy(lower)alkyl;
(2- or 3-morpholinyl) (lower)alkenyl which may have lower alkoxycarbonyl;
pyrrolidinyl(lower)alkynyl which may have lower alkoxy(lower)alkyl;
morpholinyl(lower)alkynyl which may have 1 or 2 substituent(s) selected from the group consisting of ethyl, propyl, isopropyl, isobutyl, spirocyclo(lower) alkyl, lower alkoxy(lower)alkyl, hydroxy(lower) alkyl, carboxy(lower)alkyl, di(lower alkyl) carbamoyl, lower alkoxycarbonyl and halo(lower) alkyl;
morpholinyl(lower)alkynyl which has methyl and lower alkoxy;
(dimethylmorpholino)(lower)alkynyl;
homomorpholinyl(lower)alkynyl which have halogen;
(morpholinylamino)propyl which may have lower alkanoyl;
thiomorpholinyl(lower)alkynyl which may have substituent(s);
homomorpholinylamino(lower)alkyl;
thiomorpholinylamino(lower)alkyl; or
saturated heterocyclicimino(lower)alkyl, saturated heterocyclicaminocarbonyl(lower)alkyl or saturated heterocyclic(lower)alkoxy(lower)alkyl, each of which may have substituent(s),
provided that when
$R^4$ is 2-[N-methyl-N-(3-pyridylmethyl)amino]ethyl,
3-(3-pyridyl)propyl,
3-(3-pyridyl)-2-propynyl,
4-[(2-methoxymethyl)pyrrolidino]-2-butynyl,
4-thiomorpholino-2-butynyl,
3-(morphlinoamino)propyl,
4-morpholino-2-butenyl,
4-morpholino-2-butynyl, or
4-(3,3-dimethylmorpholino)-2-butynyl, then
$R^1$ is not 3,5-bis(trifluoromethyl)phenyl,
and a salt thereof.
2. The compound of claim 1, in which
Y is lower alkylene,
$R^1$ is $C_6$–$C_{10}$ aryl which may have 1 or 2 substituent(s) selected from the group consisting of mono(or di or tri)halo(lower)alkyl, halogen, lower alkylamino, di(lower)alkylamino and nitro,
$R^2$ is $C_6$–$C_{10}$ aryl or indolyl, each of which may have 1 to 3 substituent(s) selected from the group consisting of lower alkyl, mono(or di or tri)halo(lower)alkyl, lower alkylenedioxy, hydroxy, hydroxy(lower)alkyl, lower alkoxy, lower alkylamino and di(lower)alkylamino,
$R^3$ is hydrogen, and
$R^4$ is pyridyl(lower)alkylamino(lower)alkynyl;
(2-pyridyl)propyl which may have 1 to 3 substituent(s) selected from the group consisting of lower alkyl, lower alkoxy, lower alkoxycarbonyl, mono(or di or tri)halo(lower)alkyl and halogen;
pyridyl, thiazolyl, imidazolyl or pyrazolyl, each of which may have 1 or 2 substituent(s) selected from the group consisting of lower alkyl, ar(lower)alkyl and pyridyl(lower)alkyl;
imidazolyl(lower)alkyl which has 1 or 2 substituent(s) selected from the group consisting of lower alkyl, lower alkynyl, ar(lower)alkyl, pyridyl(lower)alkyl, mono(or di or tri)halo(lower)alkyl and halogen;
(2-methyl-1H-imidazol-4-yl) (lower)alkyl which has 1 or 2 substituent(s) selected from the group consisting of isopropyl, lower alkynyl, ar(lower)alkyl, pyridyl (lower)alkyl, mono(or di or tri)halo(lower)alkyl and halogen;
(5-methyl-1H-imidazol-4-yl) (lower)alkyl which has 1 or 2 substituent(s) selected from the group consisting of isopropyl, lower alkynyl, ar(lower)alkyl, pyridyl (lower)alkyl, mono(or di or tri)halo(lower)alkyl and halogen;

piperidyl(lower)alkyl which may have hydroxy(lower) alkyl or lower alkoxy;
morpholinyl(lower)alkyl which has 1 or 2 substituent (s) selected from the group consisting of ethyl, hydroxy(lower)alkyl, halo(lower)alkyl and lower alkoxy(lower)alkyl;
morpholinyl(lower)alkyl which has lower alkyl and lower alkoxy(lower)alkyl;
(3,5-dimethylmorpholino) (lower)alkyl;
morpholino(lower)alkenyl which may have lower alkyl or lower alkoxy(lower)alkyl;
(2- or 3-morpholinyl) (lower)alkenyl which may have lower alkoxycarbonyl;
pyrrolidinyl(lower)alkynyl which may have lower alkoxy(lower)alkyl;
morpholinyl(lower)alkynyl which may have 1 or 2 substituent(s) selected from the group consisting of ethyl, propyl, isopropyl, isobutyl, spirocyclo(lower) alkyl, lower alkoxy(lower)alkyl, hydroxy(lower) alkyl, carboxy(lower)alkyl, di(lower alkyl) carbamoyl, lower alkoxycarbonyl and halo(lower) alkyl;
morpholinyl(lower)alkynyl which has methyl and lower alkoxy(lower)alkyl;
(dimethylmorpholino) (lower)alkynyl; or
homomorpholinyl(lower)alkynyl which may have halogen.

3. The compound of claim 2, in which
Y is lower alkylene,
$R^1$ is phenyl which has 1 -or 2 substituent(s) selected from the group consisting of trihalo(lower)alkyl, halogen, lower alkylamino, di(lower)alkylamino and nitro,
$R^2$ is phenyl or indolyl, each of which have 1 or 2 substituent(s) selected from the group consisting of lower alkyl, trihalo(lower)alkyl, lower alkylenedioxy, hydroxy, hydroxy(lower)alkyl, lower alkoxy, lower alkylamino and di(lower)alkylamino,
$R^3$ is hydrogen, and
$R^4$ is (2-pyridyl)propyl which may have 1 to 3 substituent (s) selected from the group consisting of lower alkyl, lower alkoxy, mono(or di or tri)halo(lower)alkyl and halogen;
morpholinyl(lower)alkyl which has 1 or 2 substituent (s) selected from the group consisting of ethyl, hydroxy(lower)alkyl, halo(lower)alkyl and lower alkoxy(lower)alkyl;
morpholinyl(lower)alkynyl which may have 1 or 2 substituent(s) selected from the group consisting of ethyl, propyl, isopropyl, isobutyl, spirocyclo(lower) alkyl, lower alkoxy(lower)alkyl, hydroxy(lower) alkyl, carboxy(lower)alkyl, di(lower alkyl) carbamoyl, lower alkoxycarbonyl and halo(lower) alkyl.

4. A compound of claim 3, which is selected from the group consisting of
(1) (2R)-1-[3,5-Bis(trifluoromethyl)benzoyl]-4-[4-((3S)-3-ethylmorpholino)-2-butynyl]-2-[(1H-indol-3-yl) methyl]piperazine,
(2) (2R)-1-[3,5-Bis(trifluoromethyl)benzoyl]-2-(3,4-dimethylbenzyl)-4-[2-((2S)-2-methoxymethyl-morpholino)ethyl]piperazine,
(3) (2R)-1-[3,5-Bis(trifluoromethyl)benzoyl]-2-(3,4-dimethylbenzyl)-4-[2-((3R)-3-methoxymethyl-morpholino)ethyl]piperazine,
(4) (2R)-1-[3,5-Bis(trifluoromethyl)benzoyl[-2-(3,4-dimethylbenzyl)-4-[2-((2R)-2-methoxymethyl-morpholino)ethyl]piperazine,
(5) (2R)-1-[3,5-Bis(trifluoromethyl)benzoyl]-2-[(1H-indol-3-yl)methyl]-4-[2-((2S)-2-methoxymethyl-morpholino)ethyl]piperazine, and
(6) (2R)-1-[3,5-Bis(trifluoromethyl)benzoyl]-4-[2-((3R)-3-ethylmorpholino)ethyl]-2-[(1H-indol-3-yl)-methyl] piperazine or a pharmaceutically acceptable salt thereof.

5. A process for the preparation-of the compound of claim 1 or a salt thereof, which comprises, (1) reacting a compound of the formula (II):

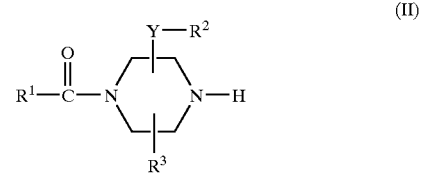

(II)

wherein $R^1$, $R^2$, $R^3$ and Y are each as defined in claim 1, or a salt thereof, with a compound of the formula (III):

$W_1$—$R^4$ (IV)

wherein $R^4$ is as defined in claim 1 and
$W_1$ is a leaving group,
or a salt thereof to give a compound of the formula (I):

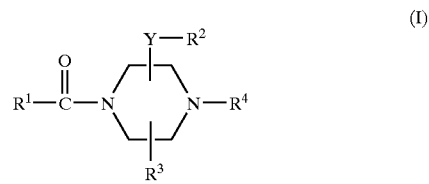

(I)

wherein $R^1$, $R^2$, $R^3$, $R^4$ and Y are each as defined in claim 1, or a salt thereof, (2) subjecting a compound of the formula (Ia):

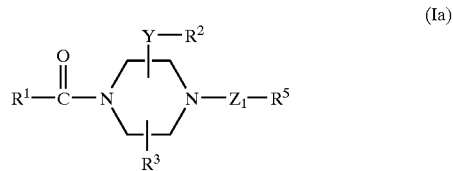

(Ia)

wherein $R^1$, $R^2$, $R^3$ and Y are each as defined above,
$R^5$ is 2-pyridyl which may have 1 to 3 substituent(s) selected from the group consisting of lower alkyl, lower alkoxy, lower alkoxycarbonyl, mono(or di or tri)halo(lower)alkyl and halogen; or 3-pyridyl which may have lower alkoxy or amino, and
$Z_1$ is lower alkynylene,
or a salt thereof to a reduction reaction to give a compound of the formula (Ib):

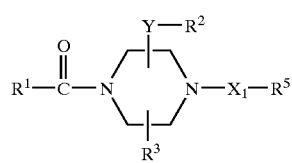

(Ib)

wherein $R^1$, $R^2$, $R^3$, Y and $R^5$ are each as defined above, and
$X_1$ is lower alkylene,
or a salt thereof, (3) reacting a compound of the formula (III):

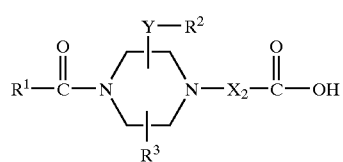

(III)

wherein $R^1$, $R^2$, $R^3$ and Y are each as defined above, and
$X_2$ is lower alkylene,
or its reactive derivative at the carboxy group or a salt thereof with a compound of the formula (V):

$H_2N\text{—}R^6$     (V)

wherein $R^6$ is saturated heterocyclic which may have substituent(s),
or a salt thereof to give a compound (Ic):

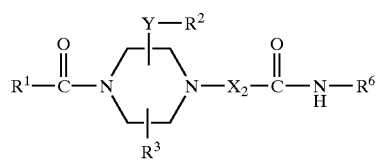

(Ic)

wherein $R^1$, $R^2$, $R^3$, $R^6$, $X_2$ and Y are each as defined above, (4) reacting a compound of the formula (VI):

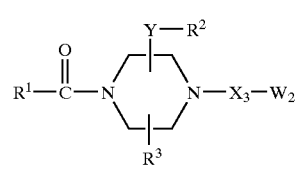

(VI)

wherein $R^1$, $R^2$, $R^3$ and Y are each as defined above,
$X_3$ is lower alkylene and
$W_2$ is a leaving group,
or a salt thereof with a compound of the formula (VII):

$H\text{—}R^7$     (VII)

wherein $R^7$ is pyridyl(lower)alkylamino;
N-(lower alkyl)-N-[pyridyl(lower)alkyl]-amino;
1-imidazolyl which may have 1 or 2 substituent(s) selected from the group consisting of lower alkyl, lower alkynyl, ar(lower)alkyl, pyridyl(lower)alkyl, mono(or di or tri)halo(lower)alkyl and halogen;

1-pyrazolyl which may have hydroxy(lower)alkyl, carboxy(lower)alkyl, lower alkoxycarbonyl(lower)alkyl, morpholinyl(lower)alkyl or morpholinylcarbonyl(lower)alkyl;
piperidino which may have hydroxy(lower)alkyl or lower alkoxy;
morpholino which has 1 or 2 substituent(s) selected from the group consisting of ethyl, hydroxy(lower)alkyl, halo(lower)alkyl and lower alkoxy(lower)alkyl;
morpholino which has lower alkyl and lower alkoxy(lower)alkyl;
3,5-dimethylmorpholino;
morpholinylamino which may have lower alkanoyl;
homomorpholinylamino; or
thiomorpholinylamino,
or a salt thereof to give a compound of the formula (Id):

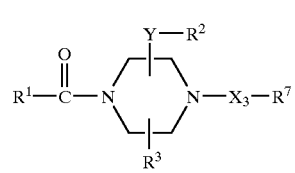

(Id)

wherein $R^1$, $R^2$, $R^3$, $R^7$, $X_3$ and Y are each as defined above,
or a salt thereof, (5) reacting a compound of the formula (VIII):

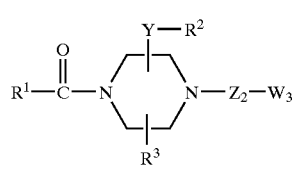

(VIII)

wherein $R^1$, $R^2$, $R^3$ and Y are each as defined above,
$Z_2$ is lower alkenylene, and
$W_3$ is a leaving group,
or a salt thereof with a compound of the formula (IX):

$H\text{—}R^8$     (IX)

wherein $R^8$ is morpholino which may have lower alkyl or lower alkoxy(lower)alkyl,
or a salt thereof to give a compound of the formula (Ie):

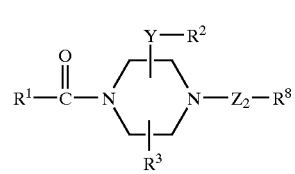

(Ie)

wherein $R^1$, $R^2$, $R^3$, $R^8$, Y and $Z_2$ are as defined as above,
or a salt thereof, (6) reacting compound of the formula (X):

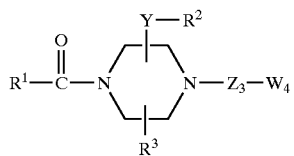
(X)

wherein $R^1$, $R^2$, $R^3$ and Y are each as defined above,
$Z_3$ is a lower alkynylene and
$W_4$ is a leaving group,
or a salt thereof with a compound of the formula (XI):

H—$R^9$ (XI)

wherein $R^9$ is pyrrolidino which may have lower alkoxy(lower) alkyl;
  morpholino which may have 1 or 2 substituent(s) selected from the group consisting of ethyl, propyl, isopropyl, isobutyl, spirocyclo(lower) alkyl, lower alkoxy(lower)alkyl, hydroxy(lower) alkyl, carboxy(lower)alkyl, di(lower alkyl) carbamoyl, lower alkoxycarbonyl and halo(lower) alkyl;
morpholino which has methyl and lower alkoxy; dimethylmorpholino; or
homomorpholino which has halogen,
or a salt thereof to give a compound of the formula (If):

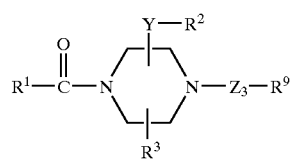
(If)

wherein $R^1$, $R^2$, $R^3$, $R^9$, Y and $Z_3$ are each as defined above,
or a salt thereof.

6. A pharmaceutical composition which comprises, as an active ingredient, a compound of claim 1 or a pharmaceutically acceptable salt thereof in admixture with pharmaceutically acceptable carriers.

7. A method for treating Tachykinin-mediated diseases which comprises administering an effective amount of a compound of claim 1 or a pharmaceutically acceptable salt thereof to human being or animals.

* * * * *